United States Patent [19]
Rivière et al.

[11] Patent Number: 6,140,111
[45] Date of Patent: *Oct. 31, 2000

[54] RETROVIRAL GENE THERAPY VECTORS AND THERAPEUTIC METHODS BASED THEREON

[75] Inventors: Isabelle Rivière, Boston, Mass.; Lawrence K. Cohen, Oakland, Calif.; Brad Guild, Concord, Mass.; Lori F. Rafield, San Francisco, Calif.; Paul Robbins, Mt. Lebanon, Pa.; Richard C. Mulligan, Lincoln, Mass.

[73] Assignees: Whitehead Institute for Biomedical Research, Cambridge, Mass.; Cell Genesys, Inc., Foster City, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/486,858

[22] Filed: Jun. 7, 1995

Related U.S. Application Data

[63] Continuation-in-part of application No. 08/252,710, Jun. 2, 1994, which is a continuation-in-part of application No. 07/786,015, Oct. 31, 1991, abandoned, which is a continuation-in-part of application No. 07/607,252, Oct. 31, 1990, abandoned, which is a continuation-in-part of application No. 08/131,926, Dec. 11, 1987, abandoned.

[51] Int. Cl.$^7$ .......................... C12N 15/63; C12N 15/85; C12N 15/82; A61K 48/00
[52] U.S. Cl. .................. 435/320.1; 435/456; 435/235.1; 514/44; 424/93.2
[58] Field of Search .................. 514/44; 435/320.1, 435/69.1, 70.1, 172.1, 172.3, 375, 377, 235.1, 440, 455, 456; 424/93.2, 93.21

[56] References Cited

U.S. PATENT DOCUMENTS

| | | | |
|---|---|---|---|
| 4,405,712 | 9/1983 | VandeWoude et al. | 435/5 |
| 4,868,116 | 9/1989 | Morgan et al. | 435/325.1 |
| 4,963,481 | 10/1990 | de Villiers et al. | 435/69.1 |
| 4,980,286 | 12/1990 | Morgan et al. | 435/440 |
| 5,399,346 | 3/1995 | Anderson et al. | 424/93.21 |

FOREIGN PATENT DOCUMENTS

| | | |
|---|---|---|
| 0150735 | 8/1985 | European Pat. Off. . |
| 0178220 | 4/1986 | European Pat. Off. . |
| 0378576 | 7/1995 | European Pat. Off. . |
| 8605807 | 10/1986 | WIPO . |
| 8902468 | 3/1989 | WIPO . |
| 8905345 | 6/1989 | WIPO . |
| 8907136 | 8/1989 | WIPO . |
| 9002806 | 3/1990 | WIPO . |
| 9006997 | 6/1990 | WIPO . |

OTHER PUBLICATIONS

R. Mulligan Science 260:926–932, May 14, 1993.
A.D. Miller Blood 76(2):271–278, Jul. 15, 1990.
A.D. Miller Nature 357:455–60, Jun. 11, 1992.
T. Friedman Science 244:1275–81, Jun. 16, 1989.
M. Kay TIG 10(7):253–7, Jul. 1994.
S. Orkin et al. NIH Gene Therapy Report, Dec. 7, 1995.

(List continued on next page.)

*Primary Examiner*—Deborah J. Clark
*Attorney, Agent, or Firm*—Roylance, Abrams, Berdo & Goodman, LLP

[57] ABSTRACT

Retroviral vectors are disclosed which include an insertion site for genes of interest and are capable of expressing high levels of the protein derived from the genes of interest in a wide variety of transfected cell types. Also disclosed are retroviral vectors lacking a selectable marker, thus rendering them suitable for human gene therapy in the treatment of a variety of disease states without the co-expression of a marker product, such as an antibiotic. These retroviral vectors are especially suited for use in certain packaging cell lines.

3 Claims, 31 Drawing Sheets

OTHER PUBLICATIONS

A. Coghlan New Scientist:14–15, Nov. 25, 1995.

D. Brown Washington Post, pp. A1 & A22, Dec. 8, 1995.

McLachlin et al. Retroviral–Mediated Gene Transfer. Progress in Nucleic–Acid Research and Molecular Biology, vol. 38, pp. 91–134, 1990.

Simons, J. W. et al., Apr. 15, 1997 Cancer Research 57, "Bioactivity of Autologous Irradiated Renal Cell Carcinoma Vaccines Generated by ex Vivo Granulocyte Macrophage Colony–stimulating Factor Gene Transfer", pp. 1537–1546.

Sanda, M. G. et al., Mar. 1994 IEEE The Journal of Urology, vol. 151, "Demonstration of a Rational Strategy for Human Prostate Cancer Gene Therapy", pp. 622–628.

Berns, Ph.D., A.J.M. et al., Mar. 1995 Human Gene Therapy, vol. 6, "Clinical Protocol Phase I Study of Non–Replicating Autologous Tumor Cell Injections Using Cells Prepared With or Without GM–CSF Gene Transduction in Patents with Metastatic Renal Cell Carcinoma", pp. 347–368.

Armentano et al. (1987) *Journal of Virology* 61(5):1647–1650.

Byun et al. (1996) *Gene Therapy* 3:780–788.

Ferry et al. (1991) *Proc. Natl. Acad. Sci. USA* 88:8377–8381.

Jaffe et al. (1993) *Cancer Research* 53:2221–2226.

Krall Et al. (1996) *Gene Therapy* 3:37–48.

Podrazik et al. (1992) *Ann. Surg.* 216(4):2221–2226.

Riviere et al.(1995) *Proc. Natl. Acad. Sci. USA* 92:6733–6737.

Sadelain et al. (1995) *Proc. Natl. Acad. Sci. USA* 92:6728–6732.

Watson et al. (1988) *Molecular Biology of the Gene*, Benjamin Cummings Publishing Company, Menlo Park, CA (1988) pp. 639–640.

Apperly, J.F. et al. "Retroviral Gene Transfer Of Human Adenosine Deaminase in Murine Hematopoietic Cells; effect of selectable marker sequences on long term expression," *Blood* 78(2):310–7 (1991).

Barklis, Eric et al. "Chromosomal Position of Virus Mutation Permits Retrovirus Expression in Embryonal Carcinoma Cells". *Cell*, 47: 391–399 (1986).

Beck–Engeser et al. "Retroviral Vectors Related to the Myeloproliferative Sarcoma Virus Allow Efficient Expression in Hematopoietic Stem and Precursor Cell Lines, but Retroviral Infection is Reduced in More Primitive Cells". *Human Gene Therapy* 2: 61–70 (1991).

Berwin, Brent and Barklis, Eric. "Retrovirus–mediated insertion of expressed and non–expressed genes at identical chromosomal locations", *Nucleic Acids Research* 21: 2399–2407 (1993).

Bodine, David M. et al. "Long–Term in Vivo Expression of a Murine Adenosine Deaminase Gene in Rhesus Monkey Hematopoietic Cells of Multiple Lineages After Retroviral Mediated Gene Transfer Into CD34+ Bone Marrow Cells", *Blood* 82(7): 1975–1980 1993.

Bosze, Zsuzsa et al. "A transcriptional enhancer with specificity for erythroid cells is located in the log terminal repeat of the Friend murine leukemia virus". *The EMBO Journal* 5(7): 1615–1623 (1986).

Bowtell, D.D.L. et al. "Expression of Genes Transferred to Haemopoietic Stem Cells by Recombinant Retroviruses". *Molecular Biology of Medicine* 4: 229–250 (1987).

Challita P. and Kohn D. "Lack of expression from a retroviral vector after transduction of murine hematopoietic stem cells is associated with methylation in vivo", *Proceedings of the National Academy of Sciences* 91: 2567–2571 (1994).

Colicelli, John and Goff, Stephen P. et al. "Isolation of a Recombinant Murine Leukemia Virus Utilizing a New Primer tRNA". *Journal of Virology:* 37–45 (1987).

Cone, Roger D. and Mulligan, Richard C. et al. "High–efficiency gene transfer into mammalian cells: Generation of helper–free recombinant retrovirus with broad mammalian host range". *Proceedings of the National Academy of Sciences,* USA 81: 6349–6353 (1984).

Danos, Olivier and Mulligan, Richard C. "Safe and efficient generation of recombinant retroviruses with amphotropic and ectropic host ranges". *Proceedings of the National Academy of Sciences* USA, 85: 6460–6464 (1988).

Einerland, M.P.W. et al. "Factors Affecting the Transduction of Pluripotent Hematopoietic Stem Cells: Long–term Expression of a Human Adenosine Deaminase Gene in Mice". *Blood* 81: 254–263 (1993).

Gilboa, Eli et al. "Transfer and Expression of Cloned Genes Using Retroviral Vectors". *BioTechniques* 4: 504–512 (1986).

Guild, Braydon C. et al. "Development of Retrovirus Vectors Useful for Expressing Genes in Cultured Murine Embryonal Cells and Hematopoietic Cells in Vivo". *Journal of Virology* 62: 395–3801 (1988).

Holland, Christie A. et al. "Enhancer sequences of a retroviral vector determine expression of a gene in multipotent hematopoietic progenitors and committed erythroid cells". *Proceedings of the National Academy of Sciences USA* 84: 8662–8666 (1987).

Kaleko, Michael et al. "Expression of Human Adenosine Deaminase in Mice After Transplantation of Genetically–Modified Bone Marrow". *Blood* 75: 1733–1741 (1990).

Kempler, Geraldine et al. "Characterization of the Moloney Murine Leukemia Virus Stem Cell–Specific Repressor Binding Site". *Virology* 193: 690–699 (1993).

Lim, Bing et al. "Long–term expression of human adenosine deaminase in mice transplanted with retrovirus–infected hematopoietic stem cells". *Proceedings of the National Academy of Sciences,* USA 86: 8892–8896 (1989).

Moore, Kateri A. et al. "Human Adenosine Deaminase Expression in Mice". *Blood* 75: 2085–1092 (1990).

Mann, Richard et al. "Construction of a Retrovirus Packaging Mutant and Its Use to Produce helper–Free Defective Retrovirus". *Cell* 33: 153–159 (1983).

Mulligan, Richard. "Construction of Highly Transmissible Mammalian Cloning Vehicles Derived from Murine Retroviruses". *Experimental Manipulation of Gene Expression.* Academic Press, Inc. 1983. pp. 155–173.

Ohashi, Toya et al. "Efficient transfer and sustained high expression of the human glucocerebrosidase gene in mice and their functional macrophages following transplantation of bone marrow transduced by a retroviral vector". *Proceedings of the National Academy of Sciences USA* 89: 11332–11336 (1992).

Stocking, Carol et al. "Long terminal repeat sequences impart hematopoietic transformation properties to the myeloproliferative sarcoma virus". *Proceedings of the National Academy of Sciences USA* 82(17): 5746–5750 (1985).

Thiesen, Hans–Jurgen et al. "A DNA Element Responsible for the Different Tissue Specificities of Friend and Moloney Retroviral Enhancers". *Journal of Virology* 62: 614–618 (1988).

van Beusechem, Victor W. et al. "Long–term expression of human adenosine deaminase in rhesus monkeys transplanted with retrovirus–infected bone–marrow cells". *Proceedings of the National Academy of Sciences USA* 89: 7640–7644 (1992).

van Beusechem, V.W. et al. "Expression of Human Adenosine Deaminase in Mice Transplanted with Hemopoietic Stem Cells Infected with Amphotropic Retroviruses". *J. Exp. Med.* 172: 729–736 (1990).

Weiher, Hans et al. "Two Distinct Sequence Elements Mediate Retroviral Gene Expression in Embryonal Carcinoma Cells". *Journal of Virology* 61: 2742–2746 (1987).

Williams, David A. et al. "Introduction of new genetic material into pluripotent haematopoietic stem cells of the mouse". *Nature* 310: 476–480 (1984).

Wilson, James M. et al. "Expression of human adenosine deaminase in mice reconstituted with retrovirus–transduced hematopoietic stem cells". *Proceedings of the National Academy of Sciences USA* 87: 439–443 (1990).

Anderson, W.F. "Prospects for human gene therapy," *Science* 226:401–409 (1984).

Bender, M.A. et al."Evidence that the packaging signal of moloney murine leukemia virus extends into the gag region," *J. Virol.* 61(5):1639–1646 (1987).

Cone, R.D. et al. "High–efficiency gene transfer into mammalian cells generation of helper free recombinant retrovirus with broad mammalian host range" *Proc. Natl. Acad. Sci. USA* 81:6349–6353 (1984).

Emerman, M. et al. "High frequency deletion in recovered retrovirus vectors containing exogenous DNA with promoters," *J. Virol.* 50(1):42–49 (1984).

Franz, T. et al. "Retroviral mutants efficiently expressed in embryonal carcinoma cells," *Proc. Natl. Acad. Sci. USA* 83:3292–3296 (1986).

Hilberg, F. et al. "Functional analysis of a retroviral host–range mutant altered long terminal repeat sequences allow expression in embryonal carcinoma cells," *Proc. Natl. Acad. Sci. USA* 84:5232–5236 (1987).

Holland, C.A. et al. "Enhancer sequences of a retroviral vector determine expression of a gene in multipotent hematopoietic progenitors and committed erythroid cells," *Proc. Natl. Acad. Sci. USA* 84:8662–8666 (1987).

Temin, H. in Gene Transfer, R. Kucherlapati (Ed.), Plenum Press, N.Y., pp. 149–187 (1986).

Yee, J.K. et al. "Gene expression from transcriptionally disabled retroviral vectors," *Proc. Natl. Acad. Sci. USA* 84:5197–5202 (1987).

Yu, S.F. et al. "Self–inactivating retroviral vectors designed for transfer of whole genes into mammalian cells," *Proc. Natl. Acad. Sci. USA* 83:3194–3198 (1986).

Gilboa, E. "Retrovirus vectors and their uses in molecular biology," *Bioessays* 5(6):252–257 (1986).

Lim, B. et al. "Retrovirus–mediated gene transfer of human adenosine deaminase: expression of functional enzyme in murine hematopoietic stem cells in vivo," *Molec. Cell. Biol.* 7(10):3459–3465 (1987).

Wilson, J. et al. "Correction of the genetic defect in hepatocytes from the Watanabe heritable hyperlipidemic rabbit," *Proc. of the Natl. Academy of Sci.* 85:4421–4425 (1988).

Israel et al. "Retroviral–mediated transfer and amplification of a functional human factor VIII gene," *Blood* 75(5):1074–1080 (1990).

Morgenstern et al. "Advanced mammalian gene transfer: high titre retroviral vectors with multiple drug selection markers and a complementary helper–free packaging cell line," *Nucleic Acids Research* 18(12):3587–3597 (1990).

Hurford Jr., R. et al. "Gene therapy of metastatic cancer by in vivo retroviral gene targeting," *Nat. Genet.* 10(4):430–435 (1995).

FIG. 2A pLJ 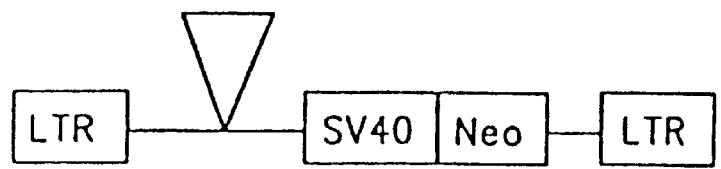
FIG. 2B pEm 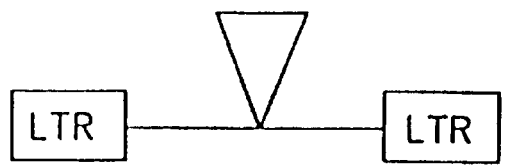
FIG. 2C MFG 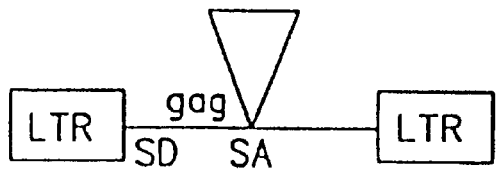
FIG. 2D αSGC 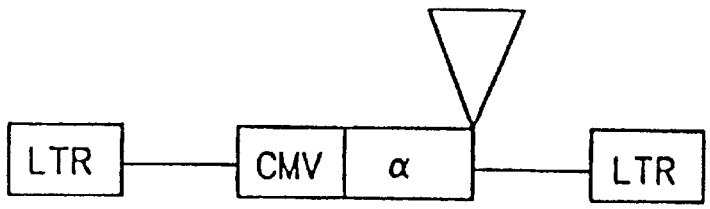

αSGC-LacZ

| | | | | | | | | | | | | | | | | |
|---|---|---|---|---|---|---|---|---|---|---|---|---|---|---|---|---|
| Mo-LTR | | 191 | 402 | 1.0 | | 191 | 402 | 0.7 | | 191 | 402 | 0.8 | | | | |
| 80% (n=3) | #39 | 0.9 | | | #40 | 1.4 | | | #41 | 1.0 | | | | | | |
| Mo-LTR/B2 | | 191 | 424 | 1.5 | | 191 | 424 | 1.1 | | 191 | 424 | 2 | | 191 | 424 | 1.2 |
| 82% (n=4) | #54 | 1.8 | | | #56 | 1.8 | | | #57 | 1.8 | | | #58 | 1.7 | | |
| Fr-Enh | | 184 | 430 | 1.3 | | 184 | 430 | 0.8 | | 184 | 430 | 1.6 | | 184 | 430 | 0.6 |
| 80% (n=4) | #15 | 1.6 | | | #16 | 1.4 | | | #17 | 1.2 | | | #18 | 1.2 | | |
| MPSV-LTR | | 177 | 361 | 1.7 | | 177 | 361 | 2.0 | | 177 | ND | ND | | 177 | 411 | ND |
| 77% (n=4) | #126 | 2.2 | | | #127 | 2.2 | | | #129 | 1.8 | | | #141 | ND | | |
| αG-SGC | | 170 | 420 | 0.4 | | 170 | 420 | 0.03 | | 170 | 399 | ND | | 170 | 420 | 0.4 |
| 59% (n=3) | #117 | 0.6 | | | #121 | 0.05 | | | #123 | ND | | | #118 | 0.8 | | |
| CONTROL– NO VECTOR | | | | | | | | | | 177 | 411 | 1.5 | | 177 | 411 | 1.4 |
| | | | | | | | | | #142 | 2.5 | | | #144 | 1.9 | | |

Header annotations: DAYS AFTER BMT, hADA, mADA, RATIO hADA/mADA; rightmost column arrow: mADA

FIG. 12C

```
MoMuLV: GGTGGAACTGACGAGTTCGGAACACCCGGCCGCAACCCTGGGAGACGTCCCAGGGACTTCGGGGGCCGTTTTTGTGGCCCGACCT
MFG:    XXXXXXXXXXXXXXXXXXXXXXXXXXXXXXXXXXXXXXXXXXXXXXXXXXXXXXXXXXXXXXXXXXXXXXXXXXXXXXXXXXXXX
MFG-S:  XXXXXXXXXXXXXXXXXXXXXXXXXXXXXXXXXXXXXXXXXXXXXXXXXXXXXXXXXXXXXXXXXXXXXXXXXXXXXXXXXXXXX

MoMuLV: GAGTCCAAAAATCCCGATCGTTTTGGACTCTTTGGTGCACCCCCCTTAGAGGAGGGATATGTGGTTCTGGTAGGAGACGAGAACC
MFG:    XXXXXXXXXXXXXXXXXXXXXXXXXXXXXXXXXXXXXXXXXXXXXXXXXXXXXXXXXXXXXXXXXXXXXXXXXXXXXXXXXXXXX
MFG-S:  XXXXXXTXXXXXXXXXXXXXXXXAXXXXXXXXXXXXXXXXXXXXXXXXXXXXXXXXXXXXXXXXXXXXXXXXXXXXXXXXXXXXX

MoMuLV: TAAAACAGTTCCCGCCTCCGTCTGAATTTTTGCTTTCGGTTTGGGACCGAAGCCGCGCCGCGTCTTGTCTGCTGCAGCATCGT
MFG:    XXXXXXXXXXXXXXXXXXXXXXXXXXXXXXXXXXXXXXXXXXXXXXXXXXXXXXXXXXXXXXXXXXXXXXXXXXXXXXXXXXX
MFG-S:  XXXXXXXXXXXXXXXXXXXXXXXXXXXXXXXXXXXXXXXXXXXXXXXXXXXXXXXXXXXXXXXXXXXXXXXXXXXXXXXXXXX

MoMuLV: TCTGTGTTGTCTCTGTCTGACTGTGTTTCTGTATTTGTCTGAGAATATGGG------CCAGACTGTTACCACTCCCT
MFG:    XXXXXXXXXXXXXXXXXXXXXXXXXXXXXXXXXXXXXXXXXXXXXXXXXXXCCCGGGXXXXXXXXXXXXXXXXXXXX
MFG-S:  XXXXXXXXXXXXXXXXXXXXXXXXXXXXXXXXXXXXXXXXXXXXXXXXXXXCCCGGGXTXXXXXXXXXXXXXXXXXX
```

```
  1  AAGCTTTGCT CTTAGGAGTT TCCTAATACA TCCCAAACTC AAATATATAA AGCATTTGAC
     TTCGAAACGA GAATCCTCAA AGGATTATGT AGGGTTTGAG TTTATATATT TCGTAAACTG

61  TTGTTCTATG CCCTAGGGGG CGGGGGGAAG CTAAGCCAGC TTTTTTTAAC ATTTAAAATG
     AACAAGATAC GGGATCCCCC GCCCCCCTTC GATTCGGTCG AAAAAAATTG TAAATTTTAC

121  TTAATTCCAT TTTAAATGCA CAGATGTTTT TATTTCATAA GGGTTTCAAT GTGCATGAAT
     AATTAAGGTA AAATTTACGT GTCTACAAAA ATAAAGTATT CCCAAAGTTA CACGTACTTA

181  GCTGCAATAT TCCTGTTACC AAAGCTAGTA TAAATAAAAA TAGATAAACG TGGAAATTAC
     CGACGTTATA AGGACAATGG TTTCGATCAT ATTTATTTTT ATCTATTTGC ACCTTTAATG

241  TTAGAGTTTC TGTCATTAAC GTTTCCTTCC TCAGTTGACA ACATAAATGC GCTGCTGAGC
     AATCTCAAAG ACAGTAATTG CAAAGGAAGG AGTCAACTGT TGTATTTACG CGACGACTCG

301  AAGCCAGTTT GCATCTGTCA GGATCAATTT CCCATTATGC CAGTCATATT AATTACTAGT
     TTCGGTCAAA CGTAGACAGT CCTAGTTAAA GGGTAATACG GTCAGTATAA TTAATGATCA

361  CAATTAGTTG ATTTTTATTT TTGACATATA CATGTGAATG AAAGACCCCA CCTGTAGGTT
     GTTAATCAAC TAAAAATAAA AACTGTATAT GTACACTTAC TTTCTGGGGT GGACATCCAA

421  TGGCAAGCTA GCTTAAGTAA CGCCATTTTG CAAGGCATGG AAAAATACAT AACTGAGAAT
     ACCGTTCGAT CGAATTCATT GCGGTAAAAC GTTCCGTACC TTTTTATGTA TTGACTCTTA

481  AGAAAAGTTC AGATCAAGGT CAGGAACAGA TGGAACAGCT GAATATGGGC CAAACAGGAT
     TCTTTTCAAG TCTAGTTCCA GTCCTTGTCT ACCTTGTCGA CTTATACCCG GTTTGTCCTA

541  ATCTGTGGTA AGCAGTTCCT GCCCCGGCTC AGGGCCAAGA ACAGATGGAA CAGCTGAATA
     TAGACACCAT TCGTCAAGGA CGGGGCCGAG TCCCGGTTCT TGTCTACCTT GTCGACTTAT

601  TGGGCCAAAC AGGATATCTG TGGTAAGCAG TTCCTGCCCC GGCTCAGGGC CAAGAACAGA
     ACCCGGTTTG TCCTATAGAC ACCATTCGTC AAGGACGGGG CCGAGTCCCG GTTCTTGTCT

661  TGGTCCCCAG ATGCGGTCCA GCCCTCAGCA GTTTCTAGAG AACCATCAGA TGTTTCCAGG
     ACCAGGGGTC TACGCCAGGT CGGGAGTCGT CAAAGATCTC TTGGTAGTCT ACAAAGGTCC

721  GTGCCCCAAG GACCTGAAAT GACCCTGTGC CTTATTTGAA CTAACCAATC AGTTCGCTTC
     CACGGGGTTC CTGGACTTTA CTGGGACACG GAATAAACTT GATTGGTTAG TCAAGCGAAG

781  TCGCTTCTGT TCGCGCGCTT CTGCTCCCCG AGCTCAATAA AAGAGCCCAC AACCCCTCAC
     AGCGAAGACA AGCGCGCGAA GACGAGGGGC TCGAGTTATT TTCTCGGGTG TTGGGGAGTG
```

FIG. 17A

```
 841  TCGGGGCGCC AGTCCTCCGA TTGACTGAGT CGCCCGGGTA CCCGTGTATC CAATAAACCC
      AGCCCCGCGG TCAGGAGGCT AACTGACTCA GCGGGCCCAT GGGCACATAG GTTATTTGGG

901  TCTTGCAGTT GCATCCGACT TGTGGTCTCG CTGTTCCTTG GGAGGGTCTC CTCTGAGTGA
      AGAACGTCAA CGTAGGCTGA ACACCAGAGC GACAAGGAAC CCTCCCAGAG GAGACTCACT

961  TTGACTACCC GTCAGCGGGG GTCTTTCATT TGGGGGCTCG TCCGGGATCG GGAGACCCCT
      AACTGATGGG CAGTCGCCCC CAGAAAGTAA ACCCCCGAGC AGGCCCTAGC CCTCTGGGGA

1021  GCCCAGGGAC CACCGACCCA CCACCGGGAG GTAAGCTGGC CAGCAACTTA TCTGTGTCTG
      CGGGTCCCTG GTGGCTGGGT GGTGGCCCTC CATTCGACCG GTCGTTGAAT AGACACAGAC

1081  TCCGATTGTC TAGTGTCTAT GACTGATTTT ATGCGCCTGC GTCGGTACTA GTTAGCTAAC
      AGGCTAACAG ATCACAGATA CTGACTAAAA TACGCGGACG CAGCCATGAT CAATCGATTG

1141  TAGCTCTGTA TCTGGCGGAC CCGTGGTGGA ACTGACGAGT TCGGAACACC CGGCCGCAAC
      ATCGAGACAT AGACCGCCTG GGCACCACCT TGACTGCTCA AGCCTTGTGG GCCGGCGTTG

1201  CCTGGGAGAC GTCCCAGGGA CTTCGGGGGC CGTTTTTGTG GCCCGACCTG AGTCCTAAAA
      GGACCCTCTG CAGGGTCCCT GAAGCCCCCG GCAAAAACAC CGGGCTGGAC TCAGGATTTT

1261  TCCCGATCGT TTAGGACTCT TTGGTGCACC CCCCTTAGAG GAGGGATATG TGGTTCTGGT
      AGGGCTAGCA AATCCTGAGA AACCACGTGG GGGGAATCTC CTCCCTATAC ACCAAGACCA

1321  AGGAGACGAG AACCTAAAAC AGTTCCCGCC TCCGTCTGAA TTTTTGCTTT CGGTTTGGGA
      TCCTCTGCTC TTGGATTTTG TCAAGGGCGG AGGCAGACTT AAAAACGAAA GCCAAACCCT

1381  CCGAAGCCGC GCCGCGCGTC TTGTCTGCTG CAGCATCGTT CTGTGTTGTC TCTGTCTGAC
      GGCTTCGGCG CGGCGCGCAG AACAGACGAC GTCGTAGCAA GACACAACAG AGACAGACTG

1441  TGTGTTTCTG TATTTGTCTG AAAATATGGG CCCGGGCTAG ACTGTTACCA CTCCCTTAAG
      ACACAAAGAC ATAAACAGAC TTTTATACCC GGGCCCGATC TGACAATGGT GAGGGAATTC

1501  TTTGACCTTA GGTCACTGGA AAGATGTCGA GCGGATCGCT CACAACCAGT CGGTAGATGT
      AAACTGGAAT CCAGTGACCT TTCTACAGCT CGCCTAGCGA GTGTTGGTCA GCCATCTACA

1561  CAAGAAGAGA CGTTGGGTTA CCTTCTGCTC TGCAGAATGG CCAACCTTTA ACGTCGGATG
      GTTCTTCTCT GCAACCCAAT GGAAGACGAG ACGTCTTACC GGTTGGAAAT TGCAGCCTAC
```

FIG. 17B

1621 GCCGCGAGAC GGCACCTTTA ACCGAGACCT CATCACCCAG GTTAAGATCA AGGTCTTTTC
     CGGCGCTCTG CCGTGGAAAT TGGCTCTGGA GTAGTGGGTC CAATTCTAGT TCCAGAAAAG

1681 ACCTGGCCCG CATGGACACC CAGACCAGGT CCCCTACATC GTGACCTGGG AAGCCTTGGC
     TGGACCGGGC GTACCTGTGG GTCTGGTCCA GGGGATGTAG CACTGGACCC TTCGGAACCG

1741 TTTTGACCCC CCTCCCTGGG TCAAGCCCTT TGTACACCCT AAGCCTCCGC CTCCTCTTCC
     AAAACTGGGG GGAGGGACCC AGTTCGGGAA ACATGTGGGA TTCGGAGGCG GAGGAGAAGG

1801 TCCATCCGCC CCGTCTCTCC CCCTTGAACC TCCTCGTTCG ACCCCGCCTC GATCCTCCCT
     AGGTAGGCGG GGCAGAGAGG GGGAACTTGG AGGAGCAAGC TGGGGCGGAG CTAGGAGGGA

1861 TTATCCAGCC CTCACTCCTT CTCTAGGCGC CCCCATATGG CCATATGAGA TCTTATATGG
     AATAGGTCGG GAGTGAGGAA GAGATCCGCG GGGGTATACC GGTATACTCT AGAATATACC

1921 GGCACCCCCG CCCCTTGTAA ACTTCCCTGA CCCTGACATG ACAAGAGTTA CTAACAGCCC
     CCGTGGGGGC GGGGAACATT TGAAGGGACT GGGACTGTAC TGTTCTCAAT GATTGTCGGG

1981 CTCTCTCCAA GCTCACTTAC AGGCTCTCTA CTTAGTCCAG CACGAAGTCT GGAGACCTCT
     GAGAGAGGTT CGAGTGAATG TCCAGAGAT GAATCAGGTC GTGCTTCAGA CCTCTGGAGA

2041 GGCGGCAGCC TACCAAGAAC AACTGGACCG ACCGGTGGTA CCTCACCCTT ACCGAGTCGG
     CCGCCGTCGG ATGGTTCTTG TTGACCTGGC TGGCCACCAT GGAGTGGGAA TGGCTCAGCC

2101 CGACACAGTG TGGGTCCGCC GACACCAGAC TAAGAACCTA GAACCTCGCT GGAAAGGACC
     GCTGTGTCAC ACCCAGGCGG CTGTGGTCTG ATTCTTGGAT CTTGGAGCGA CCTTTCCTGG

2161 TTACACAGTC CTGCTGACCA CCCCCACCGC CCTCAAAGTA GACGGCATCG CAGCTTGGAT
     AATGTGTCAG GACGACTGGT GGGGGTGGCG GGAGTTTCAT CTGCCGTAGC GTCGAACCTA

2221 ACACGCCGCC CACGTGAAGG CTGCCGACCC CGGGGGTGGA CCATCCTCTA GACTGCCATG
     TGTGCGGCGG GTGCACTTCC GACGGCTGGG GCCCCCACCT GGTAGGAGAT CTGACGGTAC

2281 GCGCGGATCC GGATTAGTCC AATTTGTTAA AGACAGGATA TCAGTGGTCC AGGCTCTAGT
     CGCGCCTAGG CCTAATCAGG TTAAACAATT TCTGTCCTAT AGTCACCAGG TCCGAGATCA

2341 TTTGACTCAA CAATATCACC AGCTGAAGCC TATAGAGTAC GAGCCATAGA TAAAATAAAA
     AAACTGAGTT GTTATAGTGG TCGACTTCGG ATATCTCATG CTCGGTATCT ATTTTATTTT

FIG. 17C

```
2401  GATTTTATTT AGTCTCCAGA AAAAGGGGGG AATGAAAGAC CCCACCTGTA GGTTTGGCAA
      CTAAAATAAA TCAGAGGTCT TTTTCCCCCC TTACTTTCTG GGGTGGACAT CCAAACCGTT

2461  GCTAGCTTAA GTAACGCCAT TTTGCAAGGC ATGGAAAAAT ACATAACTGA GAATAGAGAA
      CGATCGAATT CATTGCGGTA AAACGTTCCG TACCTTTTTA TGTATTGACT CTTATCTCTT

2521  GTTCAGATCA AGGTCAGGAA CAGATGGAAC AGCTGAATAT GGGCCAAACA GGATATCTGT
      CAAGTCTAGT TCCAGTCCTT GTCTACCTTG TCGACTTATA CCCGGTTTGT CCTATAGACA

2581  GGTAAGCAGT TCCTGCCCCG GCTCAGGGCC AAGAACAGAT GGAACAGCTG AATATGGGCC
      CCATTCGTCA AGGACGGGGC CGAGTCCCGG TTCTTGTCTA CCTTGTCGAC TTATACCCGG

2641  AAACAGGATA TCTGTGGTAA GCAGTTCCTG CCCCGGCTCA GGGCCAAGAA CAGATGGTCC
      TTTGTCCTAT AGACACCATT CGTCAAGGAC GGGGCCGAGT CCCGGTTCTT GTCTACCAGG

2701  CCAGATGCGG TCCAGCCCTC AGCAGTTTCT AGAGAACCAT CAGATGTTTC AGGGTGCCC
      GGTCTACGCC AGGTCGGGAG TCGTCAAAGA TCTCTTGGTA GTCTACAAAG GTCCCACGGG

2761  CAAGGACCTG AAATGACCCT GTGCCTTATT TGAACTAACC AATCAGTTCG CTTCTCGCTT
      GTTCCTGGAC TTTACTGGGA CACGGAATAA ACTTGATTGG TTAGTCAAGC GAAGAGCGAA

2821  CTGTTCGCGC GCTTCTGCTC CCCGAGCTCA ATAAAAGAGC CCACAACCCC TCACTCGGGG
      GACAAGCGCG CGAAGACGAG GGGCTCGAGT TATTTTCTCG GGTGTTGGGG AGTGAGCCCC

2881  CGCCAGTCCT CCGATTGACT GAGTCGCCCG GGTACCCGTG TATCCAATAA ACCCTCTTGC
      GCGGTCAGGA GGCTAACTGA CTCAGCGGGC CCATGGGCAC ATAGGTTATT TGGGAGAACG

2941  AGTTGCATCC GACTTGTGGT CTCGCTGTTC CTTGGGAGGG TCTCCTCTGA GTGATTGACT
      TCAACGTAGG CTGAACACCA GAGCGACAAG GAACCCTCCC AGAGGAGACT CACTAACTGA

3001  ACCCGTCAGC GGGGGTCTTT CACACATGCA GCATGTATCA AAATTAATTT GGTTTTTTTT
      TGGGCAGTCG CCCCCAGAAA GTGTGTACGT CGTACATAGT TTTAATTAAA CCAAAAAAAA

3061  CTTAAGTATT TACATTAAAT GGCCATAGTA CTTAAAGTTA CATTGGCTTC CTTGAAATAA
      GAATTCATAA ATGTAATTTA CCGGTATCAT GAATTTCAAT GTAACCGAAG GAACTTTATT

3121  ACATGGAGTA TTCAGAATGT GTCATAAATA TTTCTAATTT TAAGATAGTA TCTCCATTGG
      TGTACCTCAT AAGTCTTACA CAGTATTTAT AAAGATTAAA ATTCTATCAT AGAGGTAACC

3181  CTTTCTACTT TTTCTTTTAT TTTTTTTTGT CCTCTGTCTT CCATTTGTTG TTGTTGTTGT
      GAAAGATGAA AAAGAAAATA AAAAAAAACA GGAGACAGAA GGTAAACAAC AACAACAACA
```

FIG. 17D

```
3241 TTGTTTGTTT GTTTGTTGGT TGGTTGGTTA ATTTTTTTTT AAAGATCCTA CACTATAGTT
     AACAAACAAA CAAACAACCA ACCAACCAAT TAAAAAAAAA TTTCTAGGAT GTGATATCAA

3301 CAAGCTAGAC TATTAGCTAC TCTGTAACCC AGGGTGACCT TGAAGTCATG GGTAGCCTGC
     GTTCGATCTG ATAATCGATG AGACATTGGG TCCCACTGGA ACTTCAGTAC CCATCGGACG

3361 TGTTTTAGCC TTCCCACATC TAAGATTACA GGTATGAGCT ATCATTTTTG GTATATTGAT
     ACAAAATCGG AAGGGTGTAG ATTCTAATGT CCATACTCGA TAGTAAAAAC CATATAACTA

3421 TGATTGATTG ATTGATGTGT GTGTGTGTGA TTGTGTTTGT GTGTGTGANT GTGWANATGT
     ACTAACTAAC TAACTACACA CACACACACT AACACAAACA CACACACTNA CACWTNTACA

3481 GTGTATGGNT GTGTGTGAKT GTGTGTATGT ATGNYTGTGT GTGANTGYGT GTGTGTGANT
     CACATACCNA CACACACTMA CACACATACA TACNRACACA CACTNACRCA CACACACTNA

3541 GTGCATGTGT GTGTGTGTGA CTGTGTCTAT GTGTATGACT GTGTGTGTGT GTGTGTGTGT
     CACGTACACA CACACACACT GACACAGATA CACATACTGA CACACACACA CACACACACA

3601 GTGTGTGTGT GTGTGTGTGT GTGTGTTGTG AAAAAATATT CTATGGTAGT GAGAGCCAAC
     CACACACACA CACACACACA CACACAACAC TTTTTTATAA GATACCATCA CTCTCGGTTG

3661 GCTCCGGCTC AGGTGTCAGG TTGGTTTTTG AGACAGAGTC TTTCACTTAG CTTGGAATTC
     CGAGGCCGAG TCCACAGTCC AACCAAAAAC TCTGTCTCAG AAAGTGAATC GAACCTTAAG

3721 TTGAAGACGA AAGGGCCTCG TGATACGCCT ATTTTTATAG GTTAATGTCA TGATAATAAT
     AACTTCTGCT TTCCCGGAGC ACTATGCGGA TAAAAATATC CAATTACAGT ACTATTATTA

3781 GGTTTCTTAG ACGTCAGGTG GCACTTTTCG GGGAAATGTG CGCGGAACCC CTATTTGTTT
     CCAAAGAATC TGCAGTCCAC CGTGAAAAGC CCCTTTACAC GCGCCTTGGG GATAAACAAA

3841 ATTTTTCTAA ATACATTCAA ATATGTATCC GCTCATGAGA CAATAACCCT GATAAATGCT
     TAAAAAGATT TATGTAAGTT TATACATAGG CGAGTACTCT GTTATTGGGA CTATTTACGA

3901 TCAATAATAT TGAAAAAGGA AGAGTATGAG TATTCAACAT TTCCGTGTCG CCCTTATTCC
     AGTTATTATA ACTTTTTCCT TCTCATACTC ATAAGTTGTA AAGGCACAGC GGGAATAAGG

3961 CTTTTTTGCG GCATTTTGCC TTCCTGTTTT TGCTCACCCA GAAACGCTGG TGAAAGTAAA
     GAAAAAACGC CGTAAAACGG AAGGACAAAA ACGAGTGGGT CTTTGCGACC ACTTTCATTT

4021 AGATGCTGAA GATCAGTTGG GTGCACGAGT GGGTTACATC GAACTGGATC TCAACAGCGG
     TCTACGACTT CTAGTCAACC CACGTGCTCA CCCAATGTAG CTTGACCTAG AGTTGTCGCC
```

FIG. 17E

4081 TAAGATCCTT GAGAGTTTTC GCCCCGAAGA ACGTTTTCCA ATGATGAGCA CTTTTAAAGT
     ATTCTAGGAA CTCTCAAAAG CGGGGCTTCT TGCAAAAGGT TACTACTCGT GAAAATTTCA

4141 TCTGCTATGT GGCGCGGTAT TATCCCGTGT TGACGCCGGG CAAGAGCAAC TCGGTCGCCG
     AGACGATACA CCGCGCCATA ATAGGGCACA ACTGCGGCCC GTTCTCGTTG AGCCAGCGGC

4201 CATACACTAT TCTCAGAATG ACTTGGTTGA GTACTCACCA GTCACAGAAA AGCATCTTAC
     GTATGTGATA AGAGTCTTAC TGAACCAACT CATGAGTGGT CAGTGTCTTT TCGTAGAATG

4261 GGATGGCATG ACAGTAAGAG AATTATGCAG TGCTGCCATA ACCATGAGTG ATAACACTGC
     CCTACCGTAC TGTCATTCTC TTAATACGTC ACGACGGTAT TGGTACTCAC TATTGTGACG

4321 GGCCAACTTA CTTCTGACAA CGATCGGAGG ACCGAAGGAG CTAACCGCTT TTTTGCACAA
     CCGGTTGAAT GAAGACTGTT GCTAGCCTCC TGGCTTCCTC GATTGGCGAA AAAACGTGTT

4381 CATGGGGGAT CATGTAACTC GCCTTGATCG TTGGGAACCG GAGCTGAATG AAGCCATACC
     GTACCCCCTA GTACATTGAG CGGAACTAGC AACCCTTGGC CTCGACTTAC TTCGGTATGG

4441 AAACGACGAG CGTGACACCA CGATGCCTGC AGCAATGGCA ACAACGTTGC GCAAACTATT
     TTTGCTGCTC GCACTGTGGT GCTACGGACG TCGTTACCGT TGTTGCAACG CGTTTGATAA

4501 AACTGGCGAA CTACTTACTC TAGCTTCCCG GCAACAATTA ATAGACTGGA TGGAGGCGGA
     TTGACCGCTT GATGAATGAG ATCGAAGGGC CGTTGTTAAT TATCTGACCT ACCTCCGCCT

4561 TAAAGTTGCA GGACCACTTC TGCGCTCGGC CCTTCCGGCT GGCTGGTTTA TTGCTGATAA
     ATTTCAACGT CCTGGTGAAG ACGCGAGCCG GGAAGGCCGA CCGACCAAAT AACGACTATT

4621 ATCTGGAGCC GGTGAGCGTG GGTCTCGCGG TATCATTGCA GCACTGGGGC CAGATGGTAA
     TAGACCTCGG CCACTCGCAC CCAGAGCGCC ATAGTAACGT CGTGACCCCG GTCTACCATT

4681 GCCCTCCCGT ATCGTAGTTA TCTACACGAC GGGGAGTCAG GCAACTATGG ATGAACGAAA
     CGGGAGGGCA TAGCATCAAT AGATGTGCTG CCCCTCAGTC CGTTGATACC TACTTGCTTT

4741 TAGACAGATC GCTGAGATAG GTGCCTCACT GATTAAGCAT TGGTAACTGT CAGACCAAGT
     ATCTGTCTAG CGACTCTATC CACGGAGTGA CTAATTCGTA ACCATTGACA GTCTGGTTCA

FIG. 17F

```
4801  TTACTCATAT ATACTTTAGA TTGATTTAAA ACTTCATTTT TAATTTAAAA GGATCTAGGT
      AATGAGTATA TATGAAATCT AACTAAATTT AGAAGTAAAA ATTAAATTTT CCTAGATCCA

4861  GAAGATCCTT TTTGATAATC TCATGACCAA AATCCCTTAA CGTGAGTTTT CGTTCCACTG
      CTTCTAGGAA AAACTATTAG AGTACTGGTT TTAGGGAATT GCACTCAAAA GCAAGGTGAC

4921  AGCGTCAGAC CCCGTAGAAA AGATCAAAGG ATCTTCTTGA GATCCTTTTT TTCTGCGCGT
      TCGCAGTCTG GGGCATCTTT TCTAGTTTCC TAGAAGAACT CTAGGAAAAA AAGACGCGCA

4981  AATCTGCTGC TTGCAAACAA AAAAACCACC GCTACCAGCG GTGGTTTGTT TGCCGGATCA
      TTAGACGACG AACGTTTGTT TTTTGGTGG CGATGGTCGC CACCAAACAA ACGGCCTAGT

5041  AGAGCTACCA ACTCTTTTTC CGAAGGTAAC TGGCTTCAGC AGAGCGCAGA TACCAAATAC
      TCTCGATGGT TGAGAAAAAG GCTTCCATTG ACCGAAGTCG TCTCGCGTCT ATGGTTTATG

5101  TGTCCTTCTA GTGTAGCCGT AGTTAGGCCA CCACTTCAAG AACTCTGTAG CACCGCCTAC
      ACAGGAAGAT CACATCGGCA TCAATCCGGT GGTGAAGTTC TTGAGACATC GTGGCGGATG

5161  ATACCTCGCT CTGCTAATCC TGTTACCAGT GGCTGCTGCC AGTGGCGATA AGTCGTGTCT
      TATGGAGCGA GACGATTAGG ACAATGGTCA CCGACGACGG TCACCGCTAT TCAGCACAGA

5221  TACCGGGTTG GACTCAAGAC GATAGTTACC GGATAAGGCG CAGCGGTCGG GCTGAACGGG
      ATGGCCCAAC CTGAGTTCTG CTATCAATGG CCTATTCCGC GTCGCCAGCC CGACTTGCCC

5281  GGGTTCGTGC ACACAGCCCA GCTTGGAGCG AACGACCTAC ACCGAACTGA GATACCTACA
      CCCAAGCACG TGTGTCGGGT CGAACCTCGC TTGCTGGATG TGGCTTGACT CTATGGATGT

5341  GCGTGAGCTA TGAGAAAGCG CCACGCTTCC CGAAGGGAGA AAGGCGGACA GGTATCCGGT
      CGCACTCGAT ACTCTTTCGC GGTGCGAAGG GCTTCCCTCT TTCCGCCTGT CCATAGGCCA

5401  AAGCGGCAGG GTCGGAACAG GAGAGCGCAC GAGGGAGCTT CCAGGGGGAA ACGCCTGGTA
      TTCGCCGTCC CAGCCTTGTC CTCTCGCGTG CTCCCTCGAA GGTCCCCCTT TGCGGACCAT

5461  TCTTTATAGT CCTGTCGGGT TTCGCCACCT CTGACTTGAG CGTCGATTTT TGTGATGCTC
      AGAAATATCA GGACAGCCCA AAGCGGTGGA GACTGAACTC GCAGCTAAAA ACACTACGAG

5521  GTCAGGGGGG CGGAGCCTAT GGAAAAACGC CAGCAACGCG GCCTTTTTAC GGTTCCTGGC
      CAGTCCCCCC GCCTCGGATA CCTTTTTGCG GTCGTTGCGC CGGAAAAATG CCAAGGACCG
```

FIG. 17G

```
5581  CTTTTGCTGG CCTTTTGCTC ACATGTTCTT TCCTGCGTTA TCCCCTGATT CTGTGGATAA
      GAAAACGACC GGAAAACGAG TGTACAAGAA AGGACGCAAT AGGGGACTAA GACACCTATT

5641  CCGTATTACC GCCTTTGAGT GAGCTGATAC CGCTCGCCGC AGCCGAACGA CCGAGCGCAG
      GGCATAATGG CGGAAACTCA CTCGACTATG GCGAGCGGCG TCGGCTTGCT GGCTCGCGTC

5701  CGAGTCAGTG AGCGAGGAAG CGGAAGAGCG CCTGATGCGG TATTTTCTCC TTACGCATCT
      GCTCAGTCAC TCGCTCCTTC GCCTTCTCGC GGACTACGCC ATAAAAGAGG AATGCGTAGA

5761  GTGCGGTATT TCACACCGCA TATGGTGCAC TCTCAGTACA ATCTGCTCTG ATGCCGCATA
      CACGCCATAA AGTGTGGCGT ATACCACGTG AGAGTCATGT TAGACGAGAC TACGGCGTAT

5821  GTTAAGCCAG TATACACTCC GCTATCGCTA CGTGACTGGG TCATGGCTGC GCCCCGACAC
      CAATTCGGTC ATATGTGAGG CGATAGCGAT GCACTGACCC AGTACCGACG CGGGGCTGTG

5881  CCGCCAACAC CCGCTGACGC GCCCTGACGG GCTTGTCTGC TCCCGGCATC CGCTTACAGA
      GGCGGTTGTG GGCGACTGCG CGGGACTGCC CGAACAGACG AGGGCCGTAG GCGAATGTCT

5941  CAAGCTGTGA CCGTCTCCGG GAGCTGCATG TGTCAGAGGT TTTCACCGTC ATCACCGAAA
      GTTCGACACT GGCAGAGGCC CTCGACGTAC ACAGTCTCCA AAAGTGGCAG TAGTGGCTTT

6001  CGCGCGAGGC AGCTGCGGTA AAGCTCATCA GCGTGGTCGT GAAGCGATTC ACAGATGTCT
      GCGCGCTCCG TCGACGCCAT TTCGAGTAGT CGCACCAGCA CTTCGCTAAG TGTCTACAGA

6061  GCCTGTTCAT CCGCGTCCAG CTCGTTGAGT TTCTCCAGAA GCGTTAATGT CTGGCTTCTG
      CGGACAAGTA GGCGCAGGTC GAGCAACTCA AAGAGGTCTT CGCAATTACA GACCGAAGAC

6121  ATAAAGCGGG CCATGTTAAG GGCGGTTTTT TCCTGTTTGG TCACTTGATG CCTCCGTGTA
      TATTTCGCCC GGTACAATTC CCGCCAAAAA AGGACAAACC AGTGAACTAC GGAGGCACAT

6181  AGGGGGAATT TCTGTTCATG GGGGTAATGA TACCGATGAA ACGAGAGAGG ATGCTCACGA
      TCCCCCTTAA AGACAAGTAC CCCCATTACT ATGGCTACTT TGCTCTCTCC TACGAGTGCT

6241  TACGGGTTAC TGATGATGAA CATGCCCGGT TACTGGAACG TTGTGAGGGT AAACAACTGG
      ATGCCCAATG ACTACTACTT GTACGGGCCA ATGACCTTGC AACACTCCCA TTTGTTGACC

6301  CGGTATGGAT GCGGCGGGAC CAGAGAAAAA TCACTCAGGG TCAATGCCAG CGCTTCGTTA
      GCCATACCTA CGCCGCCCTG GTCTCTTTTT AGTGAGTCCC AGTTACGGTC GCGAAGCAAT
```

FIG. 17H

```
6361  ATACAGATGT AGGTGTTCCA CAGGGTAGCC AGCAGCATCC TGCGATGCAG ATCCGGAACA
      TATGTCTACA TCCACAAGGT GTCCCATCGG TCGTCGTAGG ACGCTACGTC TAGGCCTTGT

6421  TAATGGTGCA GGGCGCTGAC TTCCGCGTTT CCAGACTTTA CGAAACACGG AAACCGAAGA
      ATTACCACGT CCCGCGACTG AAGGCGCAAA GGTCTGAAAT GCTTTGTGCC TTTGGCTTCT

6481  CCATTCATGT TGTTGCTCAG GTCGCAGACG TTTTGCAGCA GCAGTCGCTT CACGTTCGCT
      GGTAAGTACA ACAACGAGTC CAGCGTCTGC AAAACGTCGT CGTCAGCGAA GTGCAAGCGA

6541  CGCGTATCGG TGATTCATTC TGCTAACCAG TAAGGCAACC CCGCCAGCCT AGCCGGGTCC
      GCGCATAGCC ACTAAGTAAG ACGATTGGTC ATTCCGTTGG GGCGGTCGGA TCGGCCCAGG

6501  TCAACGACAG GAGCACGATC ATGCGCACCC GTGGCCAGGA CCCAACGCTG CCCGAGATGC
      AGTTGCTGTC CTCGTGCTAG TACGCGTGGG CACCGGTCCT GGGTTGCGAC GGGCTCTACG

6561  GCCGCGTGCG GCTGCTGGAG ATGGCGGACG CGATGGATAT GTTCTGCCAA GGGTTGGTTT
      CGGCGCACGC CGACGACCTC TACCGCCTGC GCTACCTATA CAAGACGGTT CCCAACCAAA

6721  GCGCATTCAC AGTTCTCCGC AAGAATTGAT TGGCTCCAAT TCTTGGAGTG GTGAATCCGT
      CGCCGTAAGTG TCAAGAGGCG TTCTTAACTA ACCGAGGTTA AGAACCTCAC CACTTAGGCA

6781  TAGCGAGGTG CCGCCGGCTT CCATTCAGGT CGAGGTGGCC CGGCTCCATG CACCGCGACG
      ATCGCTCCAC GGCGGCCGAA GGTAAGTCCA GCTCCACCGG GCCGAGGTAC GTGGCGCTGC

6841  CAACGCGGGG AGGCAGACAA GGTATAGGGC GGCGCCTACA ATCCATGCCA ACCCGTTCCA
      GTTGCGCCCC TCCGTCTGTT CCATATCCCG CCGCGGATGT TAGGTACGGT TGGGCAAGGT

6901  TGTGCTCGCC GAGGCGGCAT AAATCGCCGT GACGATCAGC GGTCCAGTGA TCGAAGTTAG
      ACACGAGCGG CTCCGCCGTA TTTAGCGGCA CTGCTAGTCG CCAGGTCACT AGCTTCAATC

6961  GCTGGTAAGA GCCGCGAGCG ATCCTTGAAG CTGTCCCTGA TGGTCGTCAT CTACCTGCCT
      CGACCATTCT CGGCGCTCGC TAGGAACTTC GACAGGGACT ACCAGCAGTA GATGGACGGC

7021  GGACAGCATG GCCTGCAACG CGGGCATCCC GATGCCGCCC GAAGCGAGAA GAATCATAAT
      CCTGTCGTAC CGGACGTTGC GCCCGTAGGG CTACGGCGGC CTTCGCTCTT CTTAGTATTA

7081  GGGGAAGGCC ATCCAGCCTC GCGTCGCGAA CGCCAGCAAG ACGTAGCCCA GCGCGTCGGC
      CCCCTTCCGG TAGGTCGGAG CGCAGCGCTT GCGGTCGTTC TGCATCGGGT CGCGCAGCCG

7141  CGCCATGCCG GCGATAATGG CCTGCTTCTC GCCGAAACGT TGGTGGCGG GACCAGTGAC
      GCGGTACGGC CGCTATTACC GGACGAAGAG CGGCTTTGCA AACCACCGCC CTGGTCACTG
```

FIG. 17I

```
7201  GAAGGCTTGA GCGAGGGCGT GCAAGATTCC GAATACCGCA AGCGACAGGC CGATCATCGT
      CTTCCGAACT CGCTCCCGCA CGTTCTAAGG CTTATGGCGT TCGCTGTCCG GCTAGTAGCA

7261  CGCGCTCCAG CGAAAGCGGT CCTCGCCGAA AATGACCCAG AGCGCTGCCG GCACCTGTCC
      GCGCGAGGTC GCTTTCGCCA GGAGCGGCTT TTACTGGGTC TCGCGACGGC CGTGGACAGG

7321  TACGAGTTGC ATGATAAAGA AGACAGTCAT AAGTGCGGCG ACGATAGTCA TGCCCCGCGC
      ATGCTCAACG TACTATTTCT TCTGTCAGTA TTCACGCCGC TGCTATCAGT ACGGGGCGCG

7381  CCACCGGAAG GAGCTGACTG GGTTGAAGGC TCTCAAGGGC ATCGGTCGAC GCTCTCCCTT
      GGTGGCCTTC CTCGACTGAC CCAACTTCCG AGAGTTCCCG TAGCCAGCTG CGAGAGGGAA

7441  ATGCGACTCC TGCATTAGGA AGCAGCCCAG TAGTAGGTTG AGGCCGTTGA GCACCGCCGC
      TACGCTGAGG ACGTAATCCT TCGTCGGGTC ATCATCCAAC TCCGGCAACT CGTGGCGGCG

7501  CGCAAGGAAT GGTGCATGCA AGGAGATGGC GCCCAACAGT CCCCCGGCCA CGGGGCCTGC
      GCGTTCCTTA CCACGTACGT TCCTCTACCG CGGGTTGTCA GGGGGCCGGT GCCCCGGACG

7561  CACCATACCC ACGCCGAAAC AAGCGCTCAT GAGCCCGAAG TGGCGAGCCC GATCTTCCCC
      GTGGTATGGG TGCGGCTTTG TTCGCGAGTA CTCGGGCTTC ACCGCTCGGG CTAGAAGGGG

7621  ATCGGTGATG TCGGCGATAT AGGCGCCAGC AACCGCACCT GTGGCGCCGG TGATGCCGGC
      TAGCCACTAC AGCCGCTATA TCCGCGGTCG TTGGCGTGGA CACCGCGGCC ACTACGGCCG

7681  CACGATGCGT CCGGCGTAGA GCGCCACAGG ACGGGTGTGG TCGCCATGAT CGCGTAGTCG
      GTGCTACGCA GGCCGCATCT CGCGGTGTCC TGCCCACACC AGCGGTACTA GCGCATCAGC

7741  ATAGTGGCTC CAAGTAGCGA AGCGAGCAGG ACTGGGCGGC GGCCAAAGCG GTCGGACAGT
      TATCACCGAG GTTCATCGCT TCGCTCGTCC TGACCCGCCG CCGGTTTCGC CAGCCTGTCA

7801  GCTCCGAGAA CGGGTGCGCA TAGAAATTGC ATCAACGCAT ATAGCGCTAG CAGCACGCCA
      CGAGGCTCTT GCCCACGCGT ATCTTTAACG TAGTTGCGTA TATCGCGATC GTCGTGCGGT

7861  TAGTGACTGG CGATGCTGTC GGAATGGACG ATATCCCGCA AGAGGCCCGG CAGTACCGGC
      ATCACTGACC GCTACGACAG CCTTACCTGC TATAGGGCGT TCTCCGGGCC GTCATGGCCG

7921  ATAACCAAGC CTATGCCTAC AGCATCCAGG GTGACGGTGC CGAGGATGAC GATGAGCGCA
      TATTGGTTCG GATACGGATG TCGTAGGTCC CACTGCCACG GCTCCTACTG CTACTCGCGT

7981  TTGTTAGATT TCATACACGG TGCCTGACTG CGTTAGCAAT TTAACTGTGA TAAACTACCG
      AACAATCTAA AGTATGTGCC ACGGACTGAC GCAATCGTTA AATTGACACT ATTTGATGGC

7041  CATTA
      GTAAT
```

FIG. 17J

RETROVIRAL GENE THERAPY VECTORS AND THERAPEUTIC METHODS BASED THEREON

CROSS-REFERENCE TO RELATED APPLICATIONS

This application is a continuation-in-part of U.S. application Ser. No. 08/252,710, filed Jun. 2, 1994, which is a continuation-in-part of co-owned and U.S. application Ser. No. 07/786,015, and filed Oct. 31, 1991, now abandoned, which is a continuation-in-part of co-owned U.S. application Ser. No. 07/607,252, filed Oct. 31, 1990, now abandoned, and which is a continuation-in-part of co-owned U.S. application Ser. No. 07/131,926, filed Dec. 11, 1987, now abandoned, each of which applications are hereby incorporated by reference herein.

1. INTRODUCTION

The present invention is directed to gene therapy vectors and methods, and provides a family of novel recombinant retroviral vectors capable of efficiently transferring any gene of interest into a wide range of mammalian target cells. Cells transduced with the recombinant retroviral vectors of the invention are capable of expressing high levels of a desired gene product for long periods of time. Thus, such transduced cells may be useful in the treatment of a wide variety of diseases wherein permanently augmenting or adding the production of a given protein or other polypeptide is therapeutically desirable. Preferred vectors of the invention lacking selectable markers are described, and are particularly useful for somatic cell gene therapy in the treatment of diseases wherein the co-production of marker gene products, such as antibiotics, would be undesirable or unacceptable.

2. BACKGROUND OF THE INVENTION

Numerous methods exist for genetically engineering mammalian cells. There is great interest in genetically engineering mammalian cells for several reasons including the need to produce large quantities of various polypeptides and the need to correct various genetic defects in the cells. The methods differed dramatically from one another with respect to such factors as efficiency, level of expression of foreign genes, and the efficiency of the entire genetic engineering process.

One method of genetically engineering mammalian cells that has proven to be particularly useful is by means of retroviral vectors. Retrovirus vectors and their uses are described in many publications including Mann, et al., *Cell* 33:153–159 (1983) and Cone and Mulligan, *Proc. Natl. Acad. Sci. USA* 81:6349–6353 (1984). Retroviral vectors are produced by genetically manipulating retroviruses.

Retroviruses are RNA viruses; that is, the viral genome is RNA. This genomic RNA is, however, reverse transcribed into a DNA copy which is integrated stably and efficiently into the chromosomal DNA of transduced cells. This stably integrated DNA copy is referred to as a provirus and is inherited by daughter cells as any other gene. As shown in FIG. 1, the wild type retroviral genome and the proviral DNA have three Psi genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAS.

Adjacent to the 5' LTR are sequences necessary for reverse transcription of the genome (the TRNA primer binding site) and for efficient encapsidation of viral RNA into particles (the Psi site). Mulligan, R. C., In: *Experimental Manipulation of Gene Expression*, M. Inouye (ed), 155–173 (1983); Mann, R., et al., *Cell*, 33:153–159 (1983); Cone, R. D. and R. C. Mulligan, *Proceedings of the National Academy of Sciences*, U.S.A., 81:6349–6353 (1984).

If the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Mulligan and coworkers have described retroviral genomes from which these Psi sequences have been deleted, as well as cell lines containing the mutant genome stably integrated into the chromosome. Mulligan, R. C., In *Experimental Manipulation of Gene Expression*, M. Inouye (ed), 155–173 (1983); Mann, R., et al., *Cell*, 33:153–159 (1983); Cone, R. D. and R. C. Mulligan, *Proceedings of the National Academy of Sciences*, U.S.A., 81:6349–6353 (1984). Additional details on available retrovirus vectors and their uses can be found in patents and patent publications including European Patent Application EPA 0 178 220, U.S. Pat. No. 4,405,712, Gilboa, *Biotechniques* 4:504–512 (1986) (which describes the $N_2$ retroviral vector) The teachings of these patents and publications are incorporated herein by reference.

Retroviral vectors are particularly useful for modifying mammalian cells because of the high efficiency with which the retroviral vectors "infect" target cells and integrate into the target cell genome. Additionally, retroviral vectors are highly useful because the vectors may be based on retroviruses that are capable of infecting mammalian cells from a wide variety of species and tissues.

The ability of retroviral vectors to insert into the genome of mammalian cells have made them particularly promising candidates for use in the genetic therapy of genetic diseases in humans and animals. Genetic therapy typically involves (1) adding new genetic material to patient cell in vivo, or (2) removing patient cells from the body, adding new genetic material to the cells and reintroducing them into the body, i.e., in vitro gene therapy. Discussions of how to perform gene therapy in a variety of cells using retroviral vectors can be found, for example, in U.S. Pat. Nos. 4,868,116, issued Sep. 19, 1989, and 4,980,286, issued Dec. 25, 1990 (epithelial cells), WO89/07136 published Aug. 10, 1989 (hepatocyte cells), EP 378,576 published Jul. 25, 1990 (fibroblast cells), and WO89/05345 published Jun. 15, 1989 and WO/90/06997, published Jun. 28, 1990 (endothelial cells), the disclosures of which are incorporated herein by reference.

In order to be useful for the various techniques of gene therapy, suitable retroviral vectors require special characteristics that have not hitherto been available. A primary source of the need for these special requirements of the vector for use in the in vivo genetic manipulation of patient cells in gene therapy is because it is usually not feasible to use retroviral vectors that require a selection for integration of the vector into the genome of "patient" cells. For example, typical retroviral vectors, e.g., MSV DHFR-NEO described in Williams, et al., *Nature* 310:476–480 (1984), uses neomycin resistance as a suitable marker for detecting genetically modified cells. Thus, with such neomycin resistant retroviral vectors, patients would be required to be exposed to high levels of neomycin in order to effect genetic repair of cells through in vivo gene therapy. Moreover, in both in vivo and in vitro gene therapy it may be undesirable to produce the gene product of the marker gene in cells undergoing human gene somatic therapy. For example, there is no therapeutic reason to produce large levels of neomycin phosphotransferase in blood cells undergoing hemoglobin gene replacement for curing a thalassemia. Therefore, it would be desirable to develop retroviral vectors that integrate efficiently into the genome, express desired levels of the gene product of interest, and are produced in high titers without the coproduction or expression of marker products such as antibiotic resistance factors.

Despite considerable progress in efforts to develop effective genetic therapies for diseases involving hematopoietic cells, a number of significant technical hurdles remain. First, while a variety of transduction protocols have been developed which make it possible to efficiently transfer genes into murine hematopoietic stem cells, it has not yet been possible to achieve efficient gene transfer into reconstituting cells of large animals. It is currently unclear to what extent this problem is vector related (e.g. insufficient titers, host range) or a consequence of a lack of knowledge regarding the optimal conditions for obtaining the proliferation and/or efficient engraftment of appropriate target cells. A second important technical stumbling block relates to the development of retroviral vectors possessing the appropriate signals for obtaining high level constitutive expression of inserted genes in hematopoietic cells in vivo. Although a number of groups have demonstrated the expression of genes in mice reconstituted with transduced bone marrow cells, others have experienced difficulties (10–12). Overall, few general principles regarding features of vector design important for gene expression in vivo have emerged. In particular, because of differences in vector backbones, inserted genes, viral titers, transduction protocols, and other experimental parameters, it has been impossible to directly compare the performance of different vectors and to determine the features of vector design which most critically affect gene expression in hematopoietic cells in vivo. In addition, few studies have examined the ability of transferred genes to be expressed for very long periods of time (e.g. the lifetime of the transplant recipients), a clearly important goal of gene therapy for diseases involving hematopoietic cells.

3. SUMMARY OF THE INVENTION

The present invention is directed to a family of novel retroviral vectors capable of being used in somatic gene therapy. The retroviral vectors of the invention include an insertion site for a gene of interest and are capable of expressing desired levels of the encoded protein in a wide variety of transfected cell types.

In one aspect of the invention there is provided a retroviral vector comprising in operable combination, a 5' LTR and a 3' LTR derived from a retrovirus of interest, and an insertion site for a gene of interest, and wherein at least one of the gag, env or pol genes in the vector are incomplete or defective. The vector preferably contains a splice donor site and a splice acceptor site, wherein the splice acceptor site is located upstream from the site where the gene of interest is inserted. Also, the vector desirably contains a gag transcriptional promoter functionally positioned such that a transcript of a nucleotide sequence inserted into the insertion site is produced, and wherein the transcript comprises the gag 5' untranslated region. The preferred vectors of the invention are lacking a selectable marker, thus, rendering them more desirable in human somatic gene therapy because a marker gene product, such as an antibiotic drug marker, will not be co-produced or co-expressed.

The gene of interest that is incorporated in the vectors of the invention may be any gene which produces a hormone, an enzyme, a receptor or a drug(s) of interest.

The retroviral vectors are most suitably used in combination with certain packaging cells, as herein defined, which in turn may be used in a wide variety of cell types for human or animal somatic gene therapy.

A particular preferred retroviral vector of the invention is identified herein as "MFG", as depicted in FIGS. 2c and 3, and the plasmid containing it, and especially the plasmid MFG having the identifying characteristics of ATCC No. 68,754.

The present invention is also directed to retroviral vectors similar to those described above, but further comprising a non-LTR enhancer and the alpha-globin transcriptional promoter sequence in order to control the expression of various genes of interest. This aspect of the invention specifically provides for the use of an enhancer sequence from cytomegalovirus. Also provided are vectors in which the enhancer sequence is deleted from the 3' LTR thus resulting in the inactivation of the 5' LTR upon integration of the vector into the genome. The α-globin promoter containing vector α-SGC is specifically provided, and especially that which is depicted in FIG. 4, and the plasmid containing it, and especially the plasmid α-SGC having the identifying characteristics of ATCC No. 68,755.

4. BRIEF DESCRIPTION OF THE FIGURES

FIG. 1 is a schematic representation of a wild type murine leukemia virus (retroviral) genome.

FIGS. 2A–D is a schematic representation of retroviral vectors, each having a recombinant genome, useful in the present invention. FIG. 2a is pLJ and FIG. 2b is pEm, FIG. 2c is MFG and FIG. 2D is α-SGC.

Figure 6A:
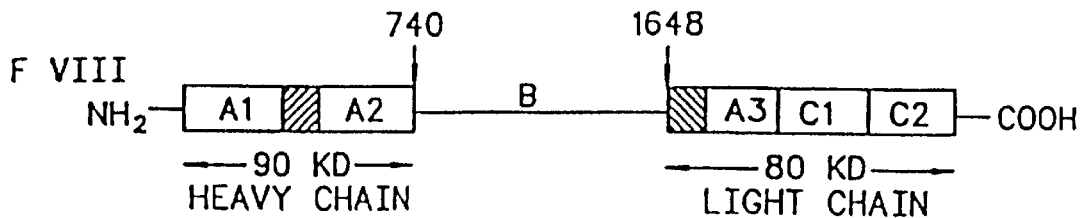
Figure 6B:
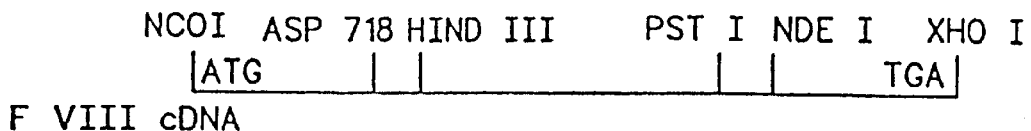
Figure 6C:
Figure 6D:
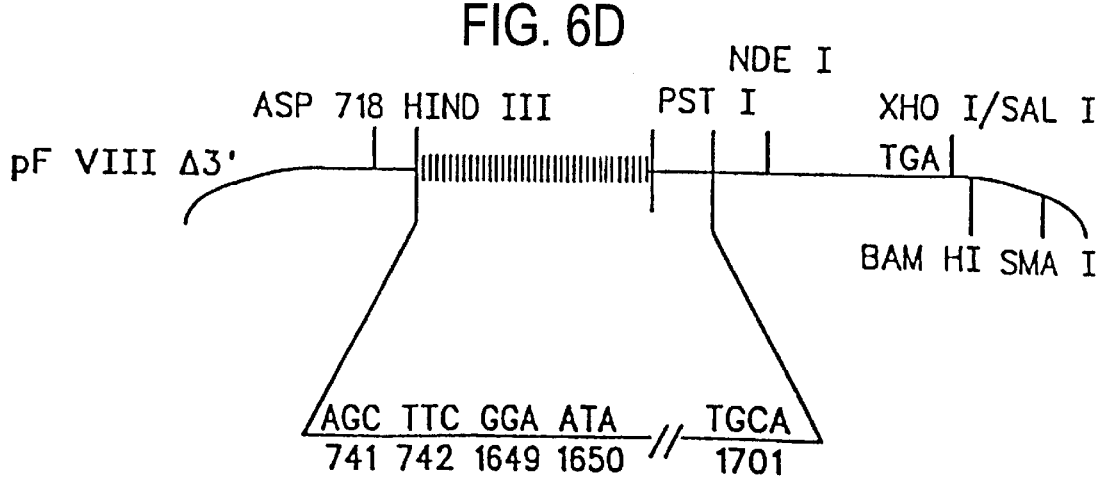

FIGS. 6A–D is a diagram of the factor VIII polypeptide. FIG. 6b is a diagram of the factor VIII cDNA showing the restriction enzyme sites used in the various constructs to generate the retroviral vector. FIG. 6c is a diagram of the deletion derivative of the factor VIII cDNA inserted into the retroviral vector with the deleted region shown as vertical lines. FIG. 6d is an expanded diagram of the B domain deletion between the Hind III and Pst I sites. The nucleotide sequence at the junction of the heavy chain and light chain is denoted above the line and the corresponding amino acid numbers are denoted below the line.

Figure 7:
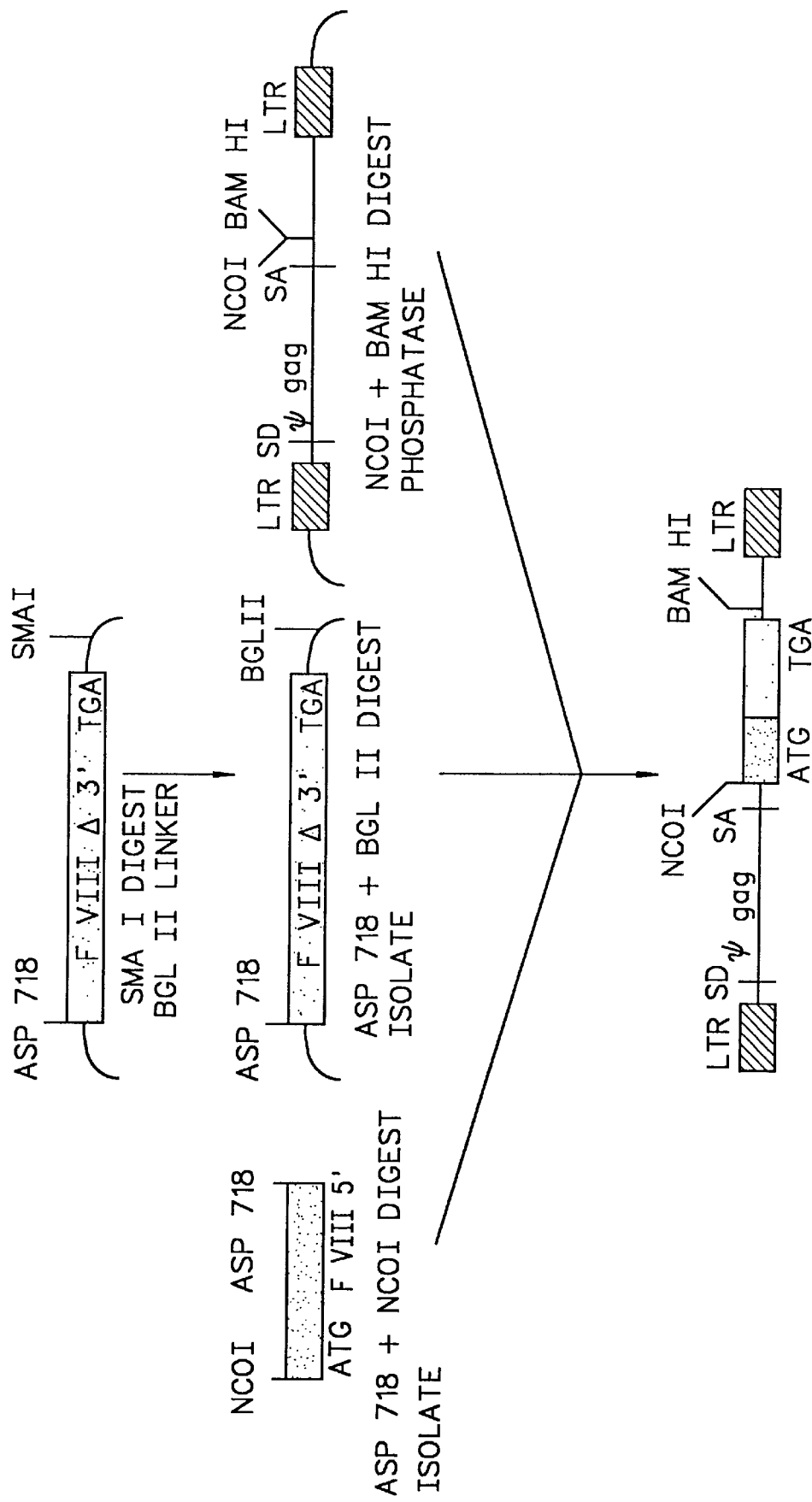

FIG. 7 is a diagram of the assembled final retroviral vector, MFG-factor VIII.

Figure 8:
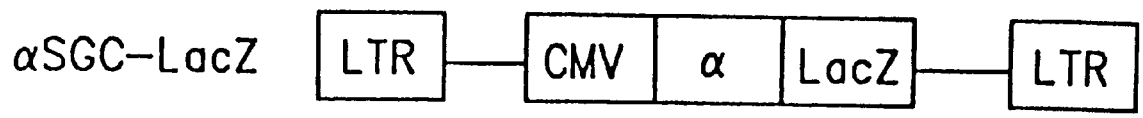

FIG. 8 is a diagram of the α-SGC-LacZ recombinant retrovirus.

Figure 9A:
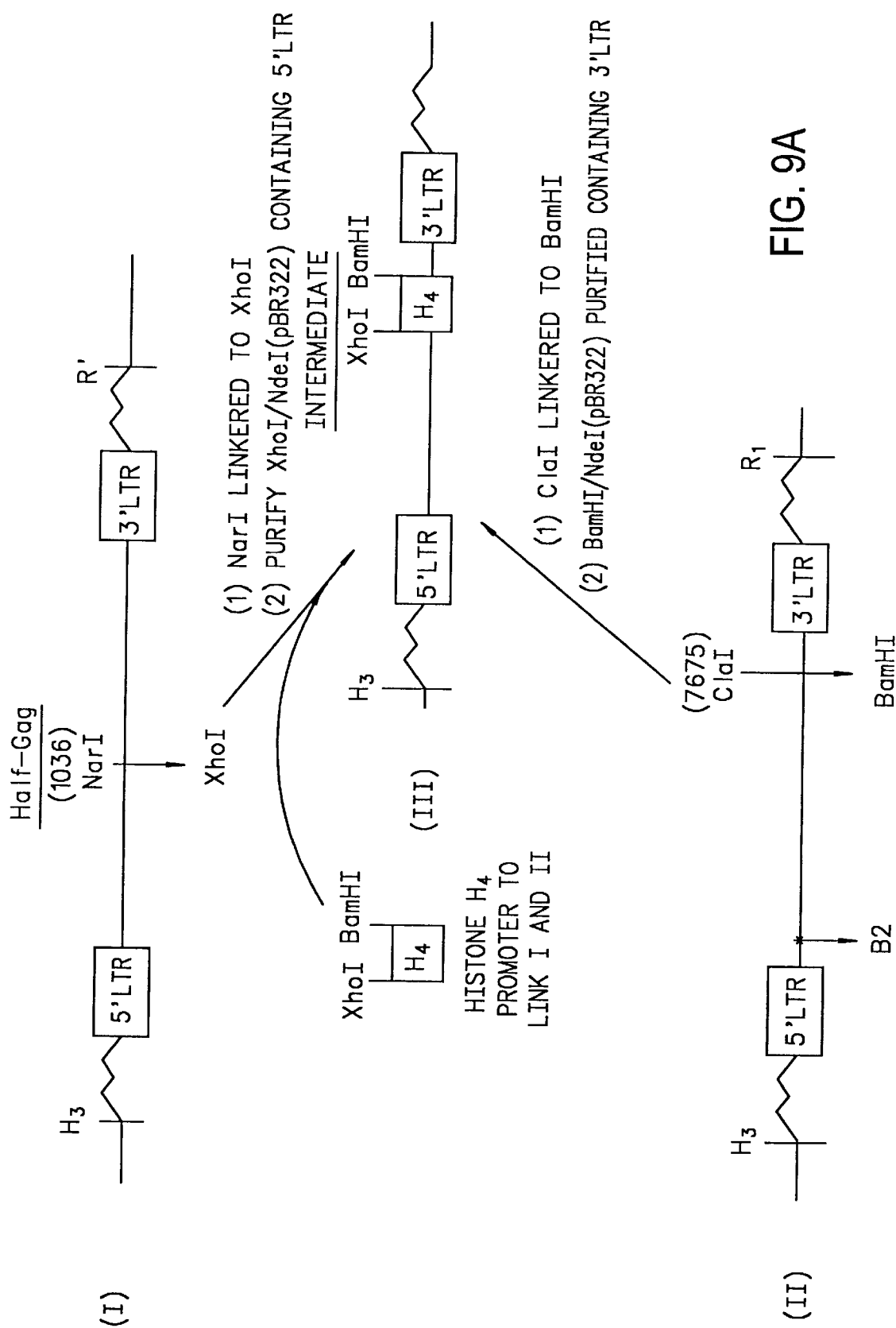
Figure 9B:
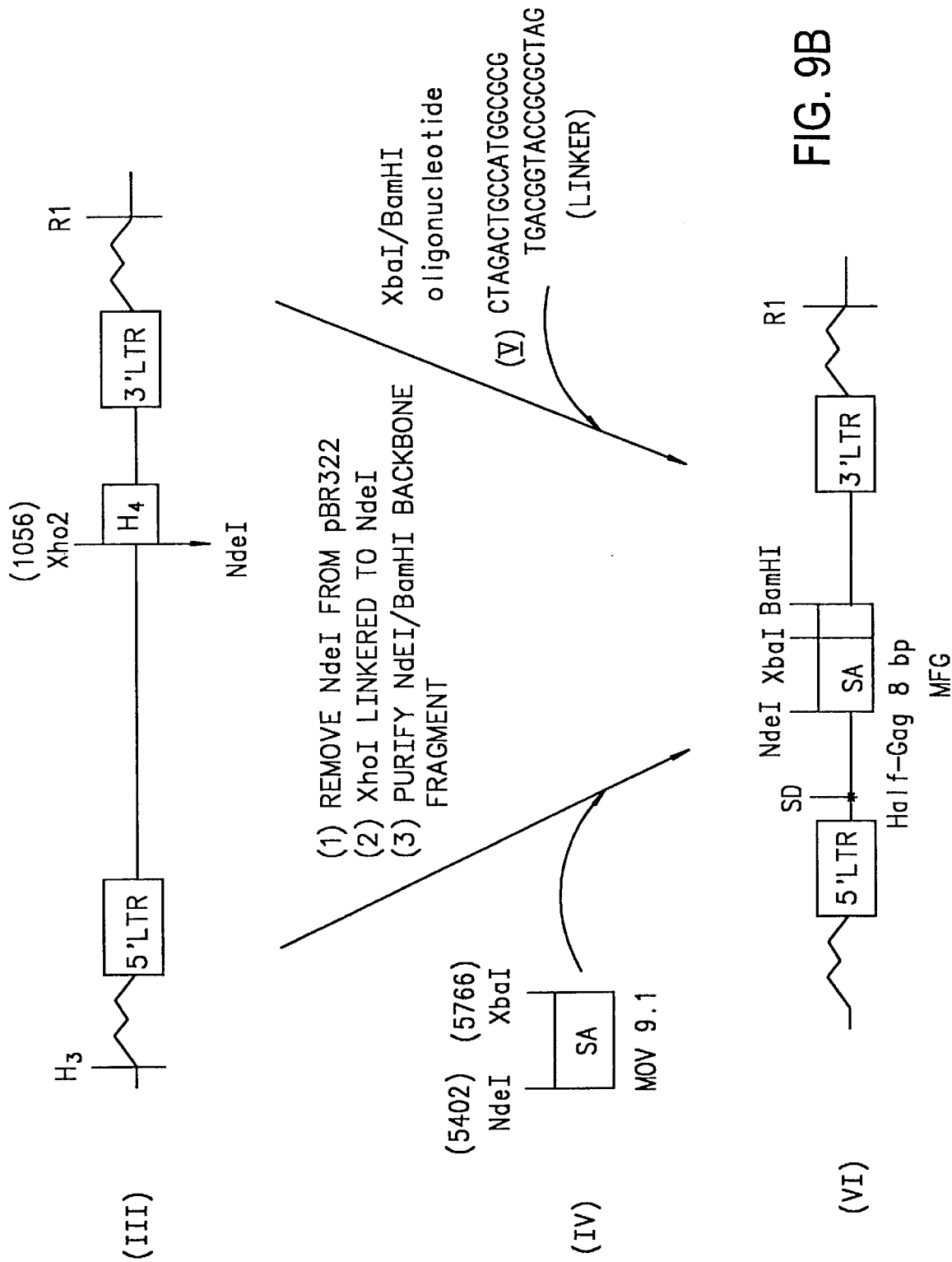

FIGS. 9(a) and 9(b) represents a schematic diagram of the construction of the MFG vector of the invention.

Figure 10:
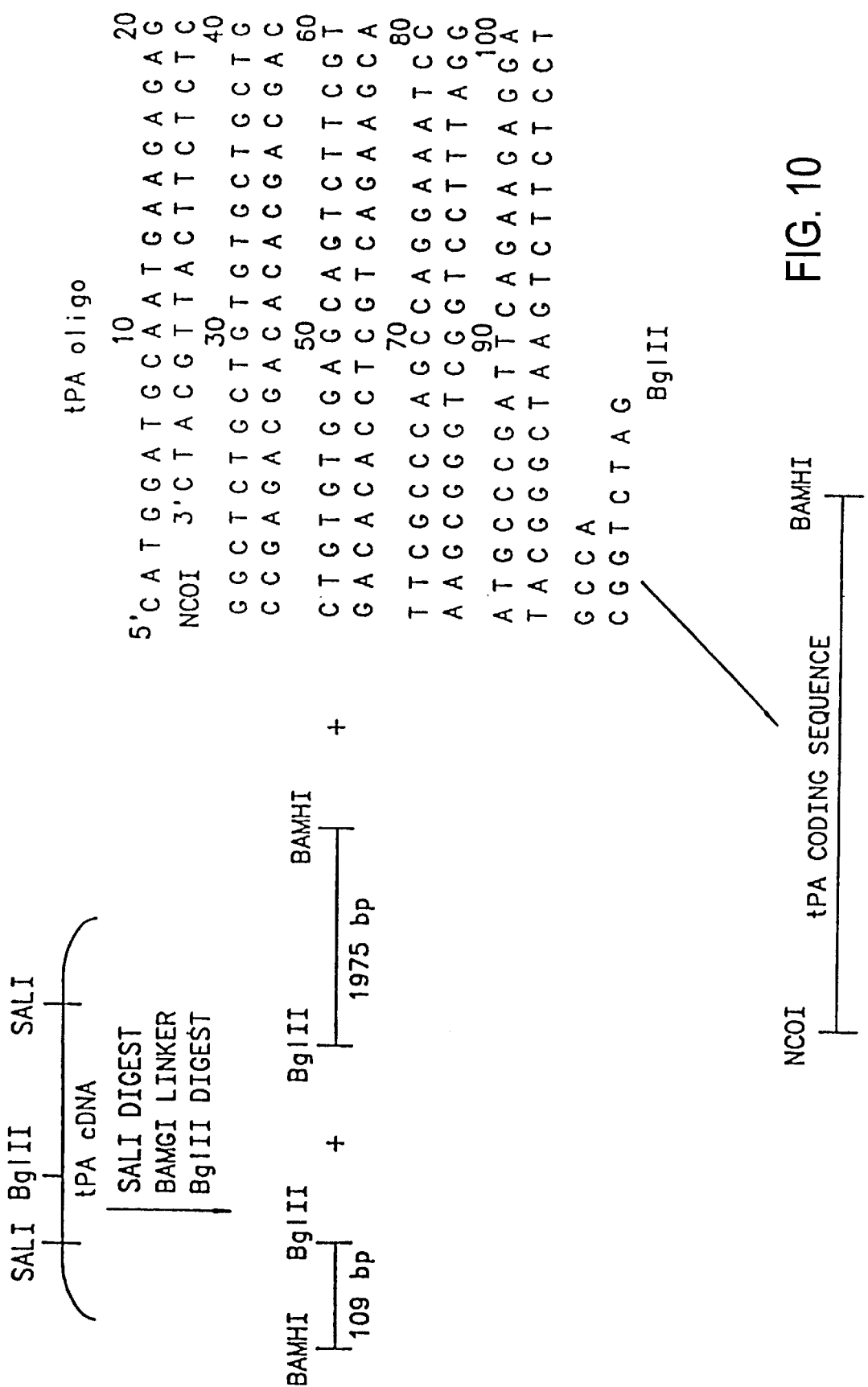

FIG. 10 is a schematic representation of the modification of the tPA gene, the oligonucleotides used to facilitate the modification and the insertion of the modified tPA gene into the MFG vector.

Figure 11A:
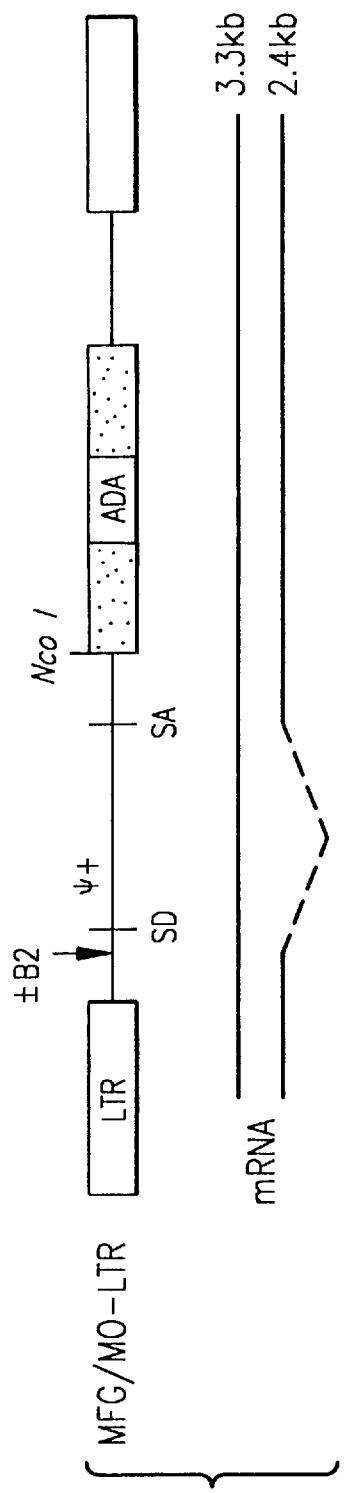
Figure 11B:
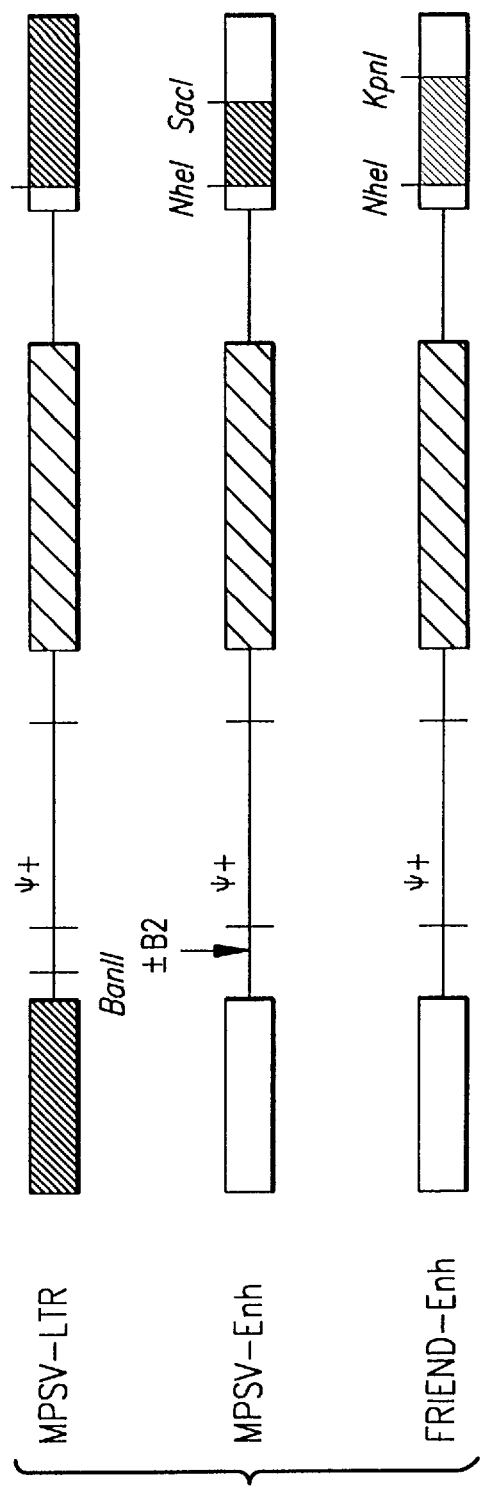
Figure 11C:
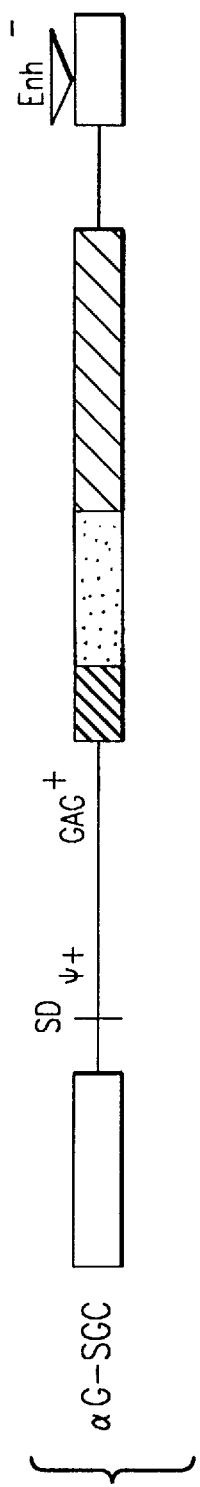

FIGS. 11A–C. Structure of retroviral vectors encoding human adenosine deaminase (huADA).

(A) MFG-derived recombinant retroviruses. The MFG vector is derived from Mo-MuLV. The 5'-region extends to the Nar I site at position 1035 thus retaining the ψ element, Mann R. et al., *Cell*, 33:153–159, (1983), the splice donor (SD) and some gag coding sequence. The start codon of gag has been mutated by insertion of a Sma I linker. The 5' fragment is linked to the Nde I (+5401)- Nla III (+5780) fragment that contains the splice acceptor (SA) necessary for the generation of the env mRNA. A point mutation (A- C) has converted the Nla III site into an Nco I site encompassing the env initiation codon where the human ADA coding sequence was inserted (from Nco I +74 to Acc I +1324 within the huADA cDNA (□). Daddona, P. E., et al., *J. Biol. Chem.* 259:12101–12106, (1984). The Mo-LTR/B2 vector was constructed by ligating the 1274 bp Hind III-Pvu I fragment of the PEM-ADA vector, Wilson, J. M. et al., *Proc. Natl. Acad. Sci. USA* 87:439–443, ((1990), that contains the B2 mutation (G to A at position +160) to the Hind III-Pvu I fragment of MFG. The MPSV enhancer was cloned into MFG by replacing the Nhe I-Sac I fragment of the 3' Mo-MULV LTR with the 385 bp corresponding fragment from the 3' MPSV-LTR plasmid (kindly provided by P. Robbins, Pittsburgh, Pa.) to generate the MPSV-Enh construct. The MPSVE-EnhB2 was analogously derived from MPSV-Enh and PEM-ADA constructs. In the MPSV-LTR construct, the 6014 bp Ban II-Nhe I fragment from the pC663neoR plasmid, Ostertag, W., et al., *J. gen. Virol.* 67:1361–1371, (1986), has been replaced with the 2694 bp Ban II-Nhe I fragment from the MFG vector. To generate the Fr-Enh construct, the 450 bp Nhe I-Kpn I fragment of MFG was replaced with the corresponding Nhe I-Kpn I fragment from the pFr-SV (X) plasmid, Holland, et al., *Proc. Natl. Acad. Sci., USA*, 84:8662–8666, (1987). Mo-MuLV LTR (□), MPSV sequences (□) Friend sequences (□).

(B) αG-SGC vector: The αG-SGC vector derived from PHSG, bears a portion of gag and an enhancer deletion in the 3' LTR, Guild, et al., *J. Virol.*, 62:3795–3801, (1988). In this vector, huADA expression is under the control of the human cytomegalovirus (CMV) enhancer (□) (SpeI +154-Nco I +515 fragment), Boshart, M. et al., *Cell*, 41:521–530, (1985), and α-globin promoter (□) (Pst 1 -570 -NcoI +37 fragment), Braelle, F. E., *Cell*, 12:1085–1095, (1977).

(C) DNA analysis of NIH 3T3 cells infected with the recombinant retroviruses: After infection of NIH 3T3 cells under standard conditions (see Section 11.1, infra), genomic DNA was digested with Nhe I and analyzed by Southern blot using a huADA cDNA probe. Each lane was loaded with 10 μg of genomic DNA. The number of proviral copy per cell is indicated under each lane as determined with the Phosphorimager. In the left lane, the copy control correspond to 1 copy per cell of the Mo-LTR vector.

Figures 12A, 12B:
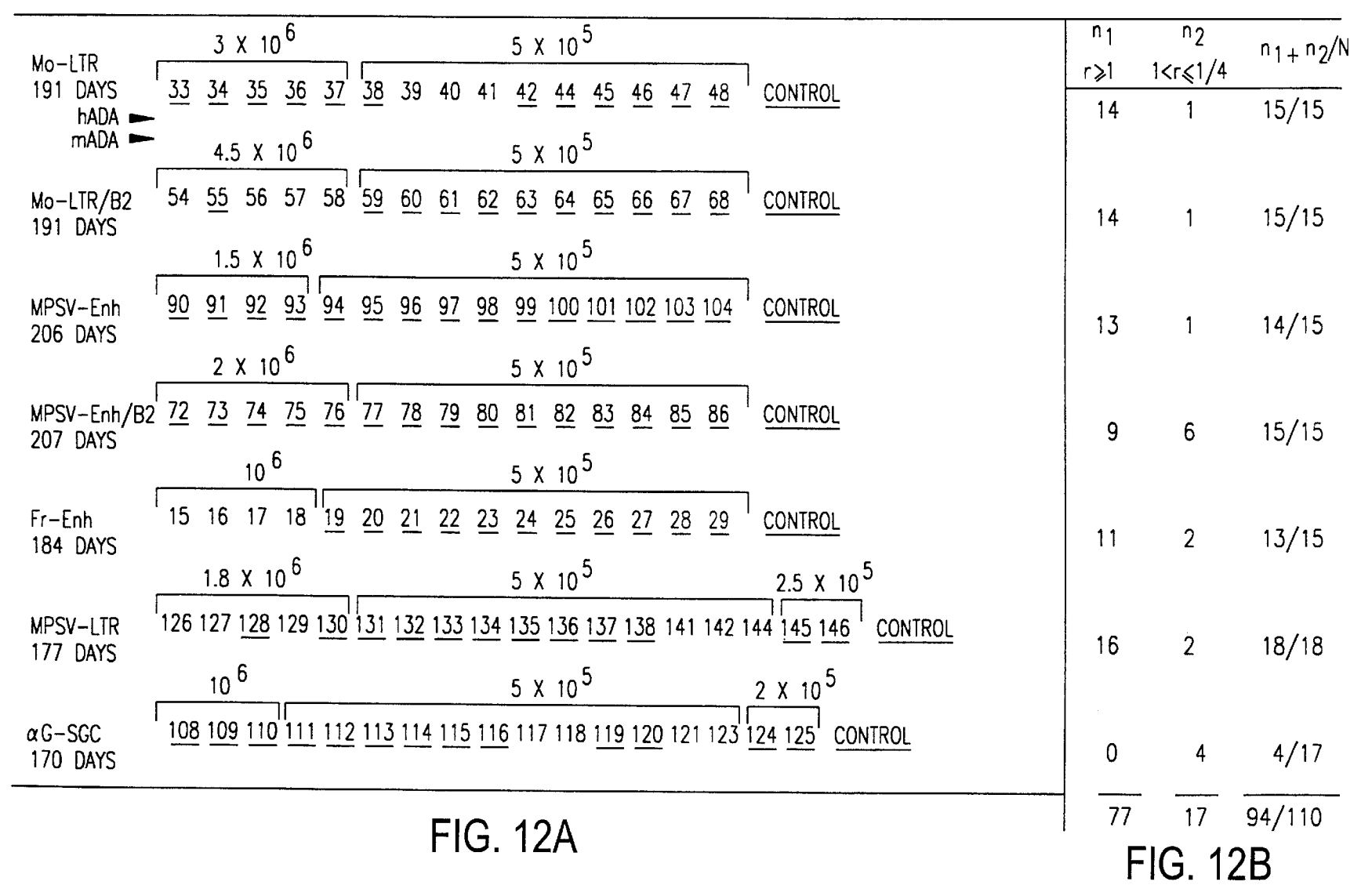

FIGS. 12A–C. Analysis of human ADA expression in peripheral blood cells:

(A) Analysis of hADA expression 5–7 months after BMT. The time at which blood samples were drawn is indicated in days after transplantation for each vector. hADA activity was measured by IEF (see Section 11.1., infra) . The number directly above each sample indicates individual animals. The number of cells injected in every recipient is indicated above and extends from 2'×10$^5$ to 4.5×10$^6$ cells. The lower band on the gel represents the activity of the murine endogenous ADA (MADA) and the upper band represents the human ADA (huADA) activity control samples were prepared from non-transplanted mice. The italic numbers indicate the mice which were examined in detail in FIG. 13.

(B) Fraction of mice expressing huADA at 5–7 months after BMT. Relative ADA activity (r) represents the ratio of the intensity of human to mouse ADA enzyme bands determined on FIG. 12A: with the computer densitometer. $n_1$ indicates the number of mice in which r>1 and $n_2$ the number of mice in which 1<r≦¼: N represents the total number of mice analyzed.

(C) Comparison of human ADA expression in PBC 5–7 and 12–14 months after BMT. Blood samples were drawn at two distant time points after transplantation as indicated by the arrow and analyzed for ADA activity as described in FIG. 12A. Individual mice are designated by their number (#). Arrows indicate mADA and huADA activity. The relative ADA activity indicated under each sample is determined as the ratio of the intensity of the human to mouse enzyme bands. The percentage indicated in the first column represents, for each vector, the mean hADA activity 12–14 months after BMT compared to the original activity (100%) measured 5–7 months after BMT. (n) represents the number of mice used to calculate the mean activity.

FIGS. 13A–D. Quantification of huADA expression in hematopoietic cell fractions 12–14 months after BMT.

(A) Analysis of huADA activity in hematopoietic cell fractions of individual mice. The animals, designated by their number, were sacrificed, cell fractions were harvested and huADA activity determined by IEF in each fraction[a]. The enzymatic activity is reported in arbitrary units expressed per proviral copy per μg total protein. "O"=no detectable huADA activity; "nd"=not determined.

[a] BM, unfractionated bone marrow; Spleen, unfractionated spleen; B Lymph, splenic B lymphocytes; T Lymph, splenic T lymphocytes; Mac, macrophages derived from BM.

(B) Average human activity per proviral copy per μg total protein. The average huADA activity is presented for every recombinant vector in every fraction[a]. The statistical significance of the normalized differences of huADA activity between Mo-LTR and each of the other vectors is indicated as described[b].

[a] BM, unfractionated bone marrow; Spleen, unfractionated spleen; B Lymph, splenic B lymphocytes; T Lymph, splenic T lymphocytes; Mac, macrophages derived from BM.

[b] Each bar marked with an asterisk (*) indicates that a distribution made of 1) pooled BM and spleen samples; 2) B lymphotcytes; 3) T lymphocytes; 4) macrophages shows statistically significant difference (P<0.05) when compared to the corresponding "Mo-LTR distribution" (Student-Fischer's t test).

(C) Average proviral copy number per cell. DNA was isolated from each cell fraction of all animals and analyzed by the method of Southern using a huADA probe. For each sample, the exact copy number was determined using the Phosphorimager, taking as a reference a cell clone known to have one copy per cell. The average proviral copy number per cell and the statistical analyses[b] are presented for every recombinant vector in each cell fraction[a].

[b] Each bar marked with an asterisk (*) indicates that a distribution made of 1) pooled BM and spleen samples; 2) B lymphotcytes; 3) T lymphocytes; 4) macrophages shows statistically significant difference (P<0.05) when compared to the corresponding "Mo-LTR distribution" (Student-Fischer's t test).

(D) Average human ADA activity per μg total protein. The average hADA activity was determined for each vector independently of the proviral copy number. The significance of the differences of hADA activity between Mo-LTR and each of the other vectors is indicated.

Figure 13A:
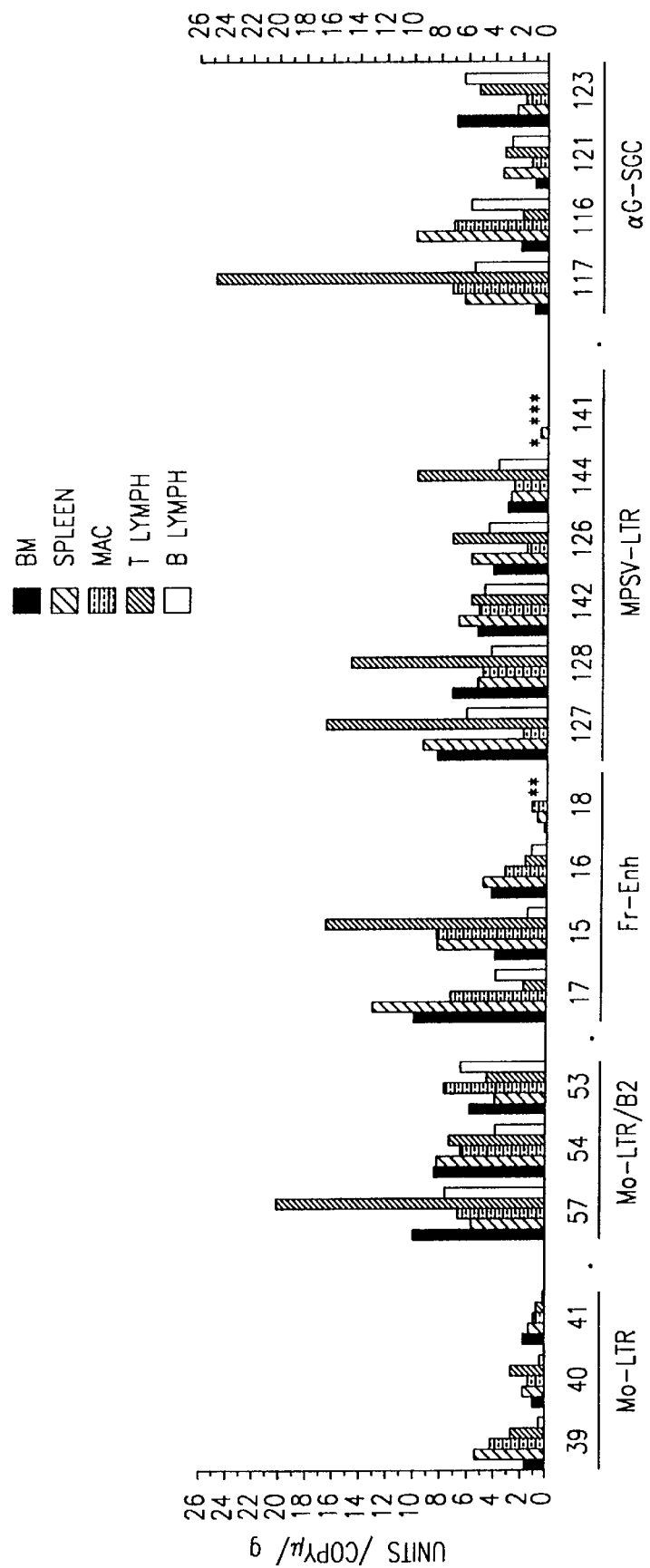
Figure 13B:
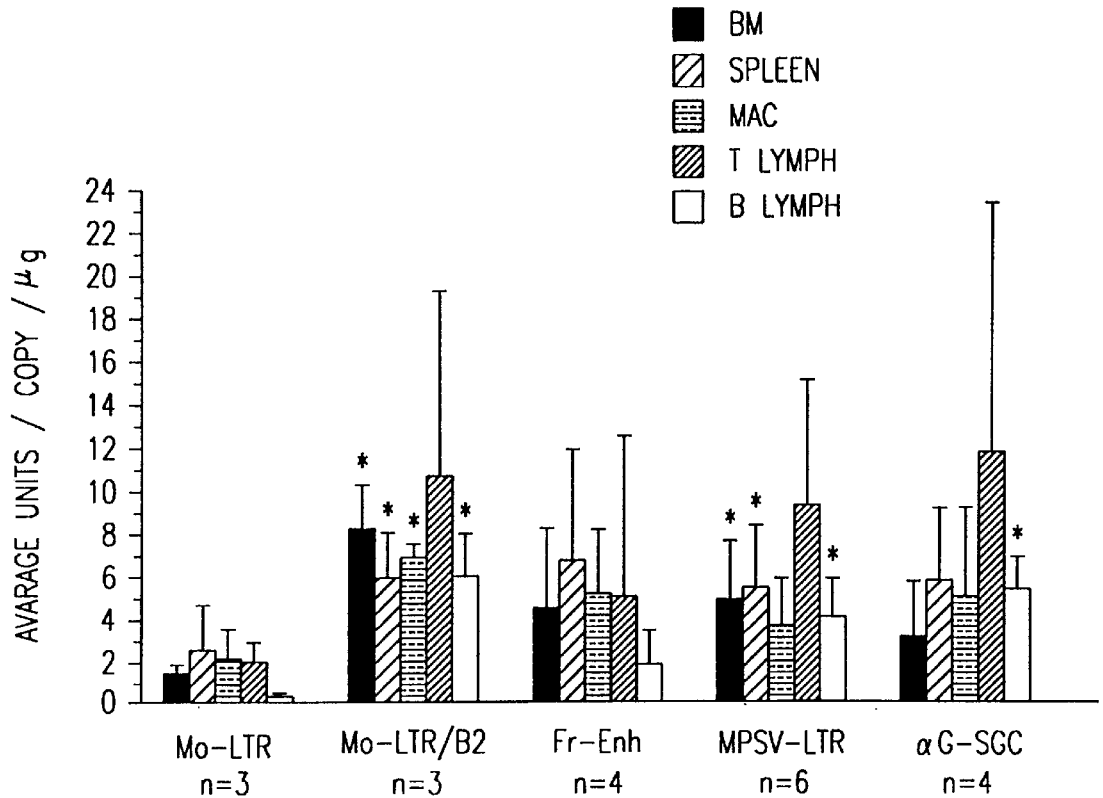
Figure 13C:
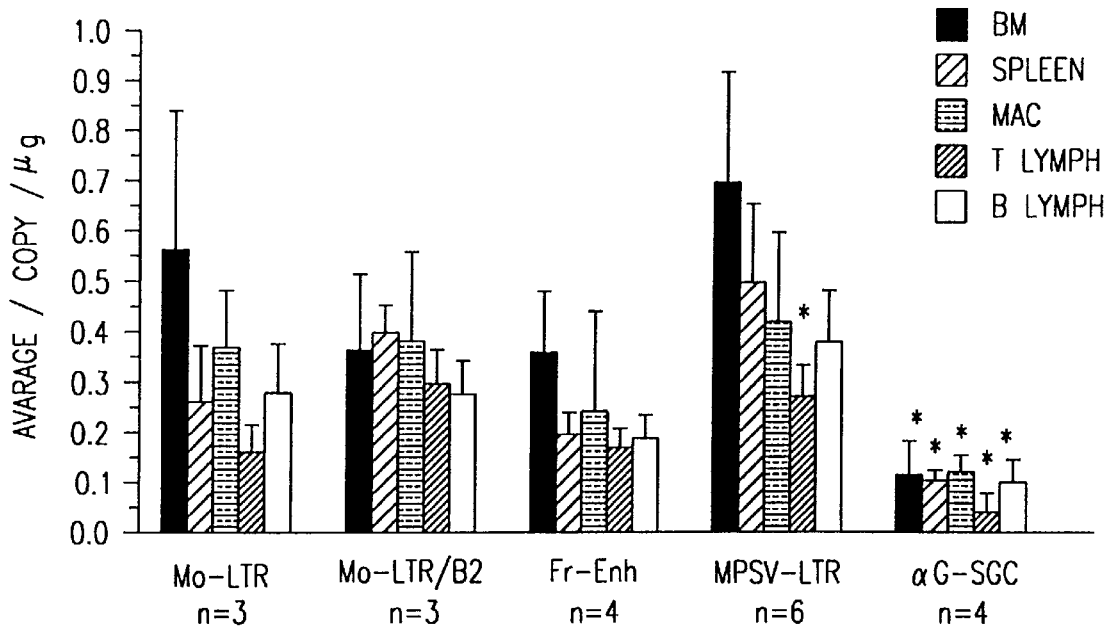
Figure 13D:
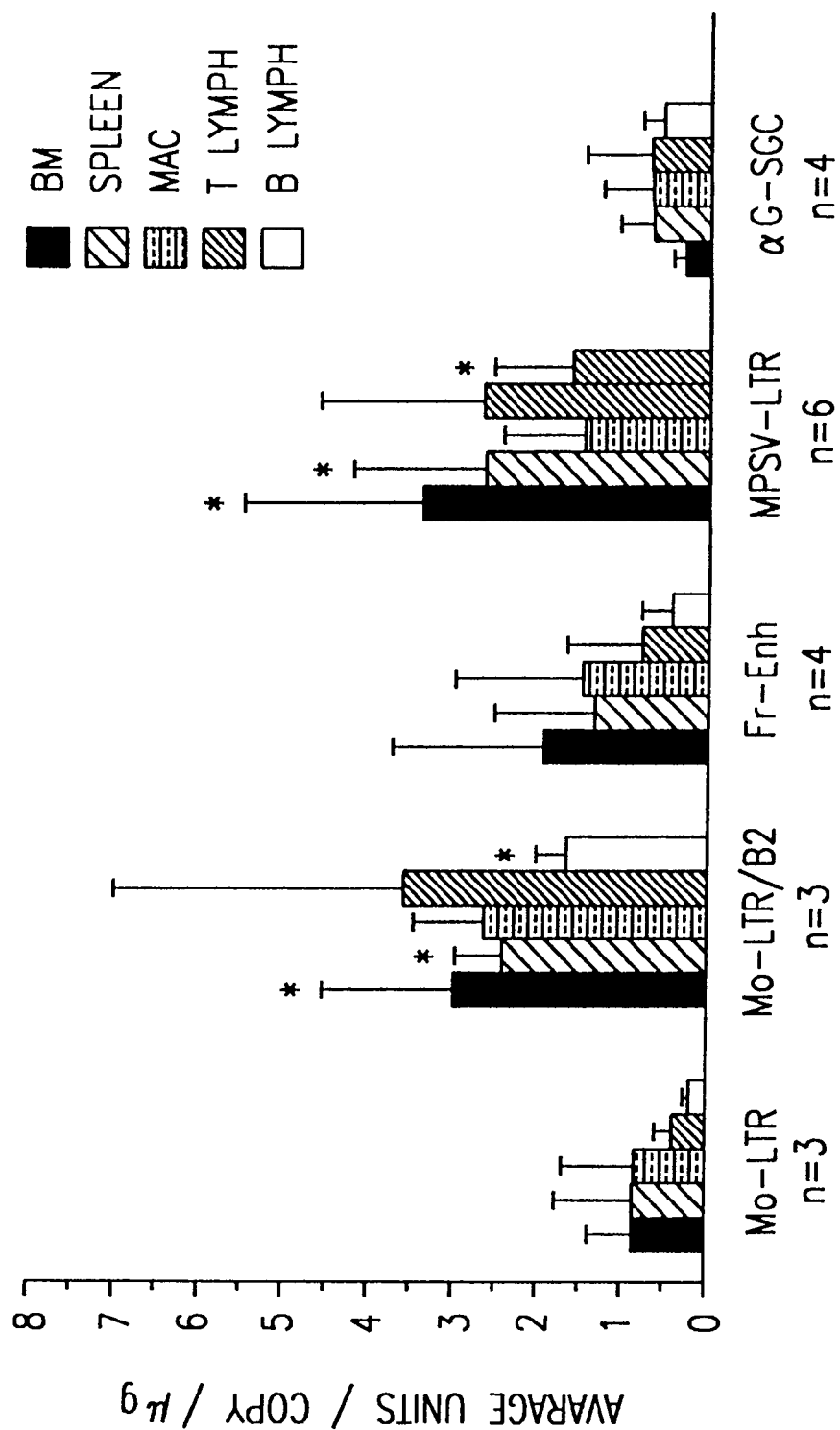

The number of mice (n) used to calculate the means ±SD is indicated under each vector and is derived from the mice analyzed in detail in FIG. 13A.

FIG. 14 provides a comparison of the DNA sequences for the Moloney murine leukemia virus ("MoMuLV") (SEQ ID NO:5), the MFG vector (SEQ ID NO:6) and the MFG-S vector (SEQ ID NO:7). Nucleotides 320–643 of MoMuLV are shown at the top of each line. The putative CTG start codons for the cell surface gag protein and the ATG start codon for the cytoplasmic gag proteins are in enlarged letters. The gag open reading frames are denoted by underline. 'X' indicates that the nucleotide is unchanged, and a '−' indicates that a nucleotide has been deleted. The nucleotide substitutions which differentiate MFG and MFG-S are indicated by boxing. Both MFG and MFG-S have a linker insertion following the ATG of the gag ORF which is not present in MoMuLV.

Figure 15:
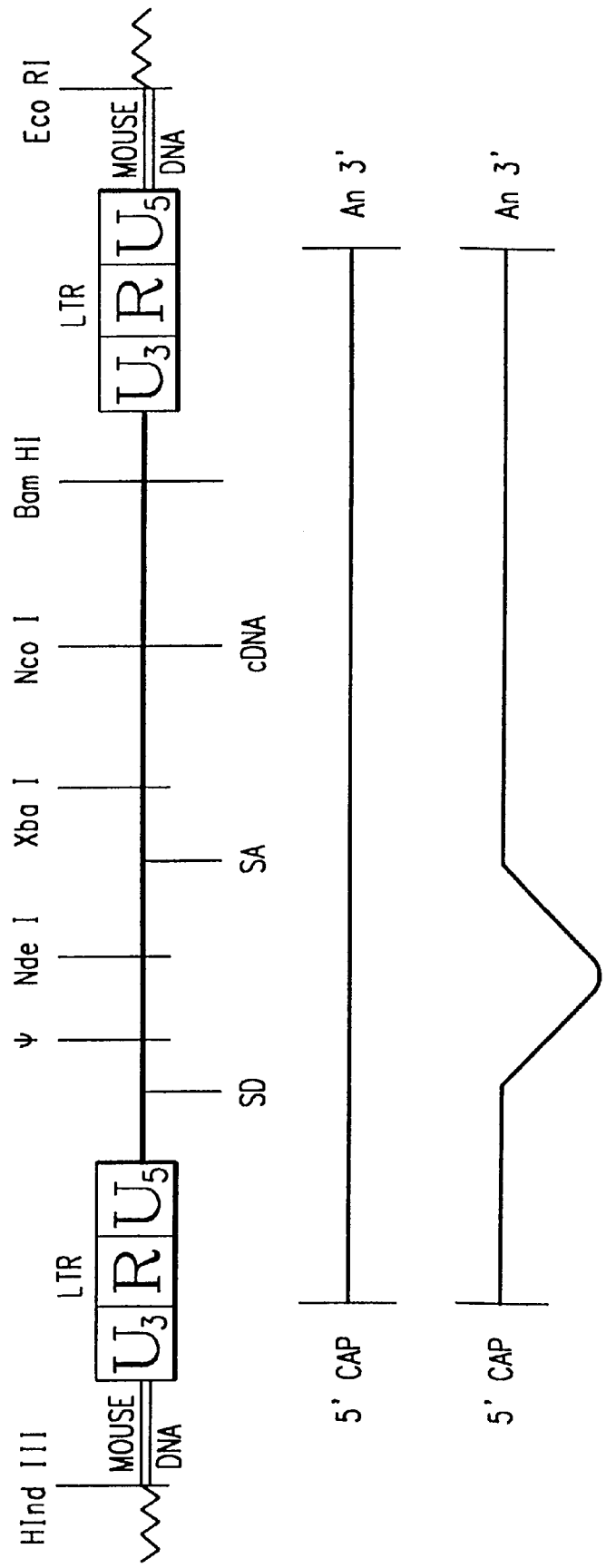

FIG. 15 illustrates the structure of the retroviral vector MFG-S. SA=splice acceptor, SD=splice donor, ψ=packaging signal. Note that the figure is not drawn to scale.

Figure 16:
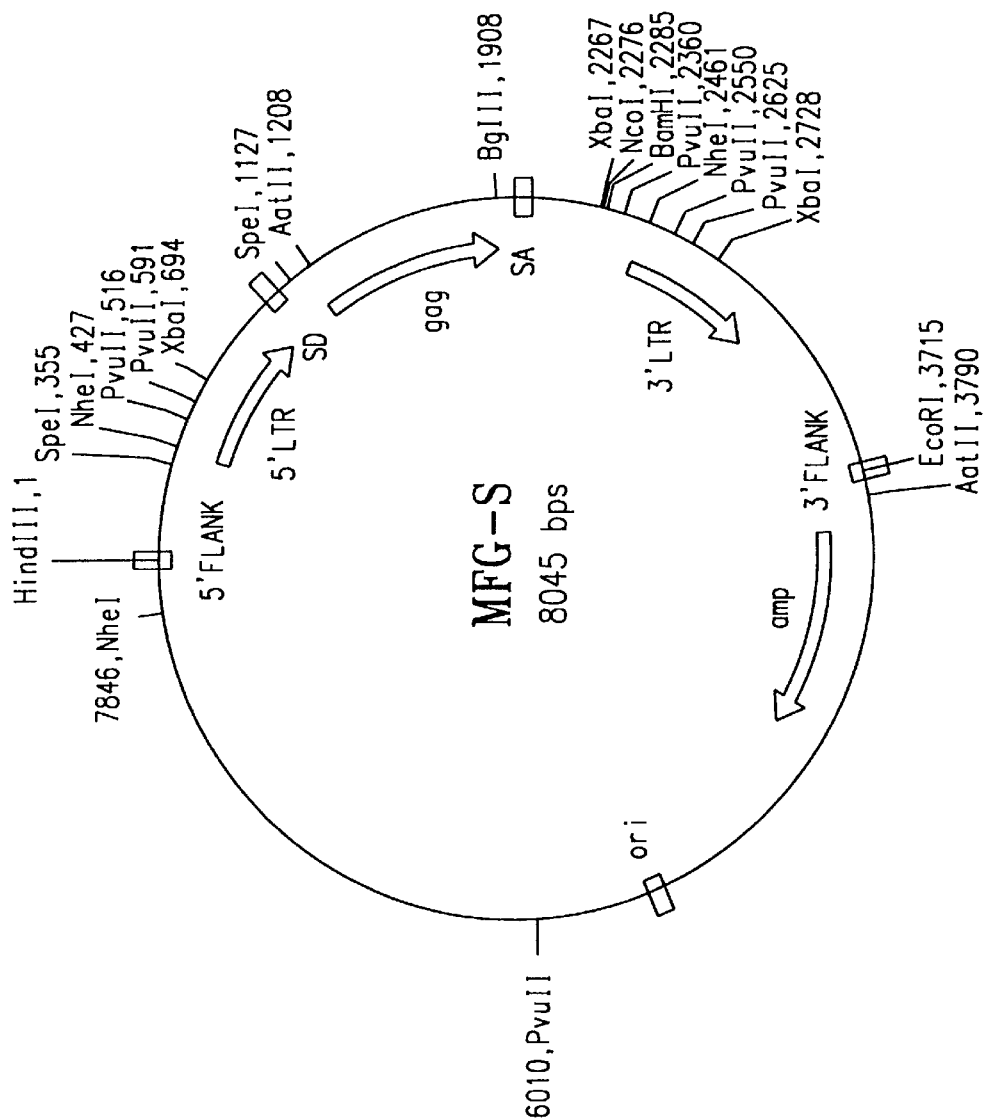

FIG. 16 is a circular restriction map of the vector MFG-S.

FIG. 17 is a DNA sequence of the 8045 BP vector MFG-S (SEQ ID NO:7).

Figure 18:
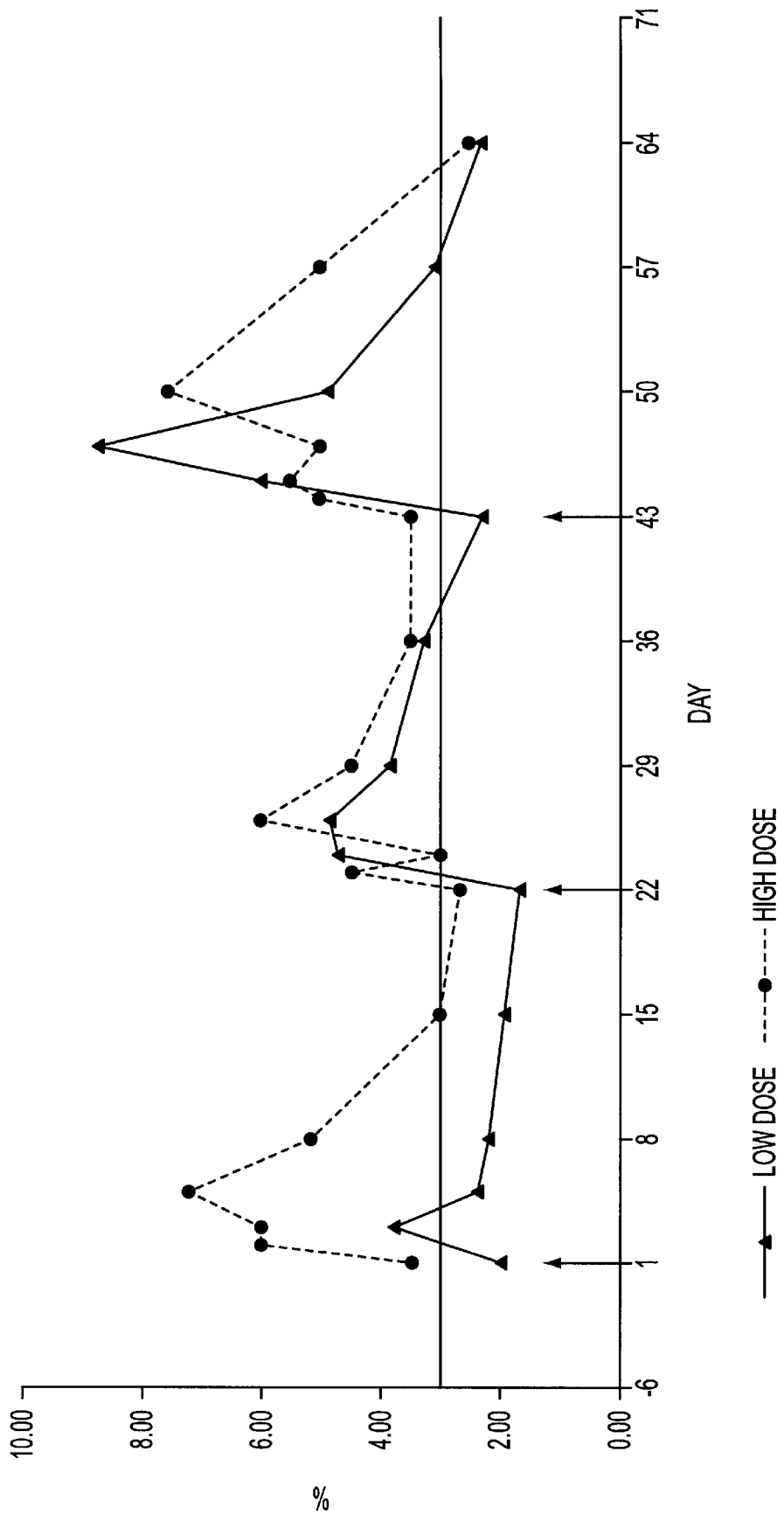

FIG. 18 shows a time course of the average percentage of eosinophils in the human melanoma patients during the 64 day period in which irradiated human melanoma cells which were transduced to express huGM-CSF using an MFG-S construct were injected into patients. The arrows indicate that the injections were made at days 1, 22, and 43. The circles represent the average data of the low dose patients and the triangles indicate the average data of the high dose patients.

5. DETAILED DESCRIPTION OF THE INVENTION

The subject invention provides for a class of retroviral vectors. The retroviral vectors provided for contain (1) 5' and 3' LTRs derived from a retrovirus of interest, the preferred retrovirus source for the LTRs is the Moloney murine leukemia virus, and (2) an insertion site for a gene of interest. The retrovirus vectors of the subject invention do not contain either a complete gag, env, or pol gene, so that the retroviral vectors are incapable of independent replication in target cells. Preferred retroviral vectors contain a portion of the gag coding sequence, preferably positioned such that the partial gag sequence is located in the retroviral vector so that the splice acceptor site is located closest to, and upstream from, the insertion site for the gene of interest.

In a particularly preferred embodiment of the subject vectors, the transcriptional promoter is positioned such that a transcript initiated from the gag promoter contains untranslated 5' gag sequence and transcript produced from nucleic acid sequence inserted into the insertion site in the vector. Vectors of interest preferably do not contain selectable markers. A preferred embodiment of such vectors is the vector designated as "MFG" (or the closely related derivative MFG-S).

Another aspect of the subject invention is to provide for retroviral vectors lacking functional enhancer elements in the 3' LTR, thereby inactivating the 5' LTR upon integration into the genome of target organisms.

Another aspect of the subject invention is to provide for retroviral vectors essentially as described above but instead of utilizing the gag promoter to control the expression of a gene inserted into the insertion site of the vector, a human alpha globin gene transcriptional promoter is used. The retroviral vector α-SGC is specifically disclosed.

Another aspect of the subject invention is to employ enhancer sequences not located in the LTRs in retroviral vectors using the alpha globin transcriptional promoter to increase the expression of a gene of interest. Of particular interest are vectors in which the enhancer sequence is placed upstream of the alpha globin transcriptional promoter. Another aspect of the subject invention is to the enhancer sequence derived from a cytomegalovirus in such non-LTR enhancer containing vectors.

Another aspect of the subject invention is to provide for retrovirus vector constructs containing genes for expression inserted into the insertion site in the retrovirus vector. Genes for insertion into the subject retrovirus vectors include any of a variety of hormones, enzymes, receptors or other drugs. The subject invention specifically provides for the genetic constructions consisting of tissue plasminogen activator (t-PA) and Factor VIII inserted (individually) into the insertion i.e., cloning sites of MFG and α-SGC, and the like.

The wild type retroviral genome has been modified by Cone and Mulligan, supra for use as a vector capable of introducing new genes into cells. As shown in FIGS. 2, the gag, the pol and the env genes have all been removed and a DNA segment encoding the neo gene has been inserted in their place. The neo gene serves as a dominant selectable marker. The retroviral sequence which remains part of the recombinant genome includes the LTRs, the tRNA binding site and the Psi packaging site. Cepko, C. et al., *Cell*, 37:1053–1062 (1984).

In addition to teaching numerous retroviral vectors containing sites for insertion of foreign genes for expression, the subject invention also provides for genetic constructions in which the retroviral vectors contain genes inserted into the site for insertion i.e., foreign genes or genes for expression. Foreign genes for inclusion in the vectors of the subject invention may encode a variety of proteins. Proteins of interest include various hormones, growth factors, enzymes, lymphokines, cytokines, receptors and the like. The term "foreign genes" includes nucleic acid sequences endogenous to cells into which the retrovirus vector containing the foreign gene may be inserted. Of particular interest for use as genes for expression are those genes encoding polypeptides either absent, produced in diminished quantities, or produced in mutant form in individuals suffering from a genetic disease.

Alternatively, the presently claimed vectors may be used to insert genes encoding at least one cytokine into primary or secondary tumor cells such that expression of the cytokine augments an individual's immune response to the tumor cells, and related tumor(s), after the transduced tumor cells are injected in vivo.

Additionally, it is of interest to use foreign genes encoding polypeptides for secretion from the target cell so as to provide for a systemic effect induced by the protein encoded by the foreign gene. Specific foreign genes of interest include those encoding hemoglobin, interleukin-1, interleukin-2, interleukin-3, interleukin-4, interleukin-5, interleukin-6, interleukin-7, interleukin-8, interleukin-9, interleukin-10, interleukin-11, etc., GM-CSF, G-CSF, M-CSF, human growth factor, insulin, factor VIII, factor IX, tPA, LDL receptors, tumor necrosis factor, PDGF, EGF, NGF, IL-1-ra, EPO, β-globin and the like, as well as biologically active muteins of these proteins (Descriptions of some of the aforementioned cytokines as well as other applicable immunomodulatory agents may be found in "Cytokines and Cytokine Receptors", A. S. Hamblin, 1993, (D. Male, ed., Oxford University Press, New York, N.Y.), or the "Guidebook to Cytokines and Their Receptors", 1995, N. A. Nicola, ed. (Oxford University Press, New York, N.Y.) herein incorporated by reference). Genes for expression by insertion into retroviral vectors may be from a variety of species; however, preferred species sources for genes of interest are those species into which the retroviral vector containing the foreign gene of interest is to be inserted.

The retroviral vectors of the subject invention are typically used by transfecting the nucleic acid sequences into packaging cell lines. Packaging cell lines contain viral gene functions that have been deleted from the retrovirus in the course of converting it to a vector. Thus, retroviral vectors of the subject invention, either with or without genes for expression inserted into the vector insertion site, may be into packaging cell lines to produce transfected infectious virus particles containing the desired genetic construction. Ideally, packaging cell lines are capable of producing a high titer of recombinant retrovirus.

Preferably, the packaging cell line will have been constructed such that the resulting replication deficient virus particles are substantially free of contaminating helper virus genomes which were used to construct the packaging cell lines. Given that the presence of contaminating helper virus genomes may result in the production of replication competent viral particles in vivo, chimeric viral particles used to effect an in vivo therapeutic benefit will be substantially helper free. For the purposes of this application, the term substantially helper free shall mean that the supernatants from NIH 3T3 cells infected with 1 ml undiluted preparation of chimeric virus produced by a given packaging cell line shall not contain significant levels of reverse transcriptase (RT) activity relative to 3T3 cells infected with replication competent virus (i.e., typically less then about ten percent the RT activity of replication competent virus). Alternatively, the safety of a vector/packaging cell system may be tested by using a vector which comprises a selective marker and assaying supernatants from 3T3 (for example) cells infected with the recombinant viral particles to test the extent to which such cells produce virus able to confer antibiotic resistance to target cells. Generally, viral supernatants which yield no antibiotic resistant target cells are deemed to be helper free.

Preferred packaging cell lines include but are not limited to Psi-2, Psi-Am, Psi-CRIP, and Psi-CRE. Psi-2 is particularly preferred for use with the retroviral vectors MFG and α-SGC.

The Psi-2 cell line described by Mulligan and coworkers was created by transfecting NIH 3T3 endothelial cells with pMOV-Psi, which is an ecotropic Moloney murine leukemia virus (Mo-MuLV) clone. pMOV-Psi expresses all the viral gene products but lacks the Psi sequence, which is necessary for encapsidation of the viral genome. pMOV-Psi expresses an ecotropic viral envelope glycoprotein which recognizes a receptor present only on mouse (and closely related rodent) cells.

Another cell line is the Psi-am line, which are Psi-2-like packaging cell lines. These Psi-am cell lines contain a modified pMOV-Psi-genome, in which the ecotropic envelope glycoprotein has been replaced with envelope sequences derived from the amphotropic virus 4070A (Hartley and Rowe, 1976, *Journal of Virology*, 19: 19–25). As a result, they are useful for production of recombinant virus with amphotropic host range. The retrovirus used to make the Psi-am cell line has a very broad mammalian host range (an amphotropic host range) and can be used to infect human cells. If the recombinant genome has the Psi packaging sequence, the Psi-am cell line is capable of packaging recombinant retroviral genomes into infectious retroviral particles (Cone and Mulligan, 1984, *Proceedings of the National Academy of Sciences, USA*, 81:6349–6353).

Two other packaging cell lines are known as Psi-CRIP and Psi-CRE. These cell lines have been shown to be useful to isolate clones that stably produce high titers of recombinant retroviruses with amphotropic and ecotropic host ranges, respectively. These cell lines are described in Danos and Mulligan, 1988, *Proceedings of the National Academy of Sciences, USA*, 85:6460–6464; and in U.S. patent application Ser. No. 07/239,545 filed Sep. 1, 1988, now abandoned.

The teachings of the reference and the patent application are incorporated herein by reference. Psi-CRIP and Psi-CRE have been deposited at the American Type Culture Collection, Rockville, Md., under Accession Nos. CRL 9808 and CRL 9807, respectively, under the terms of the Budapest Treaty.

MFG retains two intact overlapping open reading frames or ORFs that encode the amino terminal portion of both the cell surface and cytoplasmic gag-pol polyproteins. These ORFs provide a target region for recombination events with viral structural coding sequences present in the packaging cell line which could lead to the formation of replication-competent virus. In order to minimize this already remote possibility, the MFG gag ORFs can be mutagenized in such a way as to disrupt possible recombination events. Thus, a preferred retroviral vector of the invention is an MFG vector having stop codons inserted downstream from the initiation codons for the cell surface cytoplasmic gag polypeptides. A particular embodiment of this MFG vector, termed MFG-S, is more fully described by way of example in Section 12., infra.

The subject invention also includes retroviral vectors that have a gene for expression inserted into the site for gene expression. Numerous vectors incorporating various genes are specifically described by way of example in Sections 6–12, infra.

In a particular embodiment of the invention, described by way of example in Section 7, infra, MFG and α-SGC retroviral vectors carrying the gene for human tissue-type plasminogen activator (tPA) are constructed and used to efficiently transduce target endothelial cells and direct the sustained expression of high levels of tPA. In a related embodiment, described by way of example in Section 9, infra, MFG vectors carrying the gene for human Factor VIII are constructed and used to efficiently transduce endothelial cells and direct the expression of Factor VIII.

The recombinant retroviral vectors of the invention are capable of achieving transduction of cells in vivo. For example, as described more fully in Section 10, infra, the vector α-SGC-LacZ effectively transduces murine vascular endothelial cells in vivo, resulting in sustained expression of LacZ gene product in vivo. Thus, the invention provides gene therapy vectors and methods for the in situ transduction of target cells, such as, for example, vascular endothelial cells.

Another aspect of the invention relates to transduction of hematopoietic cells with the recombinant retroviral vectors of the invention, and to the treatment of a wide variety of hematologic diseases and disorders via gene therapy with such vectors, including, but not limited to anemias, hemolytic disorders, red blood cell metabolic disorders, hemoglobinopathies, thalassemias, neutrophil function disorders, leukopenia, erythrocytosis, myeloproliferative disorders, leukemias, lymphomas, eosinophilic disorders, plasma cell disorders, blood coagulation disorders, and the like.

In a specific embodiment of this aspect of the invention, described by way of example in Section 11, infra, various MFG-derived recombinant retroviral vectors carrying a gene of interest may be constructed and used to transduce hematopoietic stem cells present in bone marrow. Cells transduced by such vectors may be used in bone marrow transplantation procedures in order to regenerate a complete hematopoietic system characterized by a variety of hematopoietic cell types producing the product encoded by the transferred gene of interest. Applicants' bone marrow transplantation study results disclosed in Section 11, infra, indicate that a number of different MFG-derived vectors are capable of transducing hematopoietic stem cells, and direct the high level expression of a desired gene product in most hematopoietic cell lineages generated from such transduced stem cells for nearly the lifetime of a bone marrow transplant recipient. The results also indicate that the choice of a particular viral LTR incorporated into the vector design may influence gene expression levels.

In view of the results presented in Section 11, infra, the recombinant retroviral vectors of the invention are clearly capable of providing for long term sustained expression of genes in hematopoietic cells derived from transduced bone marrow cells. The ability to detect significant levels of gene expression in all hematopoietic lineages at over a year post-transfusion is significant, since this time approximates the normal life span of a murine bone marrow transplant recipient. These results also strongly suggest that in the case of previous studies which have demonstrated either the inactivity or shutoff of gene expression by LTR-based vectors, specific features of vector design other than the utilization of viral LTRs may contribute more to the observed problems in expression than previously suspected. Although the absolute magnitude of improvement of expression afforded by either the MPSV-LTR or the B2 derivatives of MFG-ADA described in Section 11, infra, is somewhat difficult to assess, in light of the small number of animals examined for expression in different cell lineages and the variations in expression levels observed, the data clearly suggests that those vectors offer improved expression and that the improvement appears to be general, in that it occurs in most all hematopoietic lineages.

Accordingly, the invention also provides a method of treating a hematologic disease characterized by a defective gene in a hematopoietic cell in a patient, involving the steps of isolating allogenic, HLA-identical bone marrow cells from a donor; transducing the donor bone marrow cells with a recombinant retroviral vector of the invention engineered to contain a normal gene corresponding to the defective gene at the vector insertion site; culturing the transduced donor bone marrow cells to generate a suitable population of viable cells; destroying the patient's immune system using any suitable method, such as, for example, by the administration of cyclophosphamide (i.e., 50 mg per kg per day for 4 days), or by total body irradiation alone or in combination with cyclophosphamide or other chemotherapeutic agents well known in the art; and, administering a suitable quantity of transfused donor bone marrow cells (approximately 2–6× $10^8$ transfused donor bone marrow cells per kilogram body weight) to the patient via any appropriate route of administration such as, for example, by intravenous infusion, following destruction of the patients immune system.

Yet another aspect of the invention is directed to improved vascular grafts for use in vascular surgery. A major problem with synthetic vascular grafts is their tendency to induce thrombus formation in the graft area, leading to occlusion and failure of the grafts, as well as myocardial infarction and death. Synthetic vascular grafts have never achieved long-term patency comparable to autologous saphenous vein, currently the material of choice in vascular surgical procedures such as coronary bypass operations, because of this inherent thrombogenicity. The problem is more intractable with micro-vessel grafts, and in patients that do not have an available saphenous vein for the graft.

The invention provides improved endothelialized vascular grafts which resist the formation of occlusive thrombi. More specifically, the improved vascular grafts of the invention are pre-seeded with endothelial cells which have been genetically transduced by recombinant MFG retroviral vectors carrying the gene for a thrombolytic or anti-thrombotic agent, such as tissue-type plasminogen activator (tPA). Such pre-seeded vascular grafts will, by virtue of the transduced endothelial cells lining the lumen of the graft, produce locally high levels of the thrombolytic or anti-thrombotic agent, thus inhibiting thrombus formation. In a particular embodiment of this aspect of the invention, described more fully and by way of example in Section 8, infra, the recombinant retroviral vector MFG-tPA is used to transduce canine endothelial cells, and the transduced endothelial cells are then used to endothelialize the luminal surface of a synthetic vascular graft prior to implanting the graft as an aortic-iliac bypass into test animals. The grafts seeded with MFG-tPA-transduced endothelial cells are capable of substantially inhibiting thrombus formation relative to grafts seeded with control endothelial cells, and therefore demonstrate an improved success rate. Such improved antithrombotic vascular grafts may therefore find use in surgical procedures such as coronary bypass surgery, and may eliminate the need for utilizing autologous vasculature for graft material. Various synthetic graft materials are known in the art and may be used to prepare the improved grafts of the invention, including but not limited to polymeric graft materials (e.g., polytetrafluoroethylene), teflon, and the like. Preferably, the synthetic graft material is precoated with a type of fibrinolytically-inhibited fibrin glue prior to lining the lumen of the graft with the genetically modified endothelial cells. For recent discussions of endothelialized synthetic vascular grafts, see, for example, Zilla et al., 194, J. Vasc. Surg. 19:540–548; and Ahlswede and Williams, 1994, Arterioscler. Thromb. 14:25–31.

Thus, there is provided an improved synthetic vascular graft, comprising a lining of autologous endothelial cells genetically modified to produce an thrombolytic or anti-thrombic protein such as, for example, human tissue-type plasminogen activator, on the luminal surface of the graft, wherein said endothelial cells have been modified prior to implantation of the graft by transducing parental endothelial cells with a recombinant retroviral vector of the invention, engineered to contain the coding sequence for the thrombolytic or anti-thrombic protein at the vector insertion site.

The retroviral vectors of the invention may be used in a wide variety of cell types, including but not limited to epithelial cells, fibroblast cells, hepatocytes, endothelial cells, myoblast cells, astrocyte cells, lymphocyte cells, mesenthelial cells, and the like. Of particular interest are the cell types disclosed in the following patents and patent publications: U.S. Pat. Nos. 4,868,116, issued Sep. 19, 1989, and 4,980,286, issued Dec. 25, 1990 (epithelial cells), PCT/US89/00422, WO89/07136 published Aug. 10, 1989 (hepatocyte cells), EP 378,576 published Jul. 25, 1990 (fibroblast cells), and PCT/US88/04383, WO89/05345 published Jun. 15, 1989 and WO/90/06997, published Jun. 28, 1990 (endothelial cells), the disclosures of which are incorporated herein by reference.

The vectors of the subject invention find a variety of uses in the treatment of various medical conditions, including, but not limited to cancer, genetically based diseases, cardiopulmonary diseases, endocrinological diseases, and the like.

Typically, the therapeutic use of the claimed vectors may include either the ex vivo or in vivo incorporation of genetic material which encodes biologically active material of interest into mammalian cells (by viral transduction/infection) for subsequent delivery to the body.

Given that the subject vectors may be used to provide a therapeutic benefit to an individual, one of ordinary skill will appreciate that, from a medical practitioner's or patient's perspective, virtually any alleviation or prevention of an undesirable symptom (e.g., symptoms related to disease, sensitivity to environmental or factors, normal aging, and the like) would be desirable. Thus, for the purposes of this Application, the terms "treatment", "therapeutic use", or "medicinal use" used herein shall refer to any and all uses of the claimed compositions which remedy a disease state or symptoms, or otherwise prevent, hinder, retard, or reverse the progression of disease or other undesirable symptoms in any way whatsoever.

Retrovirally transduced cells which will be reimplanted in vivo will generally be tested for sterility (absence of mycoplasma, bacteria, fungus, or other potential pathogens), viability, expression of the gene of interest, and for the presence of proviral sequences, and absence of replication competent helper virus. Additionally, depending on the type of transduced cell to be implanted, it may prove necessary or advantageous to associate the cells with a biocompatible support matrix (e.g., Dacron grafts, prosthesis, microcarrier beads, etc.) before introducing the cells to the body. In addition to allowing the insertion and maintenance of cells at or near a specific location, solid support matrices may facilitate the long term in vivo maintenance of the transduced cells.

Where transient use is contemplated, the transduced cells may optionally be irradiated prior to implantation to prevent further replication of the cells. Irradiation is particularly important where the transduced tumor cells are being utilized because replication competent tumor cells may reestablish tumors upon introduction in vivo. Given that transduced cells will continue to express the gene of interest after being irradiated, implantation results in a transient window of immune stimulation during which the irradiated tumor cells express cytokine in the intimate presence of tumor antigen. The amount of radiation utilized will be that required to ensure that all of the tumor cells to be introduced are not capable of sustained replication. Typically, the amount of radiation will comprise about 3,500 rads, and may come from any form of ionizing radiation which may render cells incapable of sustained replication (e.g., a $^{137}$Cesium source discharging about 124 rads/min).

Additionally, those of skill in the art will appreciate that many subtle or silent nucleotide changes may be made in subject vectors without substantially affecting the operative features (i.e., transduction efficacy) of the vectors. As such, the present invention also contemplates the use of any and all operative (transfection competent) derivatives of the claimed retroviral constructs to deliver genes encoding mammalian hormones, factors, enzymes, or receptors to cells.

The present invention will now be illustrated by the following examples, which are not intended to be limiting in any way.

6. EXAMPLE: CONSTRUCTION OF MFG AND α-SGC RETROVIRAL GENE THERAPY VECTORS 6.1. Materials and Methods
6.6.1. Construction of MFG Vector Precursor
6.6.1.1. Construction of pMOV-Psi Plasmid pMOVPsi was constructed as follows: Three purified DNA fragments were ligated together to construct PMOV Psi−. The first was obtained by digesting PMOV Psi+ with Xho I to completion, followed by partial digestion with EcoRI. Chumakov, I. et al., *Journal of Virology*, 42:1088–1098 (1982). The fragment extending from the Xho I site at 2.0 U in MULV, through the 3' LTR, 3' mouse flanking sequence, all of pBR322, and ending at the EcoRI site was purified from an agarose gel after electrophoretic separation. Vogelstein, B. and D. Gillespie, *Proceedings of the National Academy of Sciences, USA*, 761:615–619 (1979). The second fragment was obtained by digestion of 6 PMOV Psi+ with Bal I to completion followed by purification of the fragment extending from the Bal I site in pBR322 through 5' mouse flanking sequence and 5' LTR to the Bal I site located at 0.7 U of MuLV. HindIII linkers (Collaborative Research) were then blunt-ligated to this fragment with T4 DNA ligase, and the fragment was digested with excess HindIII and EcoRI. The LTR- containing fragment was purified from an agarose gel after electrophoretic separation. The third fragment present in the final ligation reaction was obtained from pSV2gag/pol where the gag/pol region of MULV had been subcloned into pSV2. Mulligan, R. C. and P. Berg, *Science*, 209:1422–1427 (1980). pSV2-gag/pol was digested to completion with Xho I and HindIII and the fragment extending from the HindIII site (changed from the Pst I site at 1.0 U of MuLV) to the Xho I site at 2.0 of MuLV was purified from an agarose gel following electrophoretic separation. These three DNA fragments were then mixed in equimolar amounts at a total DNA concentration of 50 ug/ml in ligase buffer (50 mM Tris-HCl [pH 7.8]), 10 mM $MgCl_2$, 20 mM dithiothreitol, 1.0 mM ATP, 50 ug/ml bovine serum albumin), and incubated with T4 DNA ligase for 18 hr at 15° C. *E. coli* HB101 was transfected with the ligated DNA, and ampicillin resistant transfectants were obtained. The plasmid DNA obtained from a number of transformants was screened for the desired structure by digestion with appropriate restriction endonucleases and electrophoresis through agarose gels. Davis, R. W. et al., Methods in Enzymology, 65:404–411 (1980).

Cell lines containing the Psi mutant stably integrated into the chromosome were made by cotransfection of pMOV-Psi and pSV2gpt, a SV40 hybrid vector capable of XG PRT expression. Mulligan, R. C. and P. Berg, Science, 209:1422–1427 (1980). Cells from gpt+ colonies obtained in this way ere cloned and established into three lines: Psi-1, Psi-2, and Psi-3.

6.1.1.2 Construction of pLJ

The characteristics of the pLJ vector have been described in Korman, A. J. et al., *Proceedings of the National Academy of Sciences, USA*, 84:2150 (1987). This vector is capable of expressing two genes: the gene of interest and a dominant selectable marker, such as the neo gene. The gene of interest is cloned in direct orientation into a BamHI/SmaI/SalI cloning site just distal to the 5' LTR, while, the neo gene is placed distal to an internal promoter (from SV40) which is farther 3' than is the cloning site (is located 3' of the cloning site). Transcription from pLJ is initiated at two sites: 1) the 5' LTR, which is responsible for expression of the gene of interest and 2) the internal SV40 promoter, which is responsible for expression of the neo gene. The structure of pLJ is represented in FIG. 2a.

Vector pLJ is represented in FIG. 2a. In pLJ, the genetic material of interest is inserted just following the 5' LTR. Expression of this genetic material is transcribed from the LTR and expression of the neo gene is transcribed from an internal SV40 promoter.

6.1.1.3. Construction of PEm

In this simple vector, the entire coding sequence for gag, pol and env of the wild type virus is replaced with the gene of interest, which is the only gene expressed. The components of the pEm vector are described below. The 5' flanking sequence, 5' LTR and 400 bp of contiguous sequence (up to the BamHI site) is from pZIP. The 3' flanking sequence and LTR are also from PZIP; however, the ClaI site 150 bp upstream from the 3' LTR has been ligated with synthetic BamHI linkers and forms the other half of the BamHI cloning site present in the vector. The HindIII/EcoRI fragment of pBR322 forms the plasmid backbone. This vector is derived from sequences cloned from a strain of Moloney Murine Leukemia virus. An analogous vector has been constructed from sequences derived from the myeloproliferative sarcoma virus. The structure of pEm is represented in FIG. 2b.

Vectors without a selectable marker can also be used to transduce a variety of cell types, such as endothelial cells with genetic material of interest. Such vectors are basically simplifications of the vectors previously described, in which there is such a marker. Vector pEm is represented in FIG. 2b; as represented, the main components of the vector are the 5' and 3' LTR, and the genetic material of interest, inserted between the two LTRS.

6.1.2. Construction of the MGF Vector

The MFG vector having the identifying characteristics of ATCC accession No. 68754 is derived from the pEM vector but contains 1038 base pairs of the gag sequence from MMLV to increase the encapsulation of recombinant genomes in the packaging cell lines, and 350 base pairs derived from MOV-9 which contains the splice acceptor sequence and transcriptional start. An 18 base pair oligonucleotide containing NcoI and BamHI sites directly follows the MOV-9 sequence and allows for the convenient insertion of genes with compatible sites. The MMLV LTR controls transcription and the resulting mRNA contains the authentic 5' untranslated region of the native gag transcript followed directly by the open reading frame of the inserted gene. The structure of MFG is represented in FIG. 2c. A more detailed map of MFG is provided in FIG. 13. Details for the construction of MFG are provided in FIGS. 9(a) and 9(b).

MFG was constructed by ligating the 5' LTR containing XhoI/NdeI fragment of the half-GAG retroviral vector (half-GAG is described in Bender, et al., *J. Virol.* 61:1639–1646) to an XhoI/BamHI H4 histone promoter fragment. Retroviral vector pEM was digested with NdeI and BamHI, and the 3' LTR containing fragment was ligated to the halfGAG fragment already ligated the H4 fragment so as to produce an intermediate retrovirus vector containing 2 LTRs in the proper orientation and also containing the H4 fragment within the viral portion of the vector. The intermediate vector was then linearized by digestion with NdeI and the NdeI site in the pBR322 portion of the vector was filled in by polymerase and destroyed by ligation. The vector was subsequently digested with XhoI and the XhoI site was joined to NdeI linker. The vector was subsequently cleaved with BamHI and the large fragment containing both LTRs and the pBR322 sequence) was purified.

A linker having XhoI and BamHI and having the following sequence:

CTAGACTGCCATGGCGCG TGACGGTACCGCGCCTAG was synthesized and ligated to both the BamHI site on the cleared intermediate vector and an NdeI/XbaI fragment from pMOV9 [containing a splice acceptor site next to the NdeI edge] so as to form a circular vector, MFG as illustrated in FIGS. 2c, 3 and 9(a) to 9(b). The plasmid containing vector MFG has been deposited with the American Type Culture Collection and it has accession number 68,754.

6.1.3. Construction of the α-SGC Vector

The α-SGC vector (ATCC accession number 68755) utilizes transcriptional promoter sequences from the α-globin gene to regulate expression of the tPA gene. The 600 base pair fragment containing the promoter element additionally contains the sequences for the transcriptional initiation and 5' untranslated region of the authentic α-globin mRNA. A 360 base pair fragment which includes the transcriptional enhancer from cytomegalovirus precedes the α-globin promoter and is used to enhance transcription from this element. Additionally, the MMLV enhancer is deleted from the 3' LTR. This deletion is transferred to the 5' LTR upon infection and essentially inactivates the transcriptional activating activity of the element. The structure of α-SGC is represented in FIG. 2d. A more detailed description of α-SGC is provided in FIG. 4. A plasmid containing the α-SGC vector has been deposited with the American Type Culture Collection and it has accession number 68,755. The following examples provide examples of using the retroviral vectors of the invention using endothelial cells. It will be understood that other cell types are suitable as well, including without limitation epithelial cells, fibroblast cells, hepatocyte cells and others.

7. EXAMPLE: USE OF MFG AND α-SGC VECTORS TO AFFECT INCREASED EXPRESSION OF HUMAN TISSUE PLASMINOGEN ACTIVATOR IN ENDOTHELIAL CELLS

Tissue plasminogen activator (tPA) is a protein normally secreted by endothelial cells that promotes fibrinolysis of blood clots. Recombinant retroviral vectors encoding human tPA were constructed and used to transduce canine endothelial cells in order to demonstrate the enhanced delivery of a therapeutically relevant protein from transduced endothelial cells.

7.1. Materials and Methods 7.1.1. Construction of MGF and α-SGC Vectors Encoding tPA The modifications of the tPA gene for cloning into the recombinant retroviral vectors are shown in FIG. 10. The coding sequences of human uterine tPA were contained within a Sal I DNA fragment of a pUC-based plasmid obtained from Integrated Genetics Inc. Framingham Mass. The Sal I fragment was derived by placing Sal I linkers at the SFaN I site at base pair 6 and the Bgl II site at base pair 2090 of the original cDNA. The coding sequences extends from base pair 13 to base pair 1699.

From this original clone a fragment that could be cloned directly into the MFG and α-SGC vectors described in Section 6.1, supra. The Sal I fragment was first converted to a Bam HI fragment by the addition of synthetic Bam HI linkers and then digested with the restriction enzyme Bgl II to yield a 109 base pair BamHI to BglII fragment and a 1975 base pair Bgl II to Bam HI fragment. To recreate the missing 100 base pairs of tPA coding sequences and the translational start codon, two 104 base pair oligonucleotides were chemically synthesized and annealed to create a fragment with an Nco I site at the 5' end and a Bgl II site at the 3' end. This oligonucleotide was ligated onto the Bgl II site of the partial 1975 base pair tPA gene to create a 2079 base pair tPA gene with the identical coding sequence of the original molecule, but which can be easily obtained as an Nco I to Bam HI fragment. It was inserted directly into the MFG and α-SGC vectors (the resulting vectors were given ATCC accession numbers 68727 and 68729, respectively). These manipulations were performed by standard molecular biological techniques (Molecular Cloning—A laboratory Manual, T. Maniatis, E. F. Frisch, and J. Sambrook), and are diagrammed in FIG. 2.

7.1.2. Preparation of MGF-tPA and α-SGC-tPA Producer Cell Lines

Cell lines producing recombinant virus encoding MFG-tPA and α-SGC-tPA were made from the Psi packaging cell line of Danos and Mulligan capable of producing recombinant retrovirus of amphotropic host range [Proc. Natl. Acad. Sci. U.S.A. 85:6460 (1988)]. 10 ug of the specified DNAs and 1 ug of the plasmid pSV2neo were co-precipitated and transfected onto the packaging cells by standard calcium phosphate transfection procedures. Stably transfected clones were isolated after growth for 14 days in selective media containing 800 ug/ml G418. 24 hour culture supernatants were obtained from confluent monolayers of individual clones and used to infect NIH 3T3 cells. The culture supernatants were removed after 24 hours exposure, and the 3T3 cells were refed with normal media and allowed to grow for an additional 72 hours. Fresh media was placed on these cells for 6 hours and these supernatants were assayed for human tPA with a commercially available ELISA specific for human tPA (Immunobind-5, American Diagnostica Inc., N.Y., N.Y.) From this screen, clones of the packaging cell line producing either the MFG-tPA recombinant virus or the α-SGC-tPA recombinant virus were selected and designated MFG 68 and α-SGC 22, respectively.

7.1.3. Target Endothelial Cells and Transduction with MFG-tPA and α-SGC-tPA Vectors Canine endothelial cells were isolated from 10 cm segments of the external jugular vein by collagenase digestion as described [T. J. Hunter S. P. Schmidt, W. V. Sharp, and (1983) Trans. Am. Soc. Artif. Intern. Organs 29:177]. The cells were propagated on fibronectin-coated tissue culture dishes in M199 media containing 5% plasma-derived equine serum, 50 ug/ml endothelial cell growth factor, and 100 ug/ml heparin. Purity of the cell cultures was determined by immunohistochemical assay for the presence of Von Willebrands Factor and the absence of smooth muscle cell specific α-actin.

The day before transduction, the endothelial cells were seeded at $5.5 \times 10^3$ cells/cm$^2$ in medium without heparin. The following day, the endothelial cells were exposed for 24 hours to supernatants containing recombinant virus derived from each producer cell line to which was added 8 ug/ml polybrene. The viral supernatants were removed, the cells feed with normal media and growth was allowed to proceed for an additional 48 hours before analysis.

High molecular weight genomic DNA and total RNA were isolated from cultures of endothelial cells by standard techniques (*Molecular Cloning—A Laboratory Manual,* T. Maniatis, E. F. Fritsch, and J. Sambrook). The DNA and RNA were analyzed by hybridization analysis with a $^{32}$P-labeled DNA probe prepared from the entire tPA cDNA fragment. Standard techniques were used for electrophoretic separation, filter transfer, hybridization, washing, and $^{32}$P-labeling (Molecular Cloning—A Laboratory Manual T. Maniatis, E. F. Fritsch, and J. Sambrook). The production of human tPA in transduced canine endothelial cells was demonstrated with a species specific immunocytochemical stain. Transduced cells were fixed in 3% formaldehyde for 10 minutes at room temperature and then permeabilized in 0.1% Triton X-100 for 5 minutes. The fixed cell monolayer was then incubated sequentially with a murine monoclonal antibody to human tPA, with an alkaline phosphatase conjugated goat anti-mouse antibody, and finally with a color reagent specific for alkaline phosphatase. This procedure specifically stains those cells expressing human tPA and can be visualized by conventional light microscopy. In addition, tPA secretion from transduced cells was determined from confluent cell monolayers. Fresh media was placed on the cells for 6 hours, removed and clarified by centrifugation, and the amount of human tPA determined with a commercially available ELISA (Immunobind-5, American Diagnostics).

7.2. Results

Figure 5:
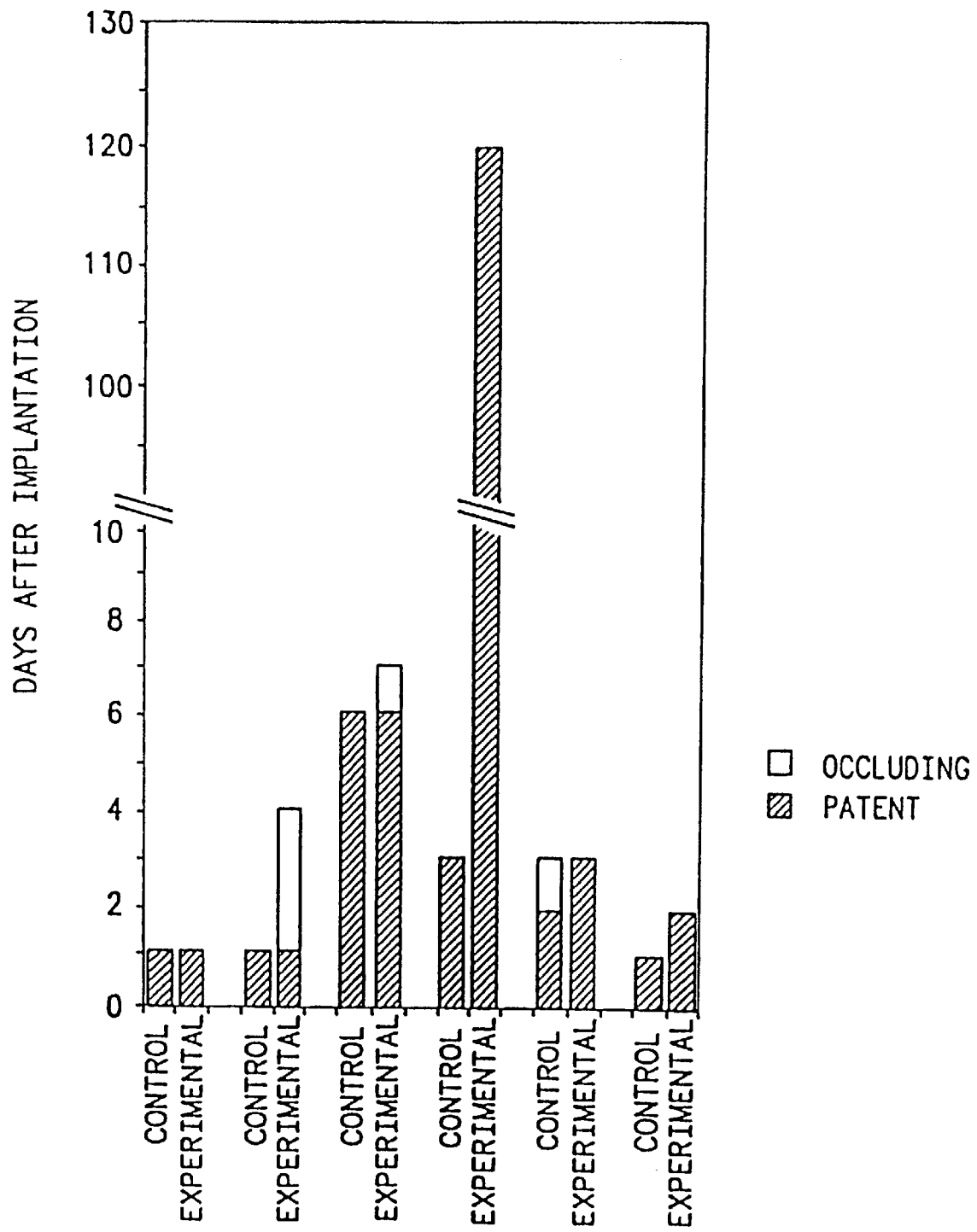
FIG. 5 is a histogram showing the patency after implantation into dogs of synthetic grafts lined with endothelial cells genetically augmented to express TPA.

The efficiency of the transduction process is shown by immunocytochemical stain of a population of cells mock transduced or transduced with MFG-tPA. As shown in FIG. 5, after a single exposure of the cells to a viral supernatant harvested from MFG 68, essentially all of the cells are synthesizing human tPA as opposed to none of the cells in the control. This was achieved without selection of any type for transduced cells.

An immunological assay was conducted to determine the amount of tPA that was being secreted from transduced cultures. As shown below, cells transduced with recombinant virus from either MFG 68 or α-SGC 22 secreted large amounts of human tPA. Under similar conditions, human endothelial cells in culture typically secrete approximately 1 ng of tPA [Hanss, M., and D. Collen (1987) *J. Lab. Clin. Med.* 109:97–104].

TABLE I

| Cells | ng tPA/10$^6$ cells/6hrs. |
|---|---|
| uninfected K9 EC | 0.0 |
| MFG 68 K9 EC | 150.1 |
| α-SGC 22 K9 EC | 302.8 |

As a further confirmation that the endothelial cells had been transduced with recombinant virus from MFG 68 and α-SGC 22, DNA and RNA was isolated from transduced cells and analyzed by hybridization to a radiolabeled tPA gene. An autoradiogram of the DNA analysis was performed. No hybridization was detected in the uninfected controls, but single hybridizing species of the appropriate molecular eight was seen in the cells infected with the two recombinant vectors. This demonstrates that the genetic information has been transferred to the genome of these transduced cells.

Hybridization analysis of total RNA isolated from these cells confirms the protein and DNA results. Again no hybridization was detected in the control cells but in the RNA derived from the transduced cells hybridizing bands of the appropriate sizes can be seen. RNA from the MFG 68 and α-SGC 22 recombinant virus producing cells is also shown as controls.

8. EXAMPLE: IN VIVO ANTITHROMBOTIC ACTIVITY OF VASCULAR GRAFTS SEEDED WITH MFG-tPA-TRANSDUCED ENDOTHELIAL CELLS 8.1. Materials and Methods Endothelial cells were enzymatically harvested from external jugular veins of adult female mongrel dogs that weighed 20–25 kg and cultured in the laboratory and analyzed for purity as described in Example 7, supra. One half of the cells isolated from each animal were transduced by two exposures to supernatants from the MFG 68 cell line producing the MFG-tPA recombinant virus as described in the previous section. The other half were mock transduced. Growth curves conducted on each population showed no difference in growth characteristics. ELISA measurements were made on culture supernatants derived from each batch of transduced cells to assure that tPA was being secreted from the augmented cells. These cells were then propagated in the laboratory for approximately one week to obtain sufficient numbers of cells.

For each animal from which cells had been isolated, two vascular grafts made of expanded Teflon (W. L. Gore and Associates, Inc. Flagstaff, Ariz.) were seeded with cells. One graft was seeded with mock transduced cells, and the other with cells transduced to secrete high levels of tPA. Each graft, measuring 0.4 cm×14 cm, was precoated with 1.5 ug/cm$^2$ fibronectin (Sigma Chemical Corp., St. Louis Mo.), and then seeded with 2200,000 endothelial cells/cm. The grafts were then incubated for an additional 72 hours in culture. Prior to implant the ends were cut off each graft and checked to assure cell coverage.

The same dogs from which the cells had been harvested were anesthetized and 10 cm segments of the seeded grafts were implanted as aorta-iliac bypasses. Each dog received two contralateral grafts; one seeded with control cells and the other seeded with cells that had been transduced to secrete high levels of tPA. Following implantation the performance of the grafts was monitored daily with a B-mode scanner which locates the graft with ultrasound and assesses blood flow through the graft by Doppler measurements (Accuson, Inc.). No drugs to reduce thrombus formation were administered to the animals.

8.2. Results

The results of graft performance in 6 different animals were analyzed. The results are indicated in FIG. 5. The implant model described above is an extremely stringent one and leads to rapid graft failure by occlusive clot formation. Normal graft function is denoted by solid bar, and a graft which is failing but still functioning by a striped bar. In the first animal, the control graft and the graft lined with transduced cells secreting enhanced levels of tPA (experimental) failed due to clot formation 24 hours after implant. In all of the other five animals, the graft lined with transduced cells secreting enhanced levels of tPA functioned longer than the graft with cells which had only been mock transduced. This difference varied from 24 hours to several months. These results demonstrate that a therapeutic effect can be achieved in vivo with MFG-transduced endothelial cells.

9. EXAMPLE: USE OF MFG VECTOR TO PRODUCE HUMAN FACTOR VIII IN ENDOTHELIAL CELLS 9.1. Materials and Methods 9.1.1. Construction of MGF/Factor XIII Vector Endothelial cells were genetically augmented to produce human factor VIII by transducing cells with a retroviral vector, MFG, containing a modified human factor VIII gene (ATCC accession no. 68726). The modified factor VIII cDNA contains all of the coding sequences for the A1, A2, A3, C1, and C2 domains, however the B domain is deleted from amino acids 743 to 1648. The removal of the B domain and the insertion of the modified factor VIII gene into the retroviral vector MFG is described in detail below and depicted in FIG. 7.

A full-length cDNA without the 5' and 3' untranslated sequences was obtained in a plasmid vector inserted between the restriction sites Nco I (5') and Xho I (3'). For removal of the B domain, the factor VIII cDNA was subcloned into a plasmid vector in 4 fragments spanning the sequences on both the 5' and 3' sides of the B domain. The first fragment of the factor VIII cDNA was subcloned between the restriction sites Sal I and Pst I in the plasmid vector pUC 9. The plasmid vector was cut with Sal I and Pst I and the 5' phosphates were removed using calf intestinal phosphatase. A 1591 base pair Xho I (nucleotide 7263) to Nde I (nucleotide 672) fragment, and a 359 base pair Nde I (nucleotide 5672) to Pst I (nucleotide 5313) fragment from the full-length cDNA were isolated and ligated with the Sal I/Pst I digested plasmid vector.

To remove the majority of the sequences encoding the B domain which joins amino acids 742 to 1649 in the same translational reading frame, 4 oligonucleotides were synthesized with a 5' Hind III site and a 3' Pst I site covering 168 base pairs. The oligonucleotides extend from the Hind III site at nucleotide 2427 which encodes amino acid 742 followed by amino acid 1649 which is the first amino acid of the activation peptide of the light chain through to the Pst I site at nucleotide 5313. The plasmid vector pUC 9 was digested with the restriction enzymes Hind III and Pst I, and the 5' phosphates were removed using calf intestinal phosphatase. The oligonucleotides were synthesized as 4 separate strands, kinased, annealed and ligated between the Hind III site and the Pst I site of the plasmid vector.

The subcloned Hind III/Pst I oligonucleotide was juxtaposed to the Pst I/Xho I fragments in a plasmid vector pUC F8. To generate this plasmid, a new polylinker was inserted into a pUC 9 plasmid backbone with the new polylinker encoding the restriction enzyme sites 5' Sma I-Bam HI-Xho I-Pst I-Hind III-Asp 718-Nco I-Hpa I 3' used. The plasmid vector was digested with the restriction enzymes Bam HI and Hind III, and the 5' phosphates were removed with calf intestinal phosphatase. A partial Pst I/Bam HI digest of the Pst I/Xho I subclone was used to isolate the 3' terminal factor VIII fragment, and a Pst I/Hind III digest of the subcloned oligonucleotides was used to isolate the heavy and light chain junction fragment. They were ligated into the plasmid vector pUC FB between the BamHI and Hind III sites.

This subclone containing the factor VIII sequences between nucleotides 2427 and 7205 was digested with Asp 718 and Hind III, and the 5' phosphates were removed using calf intestinal phosphatase. A fragment encoding factor VIII between the restriction enzyme sites Asp 718 (nucleotide 1961) and Hind III (nucleotide 2427) was isolated and ligated into the plasmid vector to generate a subclone (pF8 3' delta) containing the factor VIII sequences from nucleotide 1961 through to the translational stop codon at nucleotide 7205.

The construction of the retroviral vector containing the modified factor VIII gene was carried out by inserting the factor VIII gene between the restriction sites Nco I and Bam I of the retroviral vector MFG. The factor VIII subclone F8 3' delta was digested with Sma I and converted to a BglII site using an oligonucleotide linker. An Asp 718/Bgl II -fragment was isolated from the 3' factor VIII subclone, and a 5' factor VIII fragment containing the ATG for initiation of translation was isolated as an Nco I (nucleotide 151)/Asp 718 fragment (nucleotide 1961). The retroviral vector MFG was digested with Nco I and Bam HI, and the 5' phosphates were removed using calf intestinal phosphatase. The factor VIII fragments were ligated into the retroviral vector yielding the final factor VIII retroviral construct, see FIG. 6.

9.1.2. Preparation of MFG/Factor VIII Producer Cell Lines

The cell line producing the retroviral particles was generated by transfection of the retroviral vector MFG/factor VIII into equal numbers of ecotropic packaging cells Psi CRE and amphotropic packaging cells CRIP as described by Bestwick et al. (*Proc. Natl Acad. Sci. USA* 85:5404–5408 (1988)). To monitor the extent of superinfection taking place between the 2 host ranges of packaging cells, the production of biologically active factor VIII was measured using the Kabi Diagnostica Coatest for Factor VIII, Helena Laboratories, Beaumont, Tex. and the production of viral RNA was measured by an RNA dot blot analysis. At 21 days post transfection, the mixture of transfected packaging cells was co-cultivated with the amphotropic packaging cell line Psi CRIP-HIS. The CRIP HIS packaging cell line is a variant of the previously described CRIP packaging cell line. The CRIP HIS packaging cell line is identical to the Psi CRIP packaging cell line except that the retroviral envelop gene was introduced into the cell by cotransfection with pSV2-HIS plasmid DNA, a different dominant selectable marker gene. The packaging cell lines were cultured at a 1:1 ratio for isolation of a homogeneous amphotropic retroviral stock of transducing particles. The superinfection of the amphotropic packaging cell line CRIP HIS has led to the generation of a stable cell line, HIS 19, which produces recombinant retrovirus that efficiently transduce the modified human factor VIII gene. Antibiotic selection of the retroviral introducing cell line was not required to isolate a cell line which produces high-titer recombinant retrovirus. The genomic DNA of the cell line has been characterized by Southern blot hybridization analysis to determine the number of integrated copies of the retroviral vector present in the producer cell line. The copy number in the retroviral producing cell line is approximately 0.5, therefore on average 50% of the CRIP-HIS packaging cells contain a copy of the retroviral vector with the modified factor VIII gene. The retroviral vector and the modified factor VIII gene are intact without any deletions or rearrangements of the DNA in the packaging cell line. The copy number of the retroviral vector remains constant with the continuous passage of the retroviral producing cell line. For obtaining the highest titer of recombinant retrovirus, HIS 19 was carried 3 passages in selective histidine minus media followed by 4 passages in completed DMEM media. For the generation of retroviral particles, HIS 19 was seeded at $5 \times 10^5 - 1 \times 10^6$ cells in a 10 cm cell culture dish. At 48 hours postseeding, approximately 70% confluency, fresh medium (DMEM +10% calf serum) was added to the plates for collection 24 hours later as the source of recombinant retrovirus for transduction.

9.1.3. Endothelial Cell Transduction

The modified factor VIII gene was transduced into canine endothelial cells isolated from the jugular vein. The endothelial cells were seeded at $3 \times 10^5$ cells per 10 cm. dish in complete M199 medium with 5% plasma derived serum (Equine), 100 ug/ml heparin, and 50 ug/ml endothelial cell growth factor for 4–6 hours. The cells were then incubated overnight in M199 medium with 5% plasma derived serum, and 100 ug/ml endothelial cell growth factor overnight without heparin which adversely affects the efficiency of the transduction process. Cells were exposed to the fresh viral supernatant plus polybrene (8 ug/ml) for 24 hours. After removal of the viral supernatant, the cells were put into M199 medium with 5% plasma derived serum, 100 ug/ml endothelial cell growth factor to grow to approximately 70–80% confluence. At that time, the medium was changed to M199 medium with 5% heat inactivated fetal bovine serum (heated at 66° C. for 2 hours), and 50 ug/ml of ECGF. Following a 24 hr. incubation, the medium was collected and assayed for biological active factor VIII by the Kabi Coatest.

9.2. Results: In Vitro Transduction of Endothelial Cells

With this retrovirus producing cell line, between 50% and 75% of the endothelial cells were transduced as determined by Southern blot analysis. The factor VIII gene can be transduced at this frequency with a single exposure to the recombinant retrovirus, and without antibiotic selection of the transduced cells. The transduced endothelial cells contain an intact copy of the recombinant retroviral genome and the modified factor VIII gene without any deletions or rearrangements. The rate of production of biologically active factor VIII from the genetically augmented endothelial cells was 400 ng/$5 \times 10^6$ cells/24 hrs.

10. EXAMPLE: IN VIVO TRANSDUCTION OF ENDOTHELIUM

Using standard stocks of recombinant retrovirus made as described in the previous examples, data demonstrating the in vivo transduction of endothelial cells has been generated as described herein. The approach is based on the previously published observation (Reidy M A, Schwartz S M, *Lab Invest* 44:301–308 (1981)) that a defined injury to an artery surface removes a small strip of endothelial cells and this denuded area heals within seventy-two hours by proliferation and in growth of new endothelial cells from the edge of the defect. Cell division is a requirement for effective transduction by recombinant retroviruses and the injury of the endothelium with a wire is one of potentially many methods to induce endothelial cell proliferation. Our method uses Reidy's technique of defined injury to induce endothelial cell proliferation, then exposes the proliferating cells directly to supernatants containing recombinant retroviral vectors. Our initial experiments document the ability of this method to successfully transduce endothelial cells in situ, thus potentially avoiding the necessity of tissue culture techniques for the successful introduction of new genetic sequences.

This method requires two surgical procedures, the first procedure injures the blood vessel surface (here described for the right iliac artery) and induces the proliferation of endothelial cells. The second procedure delivers recombinant retrovirus to the cells undergoing replication on the vessel surface, while preventing the flow of blood from the proximal arterial tree while the proliferating cells are exposed to retroviral particles. For simplicity of performance the procedure is described for iliac arteries.

10.1. Materials and Methods

Figure 1:
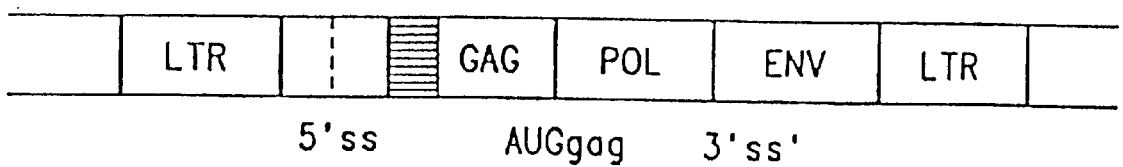
Figure 3:
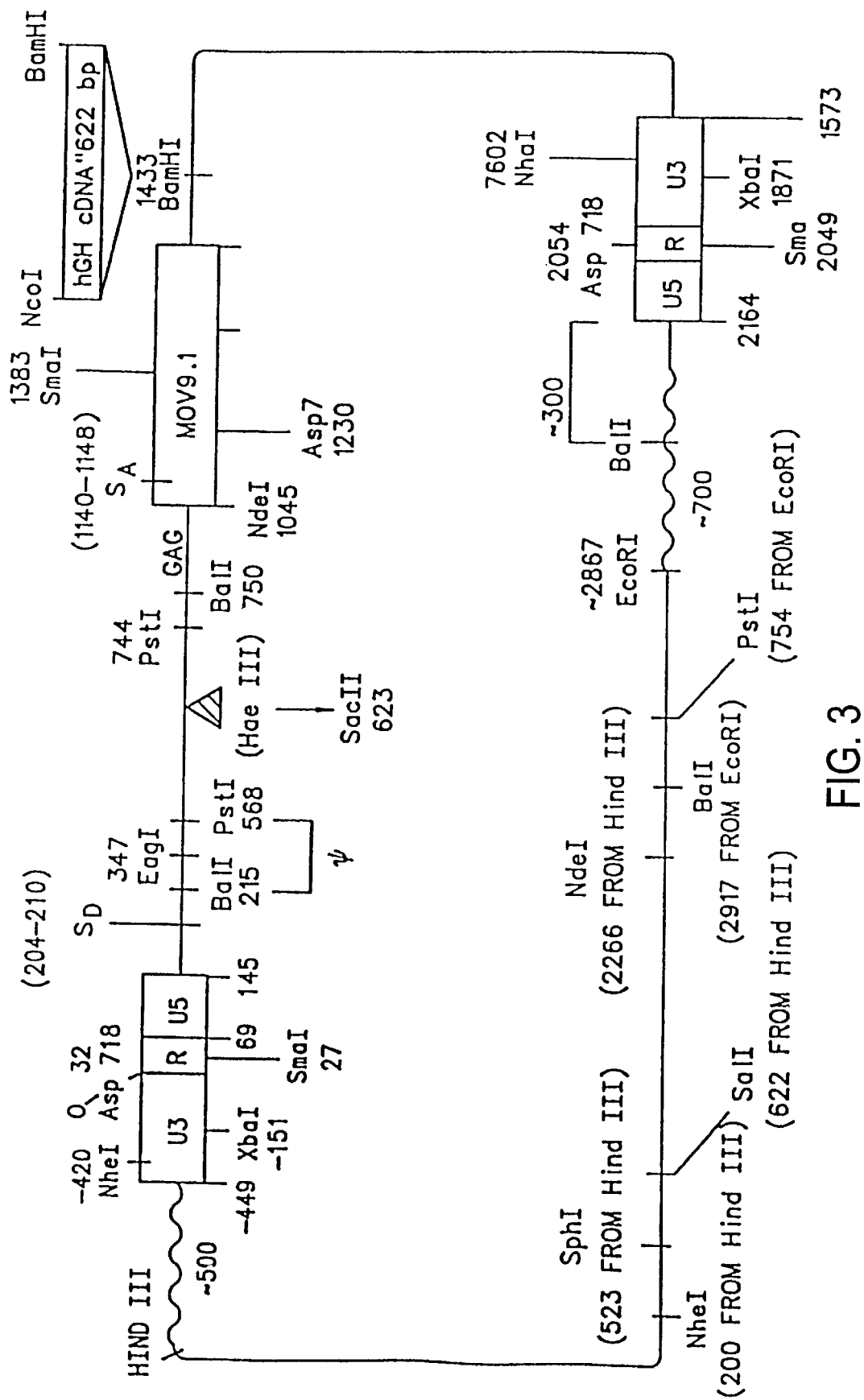
FIG. 3 is a schematic diagram of the retroviral vector MFG.
Figure 4:
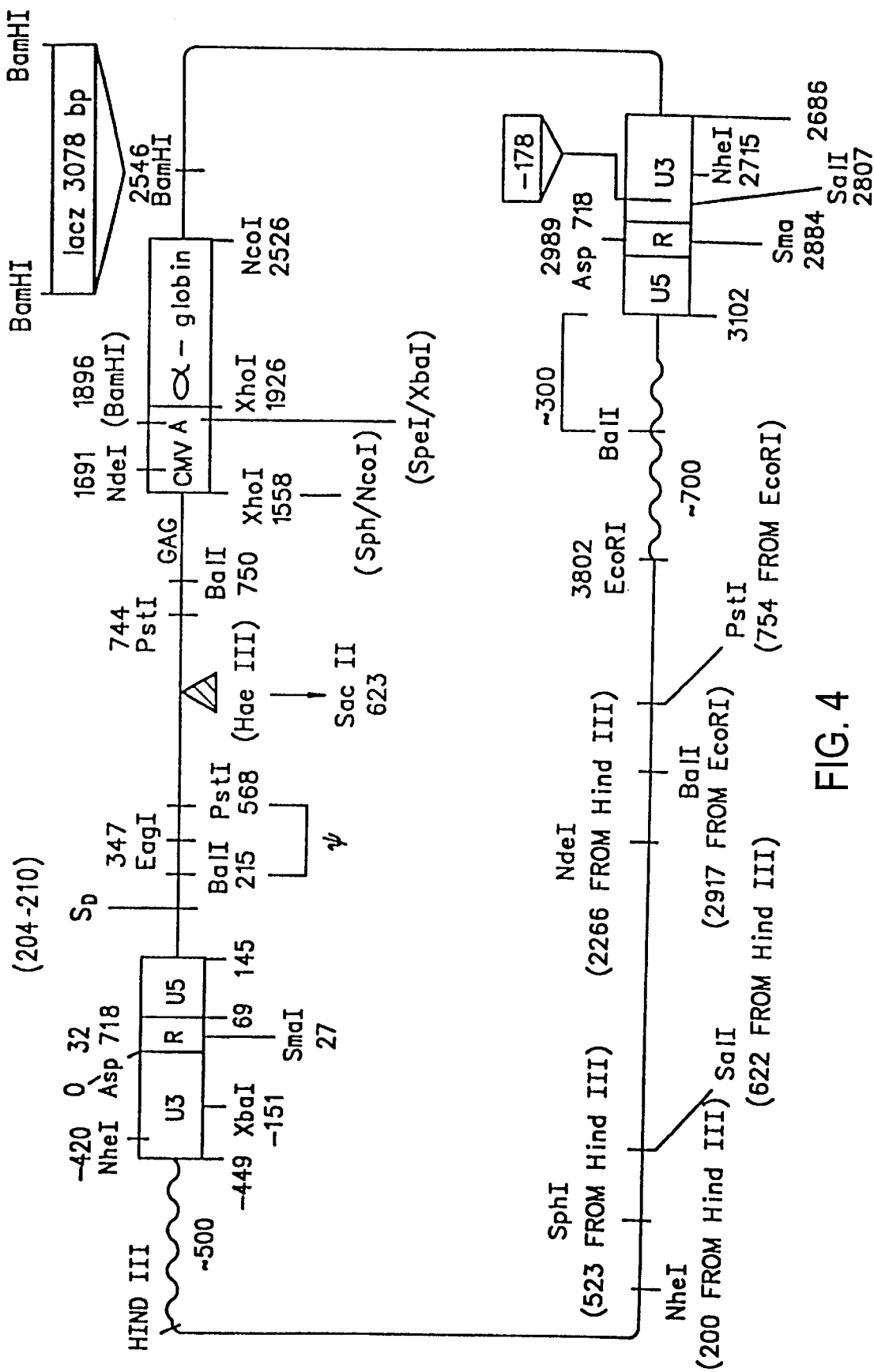
FIG. 4 is a schematic diagram of the retroviral vector α-SGC.

To demonstrate in vivo gene transfer, we used the marker gene concept published in 1987 (Price J., Turner D. Cepko C. 1987 *Proc. Natl. Acad. Sci. USA* 84:156160) with an improved vector based on the α-SGC vector (FIGS. 2*d* and 4). The lacz gene encoding beta-galactosidase was inserted into the α-SGC vector to generate the α-SGC-LacZ vector which is represented in FIG. 8. This recombinant construct was transfected into the t Crip packaging cell line and a clone of t Crip cells producing high titers of the α-SGC-LacZ recombinant retrovirus were isolated as described in Example 9, supra. Stocks of the α-SGC-LacZ recombinant retrovirus were used for in vivo transduction.

The experimental animals (rabbits) were anesthetized (ketamine/xylazine), both groins were shaved and prepped, and the animals positioned on an operating table. Through bilateral vertical groin incisions the common, superficial, and profunda femoral arteries were exposed. On the right (the side to be injured) small branches off the common femoral artery were ligated to insure that outflow from the isolated arterial segment would only occur through the internal iliac artery. If necessary, the inguinal ligament was divided and the vessel followed into the retroperitoneum to assure complete control of all side branches. The right superficial femoral artery (SFA) was ligated with 3-0 silk approximately 1.5 cm below the profunda take-off, control of the SFA was obtained at the SFA/profunda junction, and a transverse arteriotomy created. A fine wire (the stylet of a gauge Intracath was used), doubled upon itself to provide springiness to assure contact with the vessel wall, was passed up the common femoral and iliac artery retrograde to produce the defined injury described by Reidy et al. The wire was removed, a 20 gauge angiocath was inserted in the arteriotomy and secured to the underlying muscle for immediate access at the next surgical procedure. The incisions were closed in layers and the animals allowed to recover.

Twenty-four hours later a recombinant virus containing supernatant harvested from a crip producer of the α-SGC-LAC-Z vector and supplemented with polybrene to a final concentration of 8 ug/ml was used for in vivo transduction. The animals were again anesthetized and both incisions reopened in a sterile environment. To obtain control of the right iliac vessels above the area that had been injured with no disturbance to the previously denuded right iliac vessel, a #3 Fogarty™ balloon embolectomy catheter was inserted through an arteriotomy in the left superficial femoral artery, passed to the aortic bifurcation and the balloon inflated to interrupt blood flow. The right profunda femoris artery was occluded. The supernatant (10 ml) containing the recombinant retrovirus was introduced by hand injection through the angiocath previously placed in the right SFA. The supernatant flowed in a retrograde fashion from the right common femoral to the right external iliac and into the right internal iliac artery. By leaving the right internal iliac artery open outflow for the supernatant was allowed and a full 10 ml of supernatant could be instilled. In the experiments performed to date the supernatants have been exposed to the vessel wall for periods of four to eight minutes. The catheters from the left and right sides were then removed, hemostasis obtained, and the incisions closed.

Ten to fourteen days later animals were anesthetized prior to sacrifice. After anesthesia and prior to exposure, patency was assessed by direct palpation of the distal vessel. The infra-renal aorta and inferior vena cava were surgically exposed, cannulated, and the vessels of the lower extremity flushed with heparinized Ringer's lactate (2 U/ml) at physiologic pressure (90 mmhg.) A lethal dose of nembutal was administered and the arteries perfusion fixed in situ in 0.5% glutaraldehyde in 0.1 M cacodylate for 10 minutes. The aorta and both iliac arteries were excised in continuity and rinsed in phosphate buffered saline (PBS) with 1 mM $MgC_2$. The vessels were then stained for lacZ activity by incubation in the x-gal substrate for 1–1.5 hours at 37° C. When the reaction was complete, the x-gal solution was washed away and replaced with PBS.

10.2. Results

Two experiments have been completed with this protocol. Both experiments demonstrated successful in vivo transduction as shown by the in situ expression of the lacZ gene product in cells on the surface of the artery as visualized by the selective intense blue staining in a cytoplasmic pattern. A line of intensely stained blue cells consistent with the pattern of injury and proliferation described by Reidy et al. is found on the surface of a segment of the external illiac artery injured with a wire, exposed to α-SGC-LacZ recombinant retrovirus, fixed and stained for lacZ activity.

11. EXAMPLE: IN VIVO EXPRESSION OF HUMAN ADENOSINE DEAMINASE BY HEMATOPOIETIC STEM CELLS TRANSDUCED WITH SEVERAL RECOMBINANT MFG-ADA RETROVIRAL VECTORS

Several different MFG-based vectors encoding the same gene product, human adenosine deaminase (huADA) and the same vector backbone, yet differing specifically in transcriptional control sequences were constructed and evaluated for their capacity to efficiently transduce murine hematopoietic stem cells. Transduced stem cells were subsequently used in bone marrow transplantation experiments, and the long term vector-mediated expression of huada by various hematopoietic cells following transplantation.

11.1 Materials and Methods 11.1.1. Recombinant Retrovirus Vectors and Generation of Retrovirus-Producing Cells All recombinant retrovirus constructs but the αG-SGC vector are based on the retroviral vector MFG (MFG/Mo-LTR) described supra and depicted in FIG. 11A. All new structures generated were verified by DNA sequencing. Retroviral producer cell lines were generated by co-transfecting each retroviral plasmid with the plasmid pSV2-Neo into the amphotropic packaging cell line T CRIP as previously described (Danos and Mulligan, 1988, Proc. Natl. Acad. Sci. USA, 85:6460–6464). Cell-free supernatant was harvested after 10 days of selection in the presence of G418 at 1 mg/ml (Gibco BRL, Grand Island, N.Y.) and used to infect Ψ CRE cells. An αG-SGC producer was isolated after direct transfection into CRE cells. Twenty five clones per vector obtained by limiting dilution were screened for high-titer by Southern blot analysis. Titration was performed by infecting $5 \times 10^5$ NIH 3T3 cells with 0.5 ml of a 24 hours supernatant from the virus-producing clones in the presence of 8 μg/ml of polybrene (Sigma Chemical Co., St Louis, Mo.). Genomic DNA was extracted for Southern blot analysis to quantitate the number of proviral copies integrated in the target population. To verify the presence of the B2 mutation in the selected virus-producer cell lines and its transmission to infected 3T3 cells, PCR primers corresponding to Mo-MuLV nucleotides 72–92 and 470–490 were used to amplify a fragment of 400 bp which was then sequenced (fmol™ DNA Sequencing System, Promega, Madison, Wis.). Supernatants from Ψ CRE virus-producing cells and plasma from transplant recipients were tested for the presence of replication-competent virus based on a mobilization assay (Wilson et al., 1990, Proc. Natl. Acad. Sci. USA 87:439–443). In our study, the assay was modified to detect recombinant retroviral genomes expressing *Salmonella typhimurium* histidinol dehydrogenase as described (Hartman and Mulligan, 1988, Proc. Natl. Acad. Sci. USA 85:8047–8051).

Genomic DNA was prepared as described (Seif et al., 1991, Methods Mol. Cell. Biol. 2:216–217) and digested with Nhe I or Ec1136 II (for proviral structure) and Nco I or Bam HI (for proviral integration patterns). Hybridization filters were probed with a 721 bp $^{32}$p-labeled BamH I-Bgl II fragment of the hADA cDNA (Multiprime DNA labeling system, Amersham). The copy numbers were determined on a Phosphorimager (Fuji Bio-Imaging, Fuji Medical Systems, Stamford Conn.) relative to the intensity of bands generated in a cell line infected with a single copy of the provirus. To account for uneven loading, the band signal was normalized to the murine endogenous ADA band.

11.1.2. Transduction of Murine Bone Marrow Cells with Recombinant Retroviral Vectors and Transplantation of Transduced Cells into Mice Bone Marrow (BM) cells were obtained from the tibias and femurs of C57BL/6J male mice as previously described (Wilson et al., supra) (Jackson Laboratories, Bar Harbor, Me.), 6 days after intravenous injection of 150 mg/kg body weight of 5-fluorouracil. Transduction was achieved by coculturing BM cells for 48 hr on a monolayer of Ψ CRE producers in the presence of 10% (vol/vol) WEHI-3B supernatant and 4 µg/ml polybrene. Nonadherent cells were harvested and $2 \times 10^5$ to $4.5 \times 10^6$ viable cells per mouse were injected via the tail vein into total body irradiated (11 Gy) syngeneic female hosts. Transplanted mice were sacrificed 12 to 14 months after transplantation and samples of peripheral blood, EM, spleen, spleen-derived B and T lymphocytes, and BM-derived macrophages were analyzed for the presence of provirus and enzyme expression. B and T cells were harvested after 72 hr stimulation with 10 µg/ml of lipopolysaccharide (LPS) and 2 µg/ml of Concanavalin A (Sigma), respectively. More than 85% of cells were B or T lymphocytes as determined by FACS analysis. BM cells were cultured in medium containing 20% (vol./vol.) of L929 cell supernatant. More than 95% of cells harvested after 10–11 days were macrophages as determined by morphological analysis.

11.1.3. Adenosine Deaminase Assay

Isozyme-specific activity was detected in cell lysates by nondenaturing isoelectric focusing (IEF) (Multiphor II, Electrophoresis system, Pharmacia LKB, Piscataway, N.J.) as described (Wilson et al., supra). Total protein concentration was determined for each sample using the Bio-Rad protein assay (Bio-Rad, Melville, N.Y.). Fixed amounts of total protein were loaded on the IEF gels (300 µg for peripheral blood cells (PBC), 150 µg for BM, 120 µg for spleen, macrophages and B lymphocytes, 75 µg for T lymphocytes). After 12 minutes of staining reaction, the gels were fixed and the colorimetric intensity of each band was quantified using a computerized densitometer (Computing Densitometer, Molecular Dynamics, Sunnyvale, Calif.).

11.2. Results 11.2.1. Generation of Recombinant Retroviruses Encoding Human Adenosine Deaminase Insertion of the human ADA sequences into the MFG retroviral vector was performed so as to position the initiation ATG codon of the ADA cDNA at the position in the subgenomic viral transcript identical to that normally occupied by the viral envelope ATG. No selectable marker exists in the vector. Studies by Botwell and co-workers (Botwell et al., 1987, Mol. Biol. Med. 4:229–250; Botwell et al., 1988, J. virol. 62:2464–2473) and Ostertag (Beck-Engeser et al., 1991, Hum. Gene Therapy 2:61–70; which demonstrated the transcriptional activity of the myeloproliferative virus (MPSV) LTR in vectors. We generated derivatives of MFG-ADA which possessed either the enhancer of MPSV (positioned in the 3' MOLV LTR) or both 5' and 3' MoMLV LTRs in place of the Mo-MLV LTRS. In addition, previous studies have suggested the potential novel properties of the Moloney Friend Virus enhancer sequences (Holland et al., 1987, Proc. Natl. Acad. Sci. USA 84:8662–8666; Bösze et al, 1988, EMBO 5: 1615–1623; Thiesen et al, 1988, J. Virol. 62:614–618). Accordingly, MFG-ADA derivatives were generated with Mo-MLV enhancer sequences replaced by analogous Friend enhancer sequences. We also generated derivatives of MFG-ADA and the MPSV LTR containing derivative of MFG-ADA MPSV enhancer sequences which carry a mutation in the viral tRNA primary binding site, designated B2 (Barklis et al., 1986, Cell 47:391–397; Weiher et al., 1987, J. Virol. 61:2742–2746). Lastly, to provide a comparison of LTR-based vectors and vectors which employ internal promoters for expression of inserted genes, we generated αSGC-ADA. This vector utilizes a hybrid transcriptional element comprised of the human α globin promoter and CMV enhancer sequences and carries a deletion of enhancer sequences in the 3' LTR. The precise structure of each of the above constructs is described in Section 11.1.1., supra.

All of the above vectors were packaged in the ACRE packaging cell line. For each vector, approximately 25 cloned packaging cell lines were tested for virus production, and the specific cell line that transmitted the correct proviral structure at the highest copy number was selected by Southern blot analysis for future use. To select virus-producer cell clones for the Mo-LTR/B2 and MPSV-Enh/B2 constructs, which have retained the B2 mutation and are capable of transmitting it to NIH 3T3 cells, we amplified by PCR and sequenced a 400 bp fragment encompassing the B2 mutation in both producer and infected cells. The mutation was represented in half to one fourth of the virus-producer cell clones and in those cases in which it was present in producer cells, it was shown to be transmitted to target cells. After PCR analysis of 5 to 7 clones for each of the 2 constructs, high-titer clones were identified.

A Southern blot of DNA isolated from NIH 3T3 cells infected with virus obtained from selected producer clones representing each vector is shown in FIG. 11C. The data indicate that the correct proviral structures are in all cases transmitted to cells at high efficiency. The transmission efficiency of all viruses for transduction of NIH 3T3 cells was in a range of 0.7 to 3.6 copies of provirus per cell. These virus-producing clones were used to perform the experiments described in Sections 11.2.2. and 11.2.3., infra.

11.2.2. Detection and Quantitation of Human Adenosine Deaminase Activity in Recombinant MFG-ADA Vector-Transduced Murine Bone Marrow Transplant Recipients To investigate human adenosine deaminase (huADA) expression in cells derived from transduced hematopoietic stem cells in vivo, mice were transplanted with $2.5 \times 10^5$ to $4.5 \times 10^6$ BM cells that had been co-cultured with recombinant virus producing cells as described in Section 11.1.2., supra. Fifteen to eighteen mice were transplanted per construct. A first step in assessing vector mediated gene expression involved the analysis of huADA enzyme activity in the peripheral blood cells (PBC) of reconstituted animals 5–7 months after transplantation using the assay described in Section 11.1.3., supra (FIG. 12). In this assay, human ADA activity can be readily separated from the murine ADA activity and the relative levels of the two activities can be estimated by densitometry measurements of the intensity of labeled in situ reaction products. This assay generates signals proportional to the amount of enzyme activity.

In mice repopulated with cells transduced with the recombinant MFG-ADA vectors, 90 out of 93 transplanted animals expressed huADA. In 83% of those transplanted animals (77/93), the level of expression of huADA was equal to or greater than the level of endogenous murine ADA (MADA) expression. In 14% of these mice (13/93), the levels of huADA were in the order of ¼ to ¾ of the murine ADA. Only 3% of, the animals (3/93) did not express the huADA at a detectable level. In mice reconstituted with the αG-SGC-infected cells, only 4 mice out of 11 expressed huADA at levels close to the murine enzyme and 6 at much lower levels (FIG. 12). The small percentage of mice which express huADA from this vector is probably due to the low copy number of provirus detected in the tissues of these animals. Based on the average ratio of human to murine activity observed from mouse to mouse in these studies, the data suggest that the MFG-ADA derivative which utilizes the MPSV LTRs rather than Mo-MLV LTRs yielded moderately more enzyme than the other constructs (about 2 fold). However, this data does not take into account potential differences in proviral DNA copy number.

11.2.3. Long-Term In Vivo Expression of Human Adenosine-Deaminase by Various Hematopoietic Cell Lineages Following Bone Marrow Transplantation Based on the high frequency of bone marrow transplant recipients which demonstrated significant gene expression in the peripheral blood seven months after bone marrow transplantation, a smaller number of animals were further examined for vector expression in a number of different hematopoietic cell types at much longer times after transplantation (greater than one year). A first step in these studies was to reanalyze the mice previously analyzed for enzyme expression in peripheral blood. As is shown in FIG. 12B, comparison of the relative amounts of human and mouse enzymes at the two time points (shown below each IEF gel track) indicates that little if any significant decrease in huADA expression occurred over time. As shown in the boxes labeled with the different vectors, approximately 80% of the expression observed at 7 months persists after one year. In mice engrafted with ASGC-ADA treated cells, a slightly more significant decrease in expression was observed.

In the next series of experiments, expression of huADA in different hematopoietic cell types was examined by fractionating each cell population and quantitating enzyme activity and proviral copy number. This analysis included 3–5 animals engrafted with cells transduced by either (i) MFG-ADA; (ii) MFG-ADA (+B2); (iii) MFG-ADA(Friend enhancer); (iv) MFG-ADA (MPSV-LTRs); or, (v) α-SGC-ADA. The cell populations subjected to enzyme and DNA analysis included whole bone marrow, whole spleen, and fractionated macrophages, T lymphocytes, and B lymphocytes. A compilation of all the data obtained, expressed in several different ways, is shown in FIG. 13. Panel A displays data representing individual mice, while other panels represent average values.

Collectively, the data may be summarized as follows:

1. Average proviral copy number achieved by different viruses:

FIG. 13, panel C, shows that a significant proportion of the different hematopoietic cell populations carry proviral sequences even at over one year post-transplantation. With the exception of the α-SGC-ADA animals, where fewer cells appear to carry provirus, each of the other vectors yielded comparable proviral copy numbers (0.2–0.7 copies/cell) in all lineages. The error bars illustrate that there is, however, significant variation in proviral copy number from mouse to mouse. It is possible that specific transduced stem cell clones contribute unequally to different lineages, causing the observed variations in copy number.

2. Average expression levels of huADA achieved by different viruses:

The results presented in FIG. 13, panel D, indicate that on average there is a remarkably similar level of gene expression attained in the different hematopoietic cell lineages by the different vectors. This conclusion is quite important, for it suggests that the vectors examined do not, to any great extent, exhibit tissue specificity of gene expression, and therefore may well be useful for a variety of applications in which expression is required in a specific cell lineage, yet permissible in other cells.

The results presented in FIG. 13, panels B and D, demonstrate that while all vectors yield gene expression in different hematopoietic cell lineages, both the MoLTR-B2 and the MPSV-LTR derivatives of MFG-ADA appear to yield greater levels of gene expression in most lineages in relation to the parental MFG-ADA vector. Because of the significant variation in expression levels from mouse to mouse, and the relatively small number of animals examined, it was important to provide statistical analysis of the data. As shown in panels B and D of FIG. 13, the bars marked with an asterisk indicate values that are statistically significant relative to values for the parental MFG-ADA vector. This data indicates that only the B2 and MPSV LTR derivatives show significant differences in expression in relation to the MFG-ADA vector. In the case of the B2 vector, significance could not be established for the T lymphocyte lineage, due to the wide variation in expression levels observed from mouse to mouse. Similarly, statistical significance could not be established for the macrophage lineage in the case of MPSV-LTR derivative of MFG-ADA.

Another useful way to express the data provided in FIG. 13, panel A, is to consider the levels of expression in each lineage per mg protein, rather than per proviral copy number per mg protein. This representation of the data is perhaps most relevant to an assessment of the overall performance of each vector, since it takes into account both the inherent expression potential of the vector and the ability of the vector to transduce cells. Interestingly, because of the comparable proviral copy numbers achieved by each vector (except for the αSGC-ADA vector), the data in FIG. 13, panel D, is quite similar to that represented in panel B. Again, statistically significant differences in gene expression relative to MFG-ADA mouse were observed with both the B2 and MPSV-LTR vectors. In contrast to the data provided in panel B, expression of the B2 vector in macrophages was not significantly different than that achieved by MFG-ADA.

12. EXAMPLE: MFG VECTOR DERIVATIVES WITH IMPROVED SAFETY FEATURES

The MFG-S vector is a derivative of the MFG vector that was designed to even further minimize the possibility of the formation of replication-competent virus through homologous recombination events. Specifically, MFG retains two intact overlapping open reading frames ("ORFs") that encode the amino terminal portion of both the cell surface and cytoplasmic gag-pol polyproteins. These ORFs provide a target region for recombination events with viral structural coding sequences present in the packaging cell line which could lead to the formation of replication-competent virus. In order to minimize this already remote possibility, the MFG-S vector was constructed so that three specific mutations have been introduced into the viral gag region to disrupt the ORFs and thereby minimize any possibility of the expression of either cell surface or cytoplasmic gag-related polypeptides of any appreciable size.

The specific mutations to the MFG retroviral vector to produce the MFG-S retroviral vector are shown by direct comparison of the MFG and MFG-S DNA sequences in FIG. 14. These are an A to T change at nucleotide 1256 and a C to T mutation at nucleotide 1478. These mutations create stop codons downstream from the initiation codons for the cell surface or cytoplasmic gag polypeptides and reduce the corresponding gag-related ORFs to 84 and 15 nucleotides, respectively. A third mutation was engineered into the DNA sequence which changes a T to an A at nucleotide 1273. This change does not effect the ORF but is a compensatory change that preserves the potential for base pairing with nucleotide 1252 preserving a stem loop that is theoretically important for the packaging function.

The salient features of the MFG-S retrovirus and their location by nucleotide position are listed in Table II below.

TABLE II

| FEATURE | NUCLEOTIDE POSITION |
|---|---|
| 5' - murine flanking sequences | 1–396 |
| U3 region of 5' - LTR | 397–845 |
| RNA cap site | 846 |
| R region of 5' - LTR | 846–913 |
| U5 region of 5' - LTR | 914–990 |
| Primer binding site | 991–1007 |
| Splice donor site | 1048–1052 |
| Start codons for cell surface gag ORF | 1172–1174, 1202–1204 |
| Start codon for cytoplasmic gag ORF | 1466–1468 |
| MFG-S base pair substitutions | 1256, 1273, 1478 |
| Splice acceptor site | 1983–1991 |
| Nco I restriction site | 2276–2281 |
| Bam HI restriction site | 2285–2290 |
| U3 region of 3' - LTR | 2429–2877 |
| R region of 3' - LTR | 2878–2945 |
| Polyadenylation signal | 2923–2929 |
| U5 region of 3' - LTR | 2946–3022 |
| 3' - mouse flanking sequences | 3023–3718 |

FIG. 15 shows the structural features of the MFG-S retroviral vector. The MFG-S vector consists of the following parts: (1) a Mo-MuLV DNA fragment containing the 5' LTR and downstream sequence extending to the Nar I site at nucleotide position 1039 (Nar I was converted to Nde I site); (2) a Smal linker at nucleotide position 626 of the retroviral sequence; (3) a Mo-MuLV DNA fragment extending from the Nde I site at position 5401 to an Xba I site at nucleotide position 5674; (4) a synthetic double-stranded DNA fragment containing an Nco I site (CTAGACTTGCCATGGCGCGATC); (5) a Mo-MULV fragment extending from the Cla I (converted to a Bam HI site) site at nucleotide position 7672 through the 3' LTR; and (6) pBR322 bacterial plasmid sequences. Nucleotide substitutions were made at position 1256, 1273, and 1478 of the Mo-MuLV sequence in the MFG-S vector. These nucleotide positions are relative to the Hind III site of the vector (see complete nucleotide sequence of MFG-S in FIG. 17). The proviral transcription unit of MFG is flanked by 396 nucleotides of mouse genomic sequences on the 5' end and 697 nucleotides on the 3' end. cDNA sequences can be inserted between the unique Nco I and Bam HI sites. The flanking mouse genomic and proviral sequences are cloned between the Hind III and Eco RI sites of pBR322. The Bam HI site in pBR322 was eliminated.

FIG. 16 provides a circular restriction map of the MFG-S vector. FIG. 18 provides a restriction map of the MFG vector in table form.

13. EXAMPLE: HUMAN CLINICAL STUDIES
13.1. Melanoma Trials

Melanoma patients in which the disease had progressed to a stage where the surgery did not remain as an effective option were used in the study. The study also required that the patients show no evidence of autoimmune disease, serious allergy, or brain metastases (as determined by magnetic resonance imaging, MRI), and retained adequate immune, hepatic, renal, and bone marrow function.

The huGM-CSF gene was subcloned into the insertion site of the retroviral vector MFG-S in a proper context and orientation for expression of the gene. The recombinant vector was subsequently transfected into the amphotropic packaging cell line pCRIP and high producer transfectants were isolated. High titer stocks of helper free retroviral particles which harbor the huGM-CSF gene were then harvested from the culture medium of the transfected packaging cell lines essentially as described above.

Tumor cells were resected from cutaneous and subcutaneous lesions, lymph nodes, and lung, liver, and soft tissue metastases. After resection, the specimens were aseptically transferred to a sterile container and transported to the laboratory. All subsequent procedures were conducted under aseptic conditions. The tumor tissues were disaggregated by either collagenase treatment or by mechanical dissociation and subsequently grown in culture and/or frozen in DMSO with 50 percent FCS (collagenase treated) or human albumin (mechanical dissociation). The numbers of the primary and secondary autologous tumor cells were expanded in culture, and a portion of the cells were subsequently transduced to produce huGM-CSF using the MFG-S construct described above.

After verification that the transduced cells were sterile, viable and producing cytokine, (see Table 2), a total of either $5 \times 10^6$ (low dose) or $5 \times 10^7$ (high dose) of the transduced tumor cells were irradiated, suspended in normal saline, and injected (both intradermally and subdermally at up to five different sites in volumes of 0.25–1.0 ml) back into the original donors. Up to three injections at the given dosages were applied to the individuals at approximately 21 day intervals. Control individuals were separately injected with irradiated non-transduced cells and levels of GM-CSF analogous to the amounts of GM-CSF produced by the transformed cells which were injected into the test subjects.

TABLE 3

| GM-CSF Production (ng/$10^6$ cells/24 hrs) ||
|---|---|
| TEST SUBJECT | GM-CSF PRODUCTION |
| (Low Dose) | |
| 001 | 168.2 |
| 002 | 251.6 |
| 006 | 124.6 |
| 008 | 97.1 |
| 010 | 46.0 |
| 011 | 123.6 |
| 020 | 180.0 |
| (High Dose) | |
| 018 | 187.3 |
| 019 | 128.3 |

After injection, tests were performed to confirm that the transfected tumor cells elicited an immune response. These tests included assaying for delayed type hypersensitivity (DTH) reactions to intradermally injected (irradiated) tumor cells, and biopsies of the vaccination and injection sites. The data indicate that T-cells are present in the inflamed tissues, and that there is a reproducible increase in the number of monocytes. The control subjects (who were injected with either nontransduced tumor cells or huGM-CSF at levels analogous to those produced by the transduced autologous tumor cells) showed little to none of the differences seen in the test subjects. Immunohistochemistry indicated that a tendency for antigenic drift correlated with decreased expression of the Mel 4 and HMB45 markers.

Additional tests were conducted to determine whether or not an increase in the number of eosinophils correlated with the injections. As seen in FIG. 10, after each vaccination, a transient increase in the percentage of eosiniophils in the bloodstream generally followed.

The above data indicate that immune stimulation had occurred, and that the observed immune stimulation could be associated with the fact that the autologous tumor cells were expressing the MFG-S encoded huGM-CSF gene in vivo.

13.2. Renal Cell Carcinoma Trials

Eighteen patients with advanced renal cell carcinoma were vaccinated up to four times (at approximately one month intervals) with either $4 \times 10^6$, $4 \times 10^7$, or $4 \times 10^8$ transduced and irradiated tumor cells. Tumor tissue was surgically resected (see above), and the population of primary and secondary tumor cells was expanded by in vitro culture. The cultured cells were subsequently transduced with the huGM-CSF/MFG-S construct described above, and tested for GM-CSF production. Transduced autologous cells which produced acceptable quantities of cytokine were irradiated and injected into the donor individuals as described above.

At the lowest dose of injected cells, the levels of huGM-CSF secreted ranged between about 17 and 189 ng/$10^6$ cells/24 hrs. At the middle dose, the transduced cells constructed from the various individuals' tumors secreted between about 42 and 149 ng of GM-CSF/$10^6$ cells/24 hrs.

Control individuals were injected with irradiated non-transduced tumor cells. At the lowest dose, three subjects received non-transduced cells, at the middle dose of cells, five subjects received non-transduced cells, and the two patients that were injected with the highest dosage of cells only received nontransduced cells.

Patient responses to the vaccinations included marked erythema and induration at the injection site (Dose 1 showed the least response), which became more pronounced after multiple vaccinations (this was especially the case when transduced cells were injected).

Moreover, test subjects who were multiply injected with transduced cells also displayed positive DTH reactions, as well as an increase in the amount of eosinophils (following vaccination). As in the melanoma study, apart from local symptoms (erythema, induration and itching), no significant adverse events were observed.

The above data reveal that injecting irradiated transduced (using MFG-S) autologous tumor cells expressing huGM-CSF into human test subjects stimulated an observable in vivo tumor-specific immune response against the parent tumor cells. These data demonstrate that the subject vectors may be used to provide a therapeutic benefit in humans.

14. BIOLOGICAL DEPOSITS

On Oct. 3, 1991, Applicants have deposited with the American Type Culture Collection, Rockville, Md., USA (ATCC) the plasmid MFG with the factor VIII insertion, described herein ATCC accession no. 68726, plasmid MFG with the tPA insertion, described herein, given ATCC accession no. 68727, the plasmid α-SGC, described herein, with the factor VIII insertion, given ATTC accession no. 68728, and plasmid α-SGC with the tPA insertion, described herein, given ATCC accession no. 68729. On Oct. 9, 1991, Applicants have deposited with the American Type Culture Collection, Rockville, Md., USA (ATCC) the plasmid MFG, described herein, given ATCC accession no. 68754, and plasmid α-SGC, described herein and given ATCC accession no. 68755. These deposits were made under the provisions of the Budapest Treaty on the International Recognition of the Deposit of Microorganisms for the purposes of patent procedure and the Regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

Those skilled in the art will recognize, or be able to ascertain using no more than routine experimentation, many equivalents to the specific embodiments of the invention described specifically herein. Such equivalents are intended to be encompassed in the scope of the following claims.

All patent, patent applications, and publications cited herein are hereby incorporated by reference.

What is claimed is:

1. A recombinant retroviral vector, said vector comprising in operable combination
    a) 5' R and U5 sequences, and 3' U3 and R sequences derived from the LTRs of a retrovirus of interest;
    b) a Psi packaging site recognized by an amphotropic retrovirus;
    c) an insertion site for a gene of interest located 3' to said U5 sequence; and
    d) a splice acceptor site located 3' to said Psi packaging site, wherein said splice acceptor site is a splice acceptor site necessary for the generation of the env mRNA of a wild type retrovirus;

wherein said recombinant retroviral vector does not contain a complete gag, pol, or env gene, and does not express a functional marker gene.

2. The recombinant retroviral vector according to claim 1 further comprising a portion of the gag coding sequence; a splice donor site and a splice acceptor site located upstream from said insertion site.

3. The recombinant retroviral vector according to claim 2 further comprising a gag transcriptional promoter functionally positioned such that a transcript of a nucleotide sequence inserted into said insertion site is transcribed with a 5' gag untranslated region.

* * * * *